(12) United States Patent
Sokol et al.

(10) Patent No.: US 10,736,927 B2
(45) Date of Patent: Aug. 11, 2020

(54) PHARMACEUTICAL COMPOSITIONS FOR PREVENTING OR TREATING INFLAMMATORY BOWEL DISEASES

(71) Applicants: INSERM (INSTITUT NATIONAL DE LA SANTE ET DE LA RECHERCHE MEDICALE), Paris (FR); UNIVERSITE PIERRE ET MARIE CURIE (PARIS 6), Paris (FR); INSTITUT NATIONAL DE LA RECHERCHE AGRONOMIQUE (INRA), Paris (FR); CENTRE NATIONAL DE LA RECHERCHE SCIENTIFIQUE (CNRS), Paris (FR); ASSISTANCE PUBLIQUE-HOPITAUX DE PARIS (APHP), Paris (FR)

(72) Inventors: Harry Sokol, Paris (FR); Mathias Lavie-Richard, Jouy-en-Josas (FR); Marie-Laure Michel, Jouy-en-Josas (FR); Bruno Michel Lamas, Paris (FR); Philippe Langella, Jouy-en-Josas (FR)

(73) Assignees: INSERM (INSTITUTE NATIONAL DE LA SANTÉ ET DE LA RECHERCHE MEDICALE), Paris (FR); UNIVERSITÉ PIERRE ET MARIE CURIE (PARIS 6), Paris (FR); INSTITUT NATIONAL DE RECHERCHE POUR L'AGRICULTURE, L'ALIMENTATION ET L'ENVIRONNEMENT, Paris (FR); CENTRE NATIONAL DE LA RECHERCHE SCIENTIFIQUE (CNRS), Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 0 days.

(21) Appl. No.: 15/753,475

(22) PCT Filed: Aug. 22, 2016

(86) PCT No.: PCT/EP2016/069797
§ 371 (c)(1),
(2) Date: Feb. 19, 2018

(87) PCT Pub. No.: WO2017/032739
PCT Pub. Date: Mar. 2, 2017

(65) Prior Publication Data
US 2018/0250350 A1   Sep. 6, 2018

(30) Foreign Application Priority Data

Aug. 21, 2015 (EP) .................... 15306303
Nov. 10, 2015 (EP) .................... 15306788

(51) Int. Cl.
| A61K 35/747 | (2015.01) |
| C12R 1/225 | (2006.01) |
| A61P 1/00 | (2006.01) |
| G01N 33/50 | (2006.01) |

(52) U.S. Cl.
CPC .............. *A61K 35/747* (2013.01); *A61P 1/00* (2018.01); *C12R 1/225* (2013.01); *G01N 33/5008* (2013.01); *G01N 2333/70567* (2013.01); *G01N 2500/00* (2013.01); *G01N 2800/065* (2013.01); *G01N 2800/52* (2013.01); *Y02A 50/473* (2018.01)

(58) Field of Classification Search
CPC ...... G01N 33/5008; A61K 35/747; A61P 1/00
See application file for complete search history.

(56) References Cited

FOREIGN PATENT DOCUMENTS

| EP | 2 392 340 | 12/2011 |
| EP | 2 615 163 | 7/2013 |

OTHER PUBLICATIONS

Monteleone et al, www.co-gastroenterology.com, vol. 28, No. 4, Jul. 2012 "The aryl hydrocarbon receptor in inflammatory bowel disease: linking the environment to disease pathogenesis" (Year: 2012).*
Zelante et al. Immunity 39, 372-385, Aug. 2013 "Tryptophan Catabolites from Microbiota Engage Ary Hydrocarbon Receptor and Balance Mucosal Reactivity via Interleukin-22" Year: 2013).*
U.S. Appl. No. 16/337,951, filed 2019.*
Lamas, B. et al. "CARD9 impacts colitis by altering gut microbiota metabolism of tryptophan into aryl hydrocarbon receptor ligands" *Nature Medicine*, Jun. 2016, pp. 598-605, vol. 22, No. 6, Suppl pp. 1-4.
Leone, V. A. et al. "Diet, gut microbes, and genetics in immune function: Can we leverage our current knowledge to achieve better outcomes in inflammatory bowel diseases?" *Current Opinion in Immunology*, Dec. 1, 2014, pp. 1-14, vol. 31.
Sarmiento-Rubiano, L.-A. et al. "Characterization of a novel *Lactobacillus* species closely related to *Lactobacillus johnsonii* using a combination of molecular and comparative genomics methods" *BMC Genomics*, 2010, pp. 1-16, vol. 11, No. 504.

(Continued)

*Primary Examiner* — Ruth A Davis
(74) *Attorney, Agent, or Firm* — Saliwanchik, Lloyd & Eisenschenk

(57) ABSTRACT

The present invention relates to methods and pharmaceutical compositions for preventing or treating inflammatory bowel diseases.

10 Claims, 20 Drawing Sheets
Specification includes a Sequence Listing.

(56) References Cited

OTHER PUBLICATIONS

Takamura, T. et al. "*Lactobacillus bulgaricus*, OLL1181 activates the aryl hydrocarbon receptor pathway and inhibits colitis" *Immunology and Cell Biology*, 2011, pp. 817-822, vol. 89, No. 7.
Wang, L.-T. et al. "*Lactobacillus taiwanensis*, sp. nov., isolated from silage" *International Journal of Systematic and Evolutionary Microbiology*, Jul. 15, 2009, pp. 2064-2068, vol. 59, No. 8.
Written Opinion in International Application No. PCT/EP2016/069797, dated Jan. 2, 2017, pp. 1-14.
Zhu, C. et al. "The Role of AhR in Autoimmune Regulation and Its Potential as a Therapeutic Target against CD4 T Cell Mediated Inflammatory Disorder" *International Journal of Molecular Sciences*, 2014, pp. 10116-10135, vol. 15.

\* cited by examiner

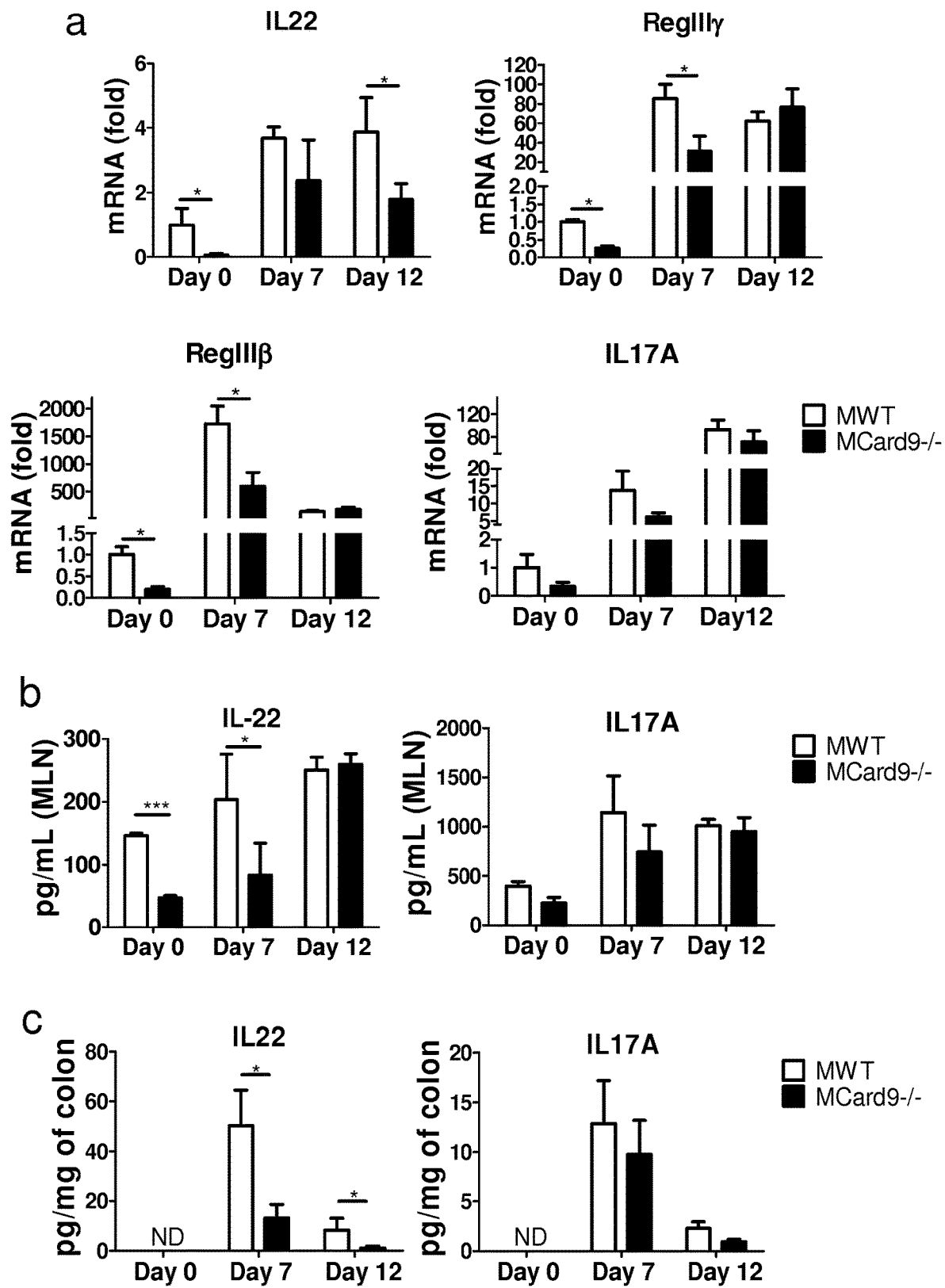
Figure 4 a, b and c

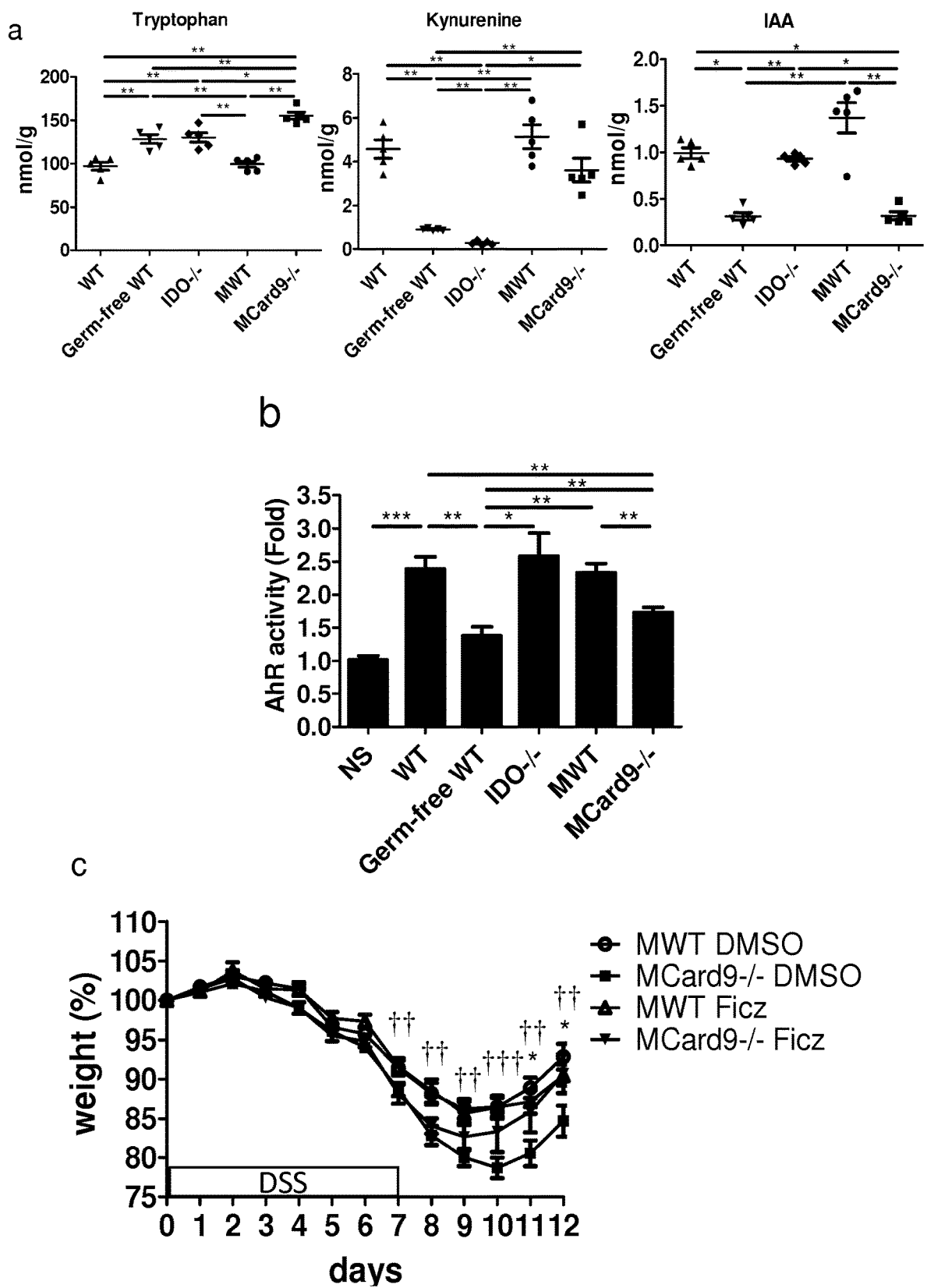
Figure 5 a, b and c

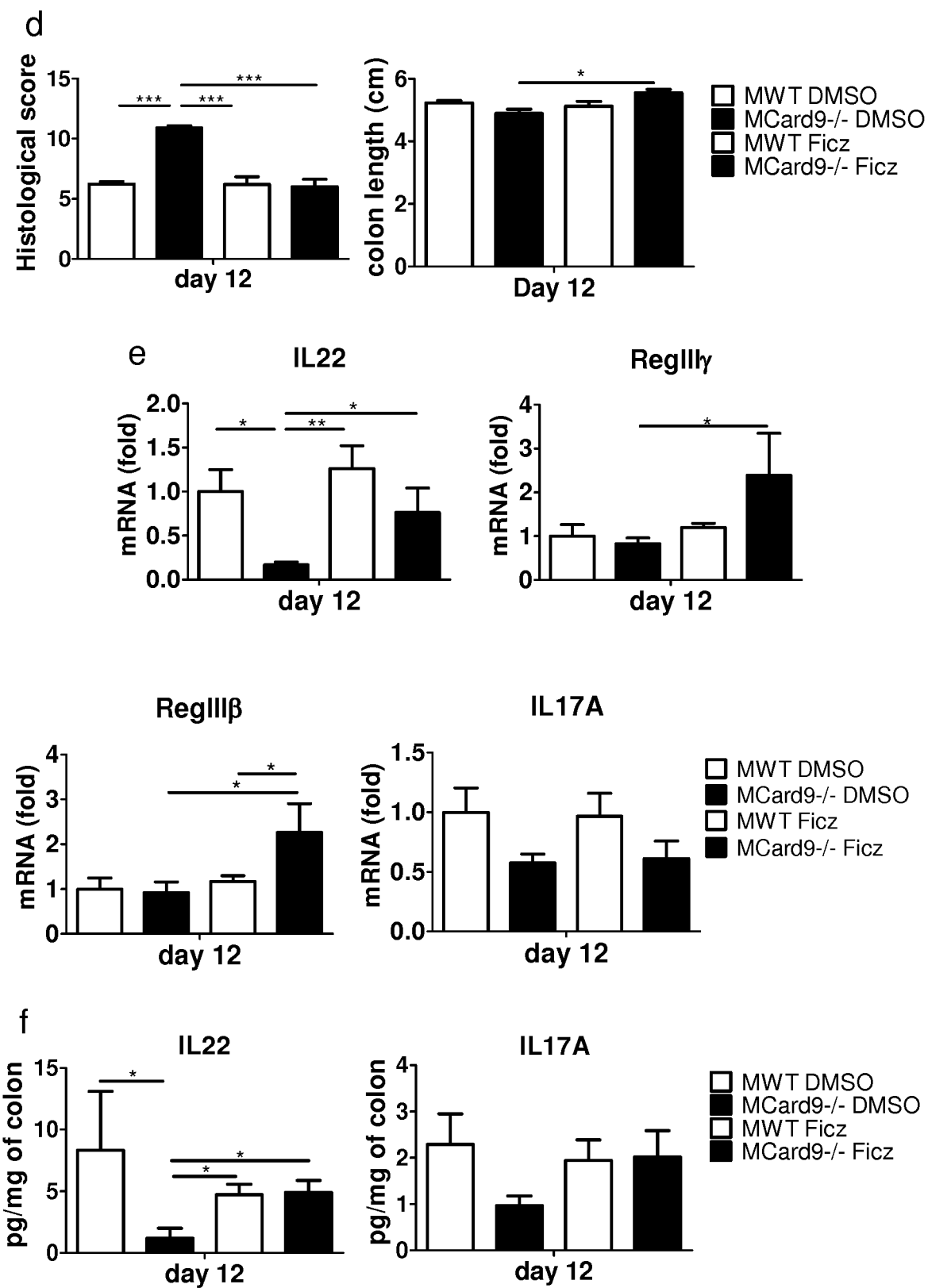
Figure 5 d, e and f

Figure 9:
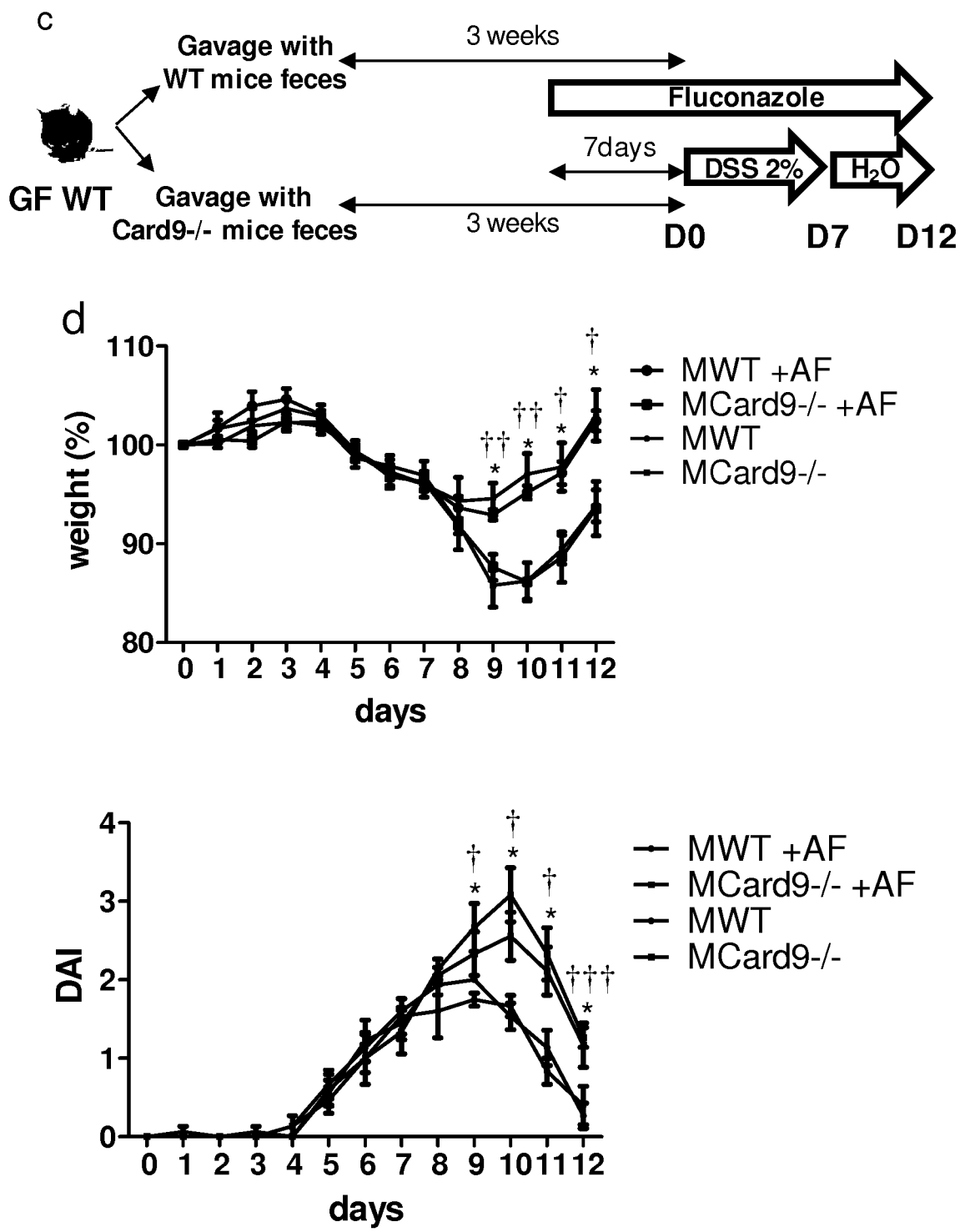

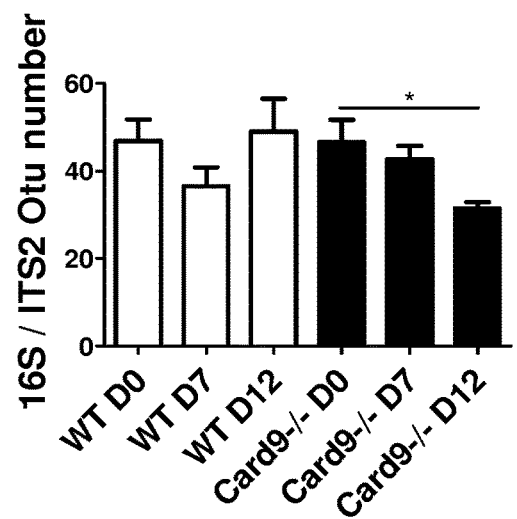
Figure 8
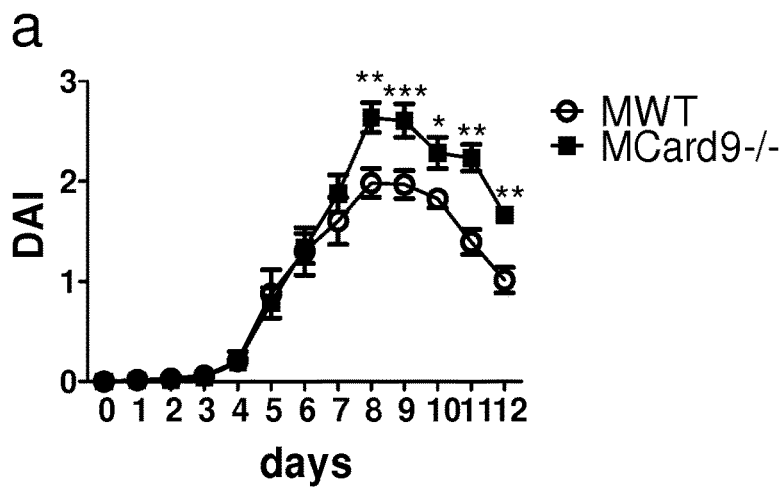
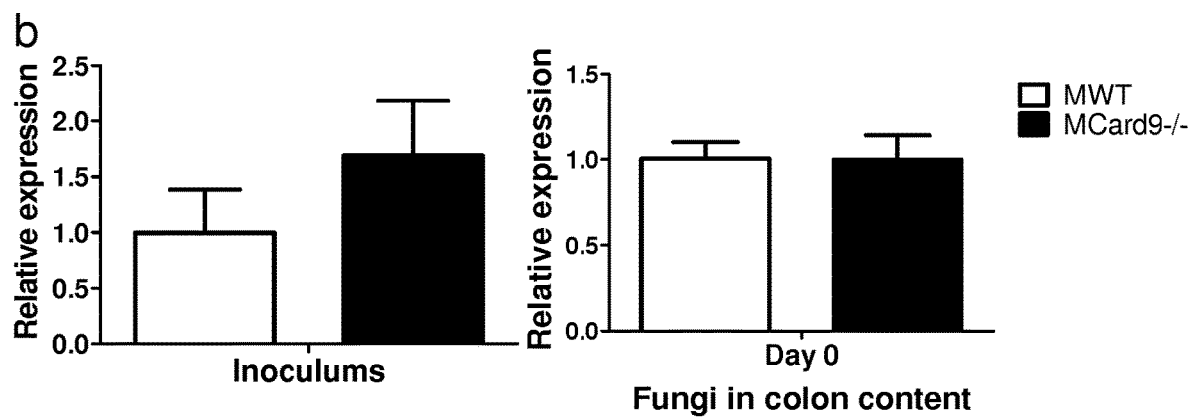
Figure 9 a and b

Figure 9 c and d

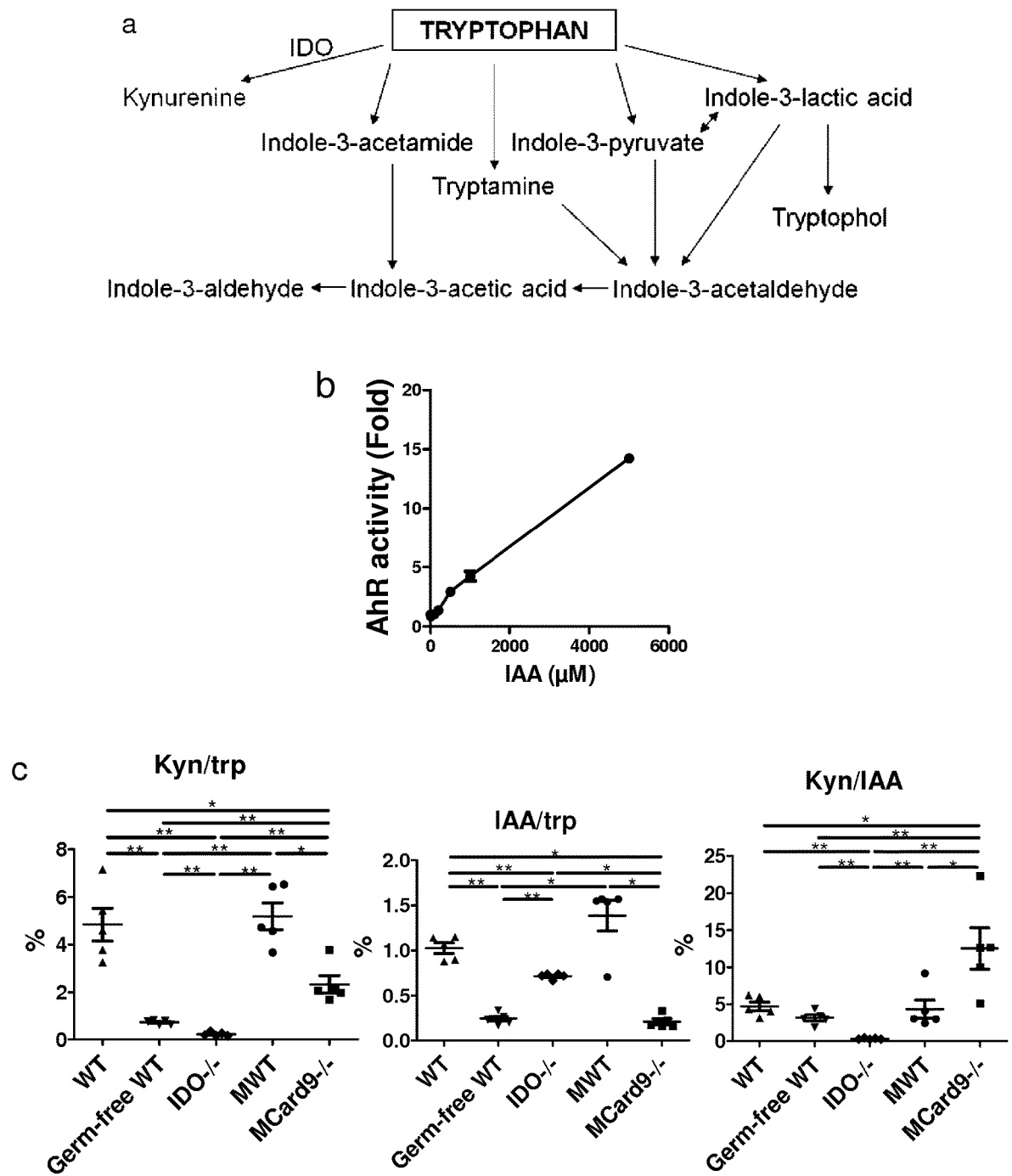
Figure 12 a, b and c

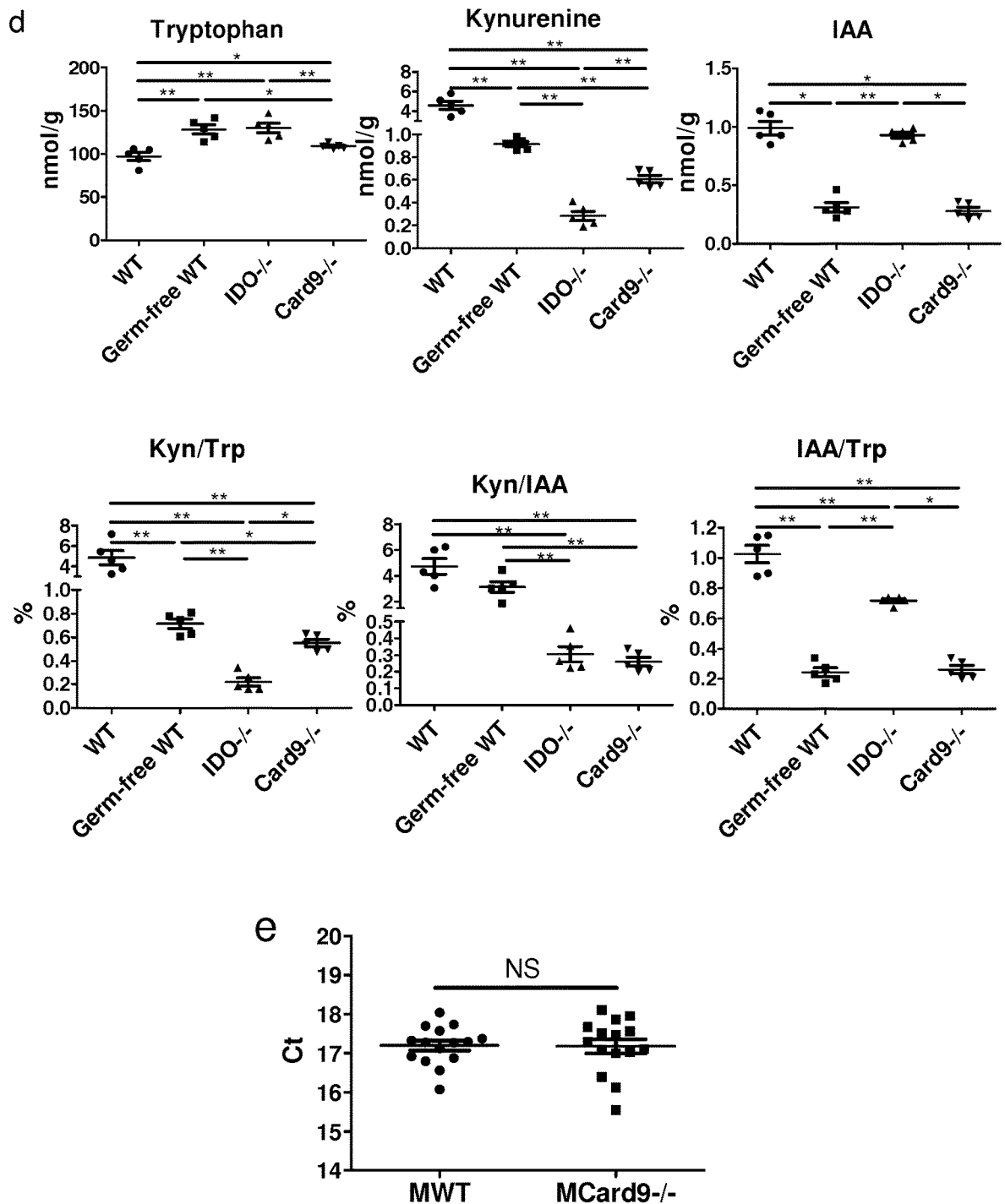
Figure 12 d and e

Figure 13:
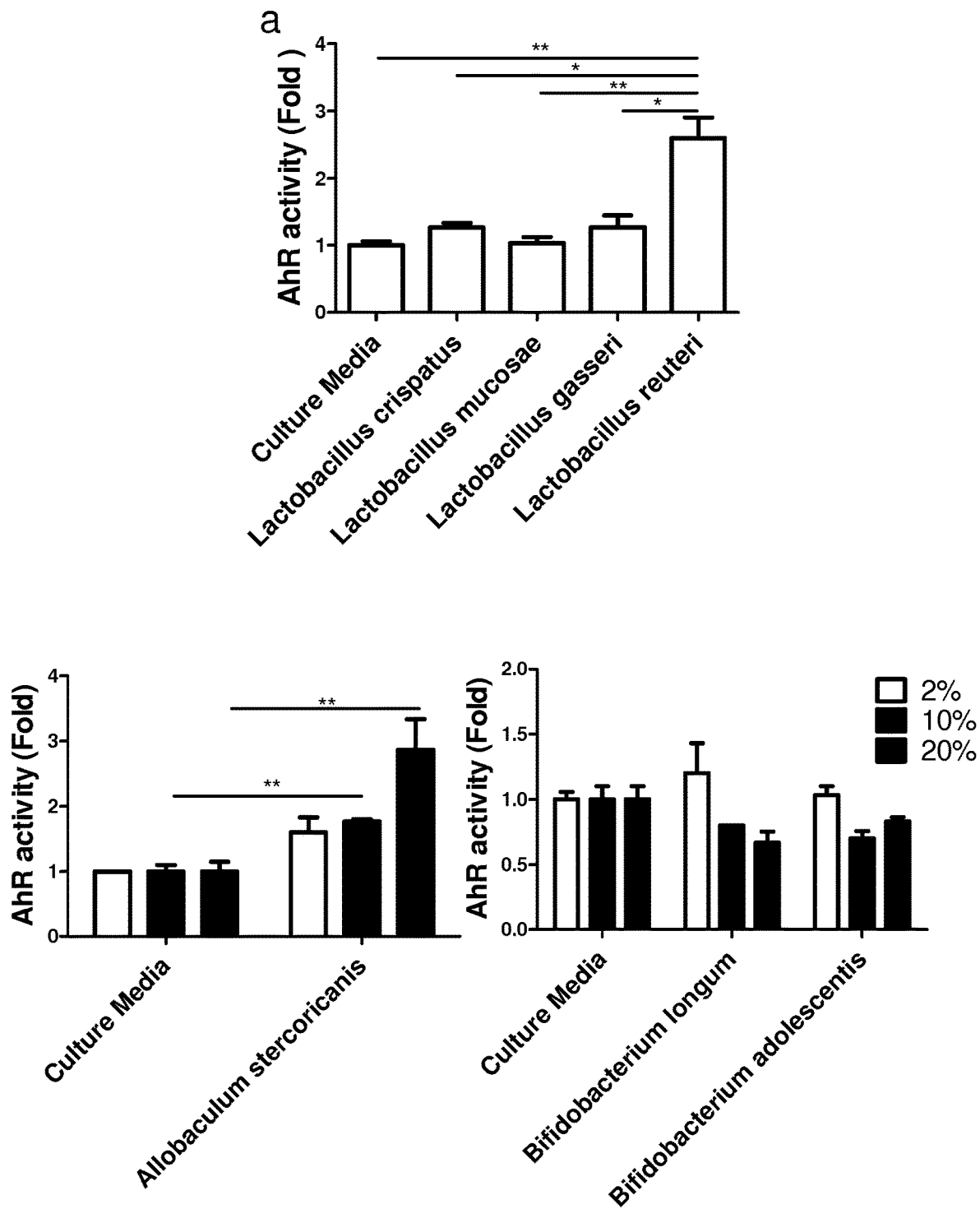

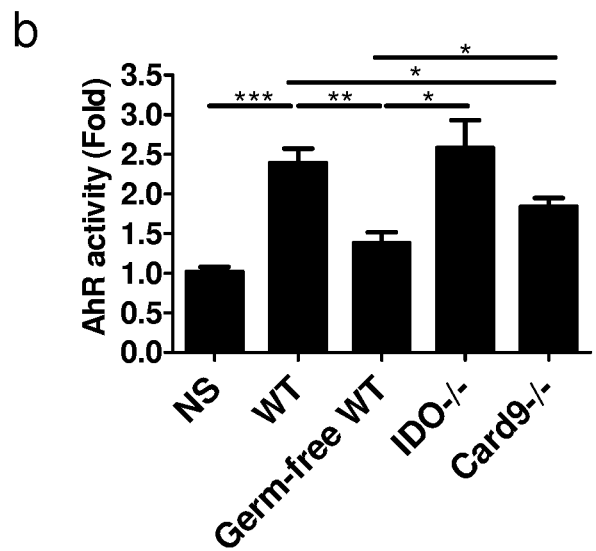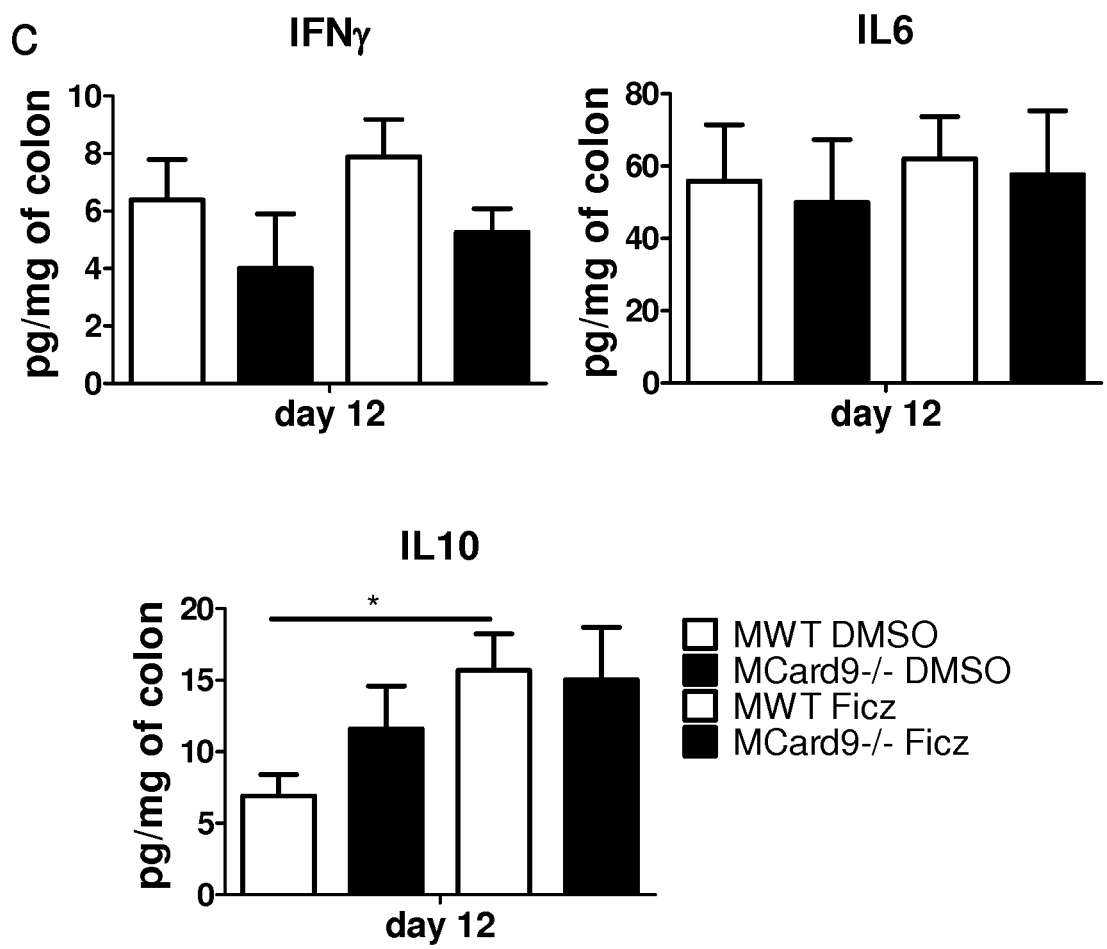
Figure 13 b and c

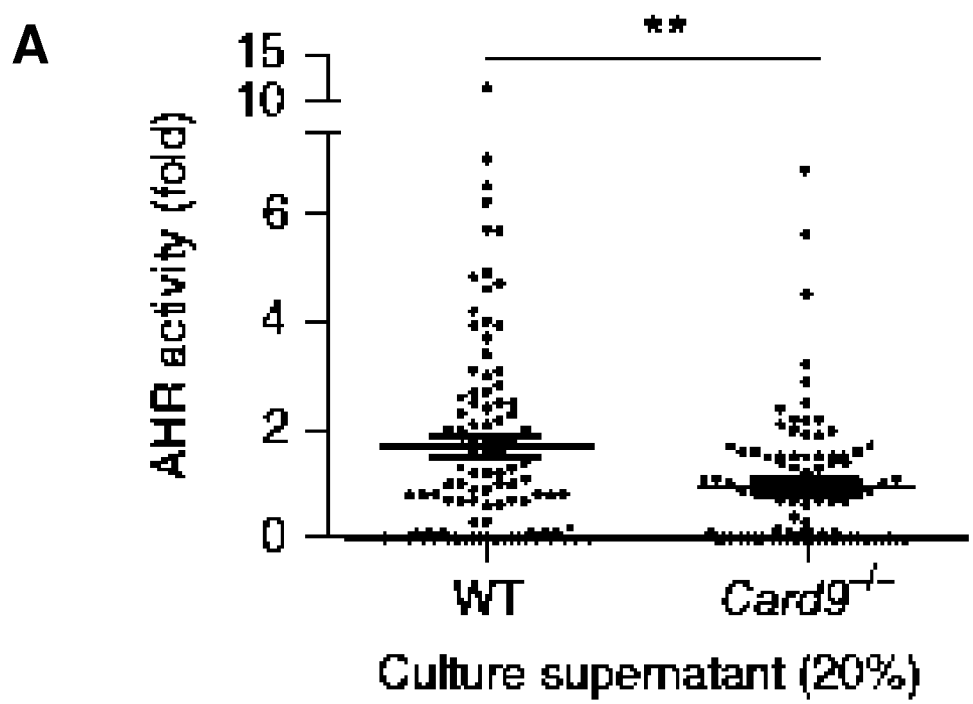
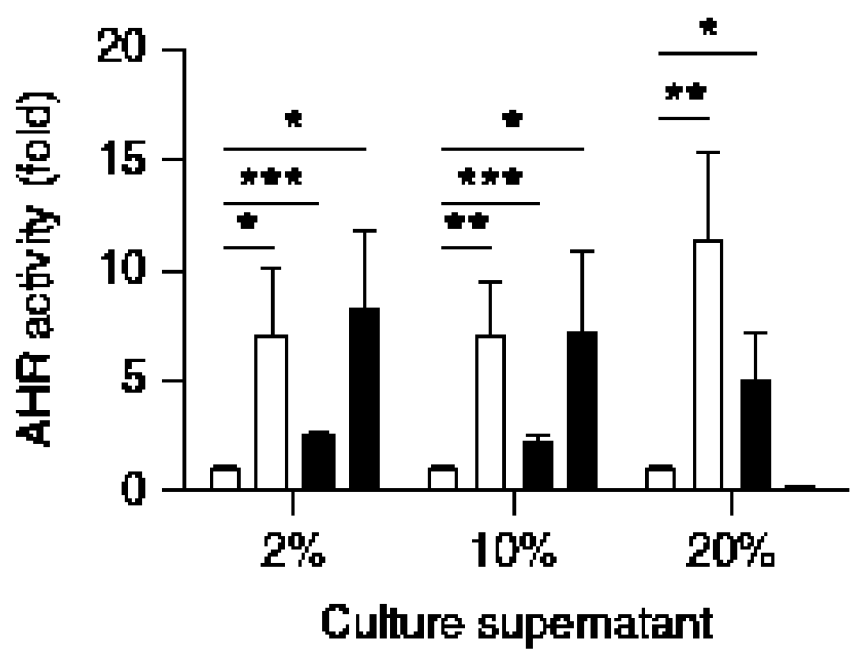
Figure 16

SEQUENCE LISTING

```
<160> NUMBER OF SEQ ID NOS: 13

<210> SEQ ID NO 1
<211> LENGTH: 927
<212> TYPE: DNA
<213> ORGANISM: Lactobacillus taiwanensis

<400> SEQUENCE: 1
gacggctgac tcctataaag gttatcccac cggctttggg tgttacagac tctcatggtg      60
tgacgggcgg tgtgtacaag gcccgggaac gtattcaccg cggcgtgctg atccgcgatt     120
actagcgatt ccagcttcgt gtaggcgagt tgcagcctac agtccgaact gagaacggct     180
ttaagagatc cgcttgcctt cgcaggttcg cttctcgttg taccgtccat tgtagcacgt     240
gtgtagccca ggtcataagg ggcatgatga cttgacgtca tccccacctt cctccggttt     300
gtcaccggca gtctcattag agtgcccaac ttaatgatgg caactaatga caagggttgc     360
gctcgttgcg ggacttaacc caacatctca cgacacgagc tgacgacagc catgcaccac     420
```

| | |
|---|---|
| ctgtctcagc gtccccgaag ggaacaccta atctcttagg tttgcactgg atgtcaagac | 480 |
| ctggtaaggt tcttcgcgtt gcttcgaatt aaaccacatg ctccaccgct tgtgcgggcc | 540 |
| cccgtcaatt cctttgagtt tcaaccttgc ggtcgtactc cccaggcgga gtgcttaatg | 600 |
| cgttagctgc agcactgaga ggcggaaacc tcccaacact tagcactcat cgtttacggc | 660 |
| atggactacc agggtatcta atcctgttcg ctacccatgc tttcgagcct cagcgtcagt | 720 |
| tgcagaccag agagccgcct cgccactggt gttcttcca tatatctacg cattccaccg | 780 |
| ctacacatgg agttccactc tcctcttctg cactcaagtt caacagtttc tgatgcaatt | 840 |
| ctccggttga gccgaaggct ttcacatcag acttattgaa ccgcctgcac tcgctttacg | 900 |
| cccaataaat ccggacaacg cttgcca | 927 |

```
<210> SEQ ID NO 2
<211> LENGTH: 851
<212> TYPE: DNA
<213> ORGANISM: Lactobacillus taiwanensis

<400> SEQUENCE: 2
```

| | |
|---|---|
| tactgcagtc gagcgagctt gcctagatga ttttagtgct tgcactaaat gaaactagat | 60 |
| acaagcgagc ggcggacggg tgagtaacac gtgggtaacc tgcccaagag actgggataa | 120 |
| cacctggaaa cagatgctaa taccggataa caacactaga cgcatgtcta gagtttaaaa | 180 |
| gatggttctg ctatcactct tggatggacc tgcggtgcat tagctagttg gtaaggtaac | 240 |
| ggcttaccaa ggcaatgatg catagccgag ttgagagact gatcggccac attgggactg | 300 |
| agacacggcc caaactcata cgggaggcag cagtagggaa tcttccacaa tggacgcaag | 360 |
| tctgatggag caacgccgcg tgagtgaaga agggtttcgg ctcgtaaagc tctgttggta | 420 |
| gtgaagaaag atagaggtag taactggcct ttatttgacg gtaattaccta gaaaagtcac | 480 |
| ggctaactac gtgccagcag ccgcggtaat acgtaggtgg caagcgttgt ccggatttat | 540 |
| tgggcgtaaa gcgagtgcag gcggttcaat aagtctgatg tgaaagcctt cggctcaacc | 600 |
| ggagaattgc atcagaaact gttgaacttg agtgcagaag aggagagtgg aactccatgt | 660 |
| gtagcggtgg aatgcgtaga tatatggaag aacaccagtg gcgaaggcgg ctctctggtc | 720 |
| tgcaactgac gctgaggctc gaaagcatgg gtagcgaaca ggattagata ccctggtagt | 780 |
| ccatgccgta aacgatgagt gctaagtgtt gggaggtttc cgcctctcag tgctgcagct | 840 |
| aacgcattaa g | 851 |

```
<210> SEQ ID NO 3
<211> LENGTH: 947
<212> TYPE: DNA
<213> ORGANISM: Lactobacillus murinus

<400> SEQUENCE: 3
```

| | |
|---|---|
| gctccaaagg ttaccccacc ggctttgggt gttacaaact ctcatggtgt gacgggcggt | 60 |
| gtgtacaagc cccgggaacg tattcaccgc ggcatgctga tccgcgatta ctagcgattc | 120 |
| cgacttcatg taggcgagtt gcagcctaca atccgaactg agaacggctt taagagattt | 180 |
| gctaaacctc gcggtcttgc gactcgttgt accgtccatt gtagcacgtg tgtagcccag | 240 |
| atcataaggg gcatgatgat ttgacgtcat ccccaccttc ctccggtttg tcaccggcag | 300 |
| tcttgctaga gtgcccaact taatgctggc aactaacaat aagggttgcg ctcgttgcgg | 360 |
| gacttaaccc aacatctcac gacacgagct gacgacaacc atgcaccacc tgtcattttg | 420 |
| tccccgaagg gaaagtccta tctctaggat tgtcaaaaga tgtcaagacc tggtaaggtt | 480 |

```
cttcgcgttg cttcgaatta aaccacatgc tccaccgctt gtgcgggccc ccgtcaattc      540
ctttgagttt caaccttgcg gtcgtactcc ccaggcggaa tgcttattgc gttagctgca      600
gcactgaagg gcggaaaccc tccaacactt agcattcatc gtttacggcg tggactacca      660
gggtatctaa tcctgtttgc tacccacgct ttcgaacctc agcgtcagtt acagaccaga      720
gagccgcttt cgccactggt gttcttccat atatctacgc atttcaccgc tacacatgga      780
gttccactct cctcttctgc actcaagtct cccagtttcc aatgcactac tccggttaag      840
ccgaaggctt tcacatcaga cttaaaagac cgcctgcgtt ccctttacgc ccaataaatc      900
cggataacgc ttgccaccta cgtattaccg cggctgctgg cacgtag                    947

<210> SEQ ID NO 4
<211> LENGTH: 433
<212> TYPE: DNA
<213> ORGANISM: Lactobacillus murinus

<400> SEQUENCE: 4
cgaacgaaac ttctttatca ccgagtgctt gcactcaccg ataaagagtt gagtggcgaa       60
cgggtgagta acacgtgggc aacctgccca aaagaggggg ataacacttg gaaacaggtg      120
ctaataccgc ataaccatag ttaccgcatg gtaactatgt aaaaggtggc tatgctaccg      180
cttttggatg ggcccgcggc gcattagcta gttggtgggg taaaggctta ccaaggcaat      240
gatgcgtagc cgaactgaga ggttgatcgg ccacattggg actgagacac ggcccaaact      300
cctacgggag gcagcagtag ggaatcttcc acaatgggcg aaagcctgat ggagcaacgc      360
cgcgtgggtg aagaaggtct tcggatcgta aaaccctgtt gttagagaag aaagtgcgtg      420
agagtaactt ttc                                                         433

<210> SEQ ID NO 5
<211> LENGTH: 844
<212> TYPE: DNA
<213> ORGANISM: Lactobacillus animalis

<400> SEQUENCE: 5
tggtcgaaag gttaccccac cggctttggg tgttacaaac tctcatggtg tgacgggcgg       60
tgtgtacaag gcccgggaac gtattcaccg cggcatgctg atccgcgatt actagcgatt      120
ccgacttcat gtaggcgagt tgcagcctac aatccgaact gagaacggct ttaagagatt      180
tgctaaacct cgcggtcttg cgactcgttg taccgtccat gtagcacgtg tgtagcccca      240
gatcataagg ggcatgatga tttgacgtca tccccacctt cctccggttt gtcaccggca      300
gtcttgctag agtgcccaac ttaatgctgg caactaacaa taaggggttgc gctcgttgcg      360 ggacttaacc caacatctca cgacacgagc tgacgacaac catgcaccac ctgtcatttt      420
gtccccgaag ggaaagtcct atctctagga ttgtcaaaag atgtcaagac ctggtaaggt      480
tcttcgcgtt gcttcgaatt aaaccacatg ctccaccgct gtgcgggccc ccgtcaatt       540 cctttgagtt tcaaccttgc ggtcgtactc cccaggcgga atgcttattg cgttagctgc      600
agcactgaag gacggaaacc ctccaacact tagcattcat cgtttacggc gtggactacc      660
agggtatcta atcctgtttg ctacccacgc tttcgaacct cagcgtcagt tacagaccag      720
agagccgctt tcgccactgg tgttcttcca tatatctacg catttcaccg ctacacatgg      780
agttccactc tcctcttctg cactcaagtc tcccagtttc caatgcacta ctccggttaa      840
gccg                                                                   844
```

<210> SEQ ID NO 6
<211> LENGTH: 704
<212> TYPE: DNA
<213> ORGANISM: Lactobacillus animalis

<400> SEQUENCE: 6

| | | | | | |
|---|---|---|---|---|---|
| gcgagttgca | gcctacaatc | cgaactgaga | acggctttaa | gagatttgct | aaacctcgcg | 60 |
| gtcttgcgac | tcgttgtacc | gtccattgta | gcacgtgtgt | agcccagatc | ataaggggca | 120 |
| tgatgatttg | acgtcatccc | caccttcctc | cggtttgtca | ccggcagtct | tgctagagtg | 180 |
| cccaacttaa | tgctggcaac | taacaataag | ggttgcgctc | gttgcgggac | ttaacccaac | 240 |
| atctcacgac | acgagctgac | gacaaccatg | caccacctgt | cattttgtcc | ccgaagggaa | 300 |
| agtcctatct | ctaggattgt | caaaagatgt | caagacctgg | taaggttctt | cgcgttgctt | 360 |
| cgaattaaac | cacatgctcc | accgcttgtg | cgggcccccg | tcaattcctt | tgagtttcaa | 420 |
| ccttgcggtc | gtactcccca | ggcggaatgc | ttattgcgtt | agctgcagca | ctgaagggcg | 480 |
| gaaaccctcc | aacacttagc | attcatcgtt | tacggcgtgg | actaccaggg | tatctaatcc | 540 |
| tgtttgctac | ccacgctttc | gaacctcagc | gtcagttaca | gaccagagag | ccgctttcgc | 600 |
| cactggtgtt | cttccatata | tctacgcatt | tcaccgctac | acatggagtt | ccactctcct | 660 |
| cttctgcact | caagtctccc | agtttccaat | gcactactcc | ggtt | | 704 |

<210> SEQ ID NO 7
<211> LENGTH: 365
<212> TYPE: DNA
<213> ORGANISM: Lactobacillus animalis

<400> SEQUENCE: 7

| | | | | | |
|---|---|---|---|---|---|
| aactcatacg | ggaggcagca | gtagggaatc | ttccacaatg | ggcgaaagcc | tgatggagca | 60 |
| acgccgcgtg | ggtgaagaag | gtcttcggat | cgtaaaaccc | tgttgttaga | gaagaaagtg | 120 |
| cgtgagagta | actgttcacg | tttcgacggt | atctaaccag | aaagccacgg | ctaactacgt | 180 |
| gccagcagcc | gcggtaatac | gtaggtggca | agcgttatcc | ggatttattg | ggcgtaaagg | 240 |
| gaacgcaggc | ggtcttttaa | gtctgatgtg | aaagccttcg | gcttaaccgg | agtagtgcat | 300 |
| tggaaactgg | gagacttgag | tgcagaagag | gagagtggaa | ctccatgtgt | agcggtgaaa | 360 |
| tgcgt | | | | | | 365 |

<210> SEQ ID NO 8
<211> LENGTH: 308
<212> TYPE: DNA
<213> ORGANISM: Lactobacillus animalis

<400> SEQUENCE: 8

| | | | | | |
|---|---|---|---|---|---|
| aatactgcag | tcgaacgaaa | cttctttatc | accgagtgct | tgcactcacc | gataaagagt | 60 |
| tgagtggcga | acgggtgagt | aacacgtggg | caacctgccc | aaaagagggg | gataacactt | 120 |
| ggaaacaggt | gctaataccg | cataaccata | gttaccgcat | ggtaactatg | taaaaggtgg | 180 |
| ctatgctacc | gcttttggat | gggcccgcgg | cgcattagct | agttggtggg | gtaaaggctt | 240 |
| accaaggcaa | tgatgcgtag | ccgaactgag | aggttgatcg | gccacattgg | gactgagaca | 300 |
| cggcccaa | | | | | | 308 |

<210> SEQ ID NO 9
<211> LENGTH: 840
<212> TYPE: DNA
<213> ORGANISM: Lactobacillus reuteri

<400> SEQUENCE: 9

```
cacgccgact ttgggcgtta caaactccca tggtgtgacg ggcggtgtgt acaaggcccg      60
ggaacgtatt caccgcggca tgctgatccg cgattactag cgattccgac ttcgtgtagg     120
cgagttgcag cctacagtcc gaactgagaa cggctttaag agattagctt gctctcgcga     180
gttttgcaact cgttgtaccg tccattgtag cacgtgtgta gcccaggtca taagggggcat     240
gatgatctga cgtcgtcccc accttcctcc ggtttgtcac cggcagtctc actagagtgc     300
ccaactcaat gctggcaact agtaacaagg gttgcgctcg ttgcgggact aacccaaca      360
tctcacgaca cgagctgacg acgaccatgc accacctgtc attgcgtccc cgaagggaac     420
gccttatctc taaggttagc gcaagatgtc aagacctggt aaggttcttc gcgtagcttc     480
gaattaaacc acatgctcca ccgcttgtgc gggcccccgt caattccttt gagttttcaac    540
cttgcggtcg tactccccag gcggagtgct taatgcgtta gctccggcac tgaagggcgg     600
aaaccctcca acacctagca ctcatcgttt acggcatgga ctaccagggt atctaatcct    660
gttcgctacc catgctttcg agcctcagcg tcagttgcag accagacagc cgccttcgcc     720
actggtgttc ttccatatat ctacgcattc caccgctaca catggagttc cactgtcctc     780
ttctgcactc aagtcgcccg gtttccgatg cacttcttcg gttaagccga aggctttcac     840
```

<210> SEQ ID NO 10
<211> LENGTH: 355
<212> TYPE: DNA
<213> ORGANISM: Lactobacillus reuteri

<400> SEQUENCE: 10

```
cctacgggag gcagcagtag ggaatcttcc acaatgggcg caagcctgat ggagcaacac      60
cgcgtgagtg aagaagggtt tcggctcgta aagctctgtt gttggagaag aacgtgcgtg    120
agagtaactg ttcatgcagt gacggtatcc aaccagaaag tcacggctaa ctacgtgcca    180
gcagccgcgg taatacgtag gtggcaagcg ttatccggat ttattgggcg taaagcgagc    240
gcaggcggtt gcttaggtct gatgtgaaag ccttcggctt aaccgaagaa gtgcatcgga    300
aaccgggcga cttgagtgca gaagaggaca gtggaactcc atgtgtagcg tggaa         355
```

<210> SEQ ID NO 11
<211> LENGTH: 271
<212> TYPE: DNA
<213> ORGANISM: Lactobacillus reuteri

<400> SEQUENCE: 11

```
atggatcacc agtgagtggc ggacgggtga gtaacacgta ggtaacctgc cccggagcgg      60
gggataacat ttgaaacag atgctaatac cgcataacaa caaaagccgc atggctttta    120
tttgaaagat ggctttggct atcactctgg gatggacctg cggtgcatta gctagttggt     180
aaggtaacgg cttaccaagg cgatgatgca tagccgagtt gagagactga tcggccacaa     240
tggaactgag acacggtcca tactcatacg g                                    271
```

<210> SEQ ID NO 12
<211> LENGTH: 868
<212> TYPE: DNA
<213> ORGANISM: Lactobacillus reuteri

<400> SEQUENCE: 12

```
aacgccgact ttgggcgtta caaactccca tggtgtgacg ggcggtgtgt acaaggcccg      60
```

```
ggaacgtatt caccgcggca tgctgatccg cgattactag cgattccgac ttcgtgtagg    120
cgagttgcag cctacagtcc gaactgagaa cggctttaag agattagctt gctctcgcga    180
gtttgcaact cgttgtaccg tccattgtag cacgtgtgta gcccaggtca taagggcat     240 gatgatctga cgtcgtcccc accttcctcc ggtttgtcac cggcagtctc actagagtgc    300
ccaactcaat gctggcaact agtaacaagg gttgcgctcg ttgcgggact taacccaaca    360
tctcacgaca cgagctgacg acgaccatgc accacctgtc attgcgtccc cgaagggaac    420
gccttatctc taaggttagc gcaagatgtc aagacctggt aaggttcttc gcgtagcttc    480
gaattaaacc acatgctcca ccgcttgtgc gggcccccgt caattccttt gagtttcaac    540
cttgcggtcg tactccccag gcggagtgct taatgcgtta gctccggcac tgaagggcgg    600
aaaccctcca cacctagca ctcatcgttt acggcatgga ctaccagggt atctaatcct     660
gttcgctacc catgctttcg agcctcagcg tcagttgcag accagacagc cgccttcgcc    720
actggtgttc ttccatatat ctacgcattc caccgctaca catggagttc cactgtcctc    780
ttctgcactc aagtcgcccg gtttccgatg cacttcttcg gttaagccga aggctttcac    840
atcagaccta agcaaccgcc tgcgctcg                                        868

<210> SEQ ID NO 13
<211> LENGTH: 702
<212> TYPE: DNA
<213> ORGANISM: Lactobacillus reuteri

<400> SEQUENCE: 13
aagccacatg gcttttattt gaaagatggc tttggctatc actctgggat ggacctgcgg     60
tgcattagct agttggtaag gtaacggctt accaaggcga tgatgcatag ccgagttgag    120
agactgatcg gccacaatgg aactgagaca cggtccatac tcctacggga ggcagcagta    180
gggaatcttc cacaatgggc gcaagcctga tggagcaaca ccgcgtgagt gaagaagggt    240
ttcggctcgt aaagctctgt tgttggagaa gaacgtgcgt gagagtaact gttcatgcag    300
tgacggtatc caaccagaaa gtcacggcta actacgtgcc agcagccgcg gtaatacgta    360
ggtggcaagc gttatccgga tttattgggc gtaaagcgag cgcaggcggt tgcttaggtc    420
tgatgtgaaa gccttcggct taaccgaaga agtgcatcgg aaaccgggcg acttgagtgc    480
agaagaggac agtggaactc catgtgtagc ggtggaatgc gtagatatat ggaagaacac    540
cagtggcgaa ggcggctgtc tggtctgcaa ctgacgctga ggctcgaaag catgggtagc    600
gaacaggatt agataccctg gtagtccatg ccgtaaacga tgagtgctag gtgttggagg    660
gtttccgccc ttcagtgccg gagctaacgc attaagcact cc                        702
```

PHARMACEUTICAL COMPOSITIONS FOR PREVENTING OR TREATING INFLAMMATORY BOWEL DISEASES

CROSS-REFERENCE TO RELATED APPLICATION

This application is the U.S. national stage application of International Patent Application No. PCT/EP2016/069797, filed Aug. 22, 2016.

The Sequence Listing for this application is labeled "Seq-List.txt" which was created on Aug. 22, 2016 and is 13 KB. The entire content of the sequence listing is incorporated herein by reference in its entirety.

FIELD OF THE INVENTION

The present invention relates to methods and pharmaceutical compositions for preventing or treating inflammatory bowel diseases.

BACKGROUND OF THE INVENTION

The microbial community in the human gastrointestinal (GI) tract is a key factor to the health and nutrition of its host (1). Loss of the fragile equilibrium within this complex ecosystem, termed dysbiosis, is involved in numerous pathologies; amongst them are the inflammatory bowel diseases (IBD). IBD incidence rose during the 20th century and will continue to increase substantially, strongly affecting individuals in the most challenging and productive years of life (2). IBD develop at the intersection of genetic predisposition, dysbiosis of the gut microbiota and environmental influences (3).

Caspase recruitment domain 9 (CARD9), one of the numerous IBD susceptibility genes, codes for an adaptor protein integrating signals downstream of pattern recognition receptors. It is particularly involved in response toward fungi via C-type lectins sensing (4,5). Card9 has been shown to mediate colitis recovery via interleukin 22 (IL22) pathway activation and CARD9 knockout (Card9−/−) mice have enhanced susceptibility to colitis and increased load of intestinal fungi (6). Dysbiosis is often seen as an actor of intestinal inflammation via the increase level of pro-inflammatory microorganisms such as Proteobacteria (7). However, the lack of microorganisms with regulatory effects might also enhance inflammation (8,9).

Accordingly, there is a need to develop new drugs that will be suitable for preventing or treating inflammatory bowel diseases (IBD). In this way, it has been suggested that characterization of new compounds for treatment of IBD may be highly desirable.

In the present invention, the inventors used C57BL/6 wild-type (WT), Card9−/− and germ-free (GF) mice to study the role of the intestinal microbiota in the impaired recovery of Card9−/− mice after colitis. The inventors found that CARD9 deletion had a dramatic effect on both bacterial and fungal gut microbiota. Moreover, the transfer of Card9−/− microbiota into WT GF recipient was sufficient to recapitulate the defective IL22 activation as well as the increased sensitivity to colitis observed in Card9−/− mice. This defect was explained by the inability of the Card9−/− microbiota to metabolize tryptophan into aryl hydrocarbon receptor (AhR) ligands. Indeed, recent data suggest that tryptophan catabolites from microbiota have a role in mucosal immune response via AhR (10) which in turns modulates IL22 production, a cytokine with well-known effects on intestinal homeostasis (10,11). In human comparable mechanisms seems involved, since the inventors showed that IBD patients' microbiota exhibit an impaired production of AhR ligands that correlates with Card9 genotype.

There is no disclosure in the art of the use of AhR agonist in the prevention or treatment of IBD with abnormal microbiota exhibiting an impaired production of AhR ligands, nor the use of bacteria exhibiting AhR activation properties in the prevention or treatment of IBD with abnormal microbiota exhibiting an impaired production of AhR ligands.

SUMMARY OF THE INVENTION

The present invention relates to a method of preventing or treating an inflammatory bowel disease (IBD) in a subject in need thereof comprising the step administering the subject with at least one agent selected from the group consisting of AhR agonists, bacterial probiotics with AhR agonist activity, and IL-22 agonist.

The present invention also relates to an orally ingested composition and pharmaceutical composition comprising a bacterial probiotic exhibiting AhR activation properties.

DETAILED DESCRIPTION OF THE INVENTION

The inventors investigated the host-microbiota interactions as they are involved in intestinal homeostasis and diseases. Caspase Recruitment Domain 9 (Card9) is an inflammatory bowel disease (IBD) susceptibility gene coding for an adapter protein for innate immunity toward many microorganisms. Card9 mediates colitis recovery via interleukin 22 pathway activation and Card9−/− mice have enhanced susceptibility to colitis. In the present invention, the inventors show that Card9−/− mice have an altered gut microbiota and that its transfer into wild-type germ-free recipient is sufficient to recapitulate the increased sensitivity to colitis of Card9−/− mice. The inventors demonstrated that Card9−/− microbiota fails metabolizing tryptophan into Aryl hydrocarbon receptor (AhR) ligands, which are major molecules for intestinal homeostasis. The inventors also demonstrated that inoculation with lactobacilli that metabolize tryptophan and produce AHR ligands reduces colitis in an AHR-dependent manner. In human, the inventors surprisingly found that IBD patients' microbiota exhibit an impaired production of AhR ligands that correlates with CARD9 genotype. Together, these findings reveal that host genes have an impact on gut microbiota composition and function which, in return, have major consequences on host physiology.

Accordingly, the present invention relates to a method of preventing or treating an inflammatory bowel disease (IBD) in a subject in need thereof comprising the steps of: i) determining the AhR agonist activity of the microbiota in a feces sample obtained from the subject, ii) comparing the level determined at step i) with a predetermined reference value and iii) administering the subject with at least one agent selected from the group consisting of AhR agonists, bacterial probiotics with AhR agonist activity, and IL-22 agonist when the level determined at step i) is lower than the predetermined reference value.

As used herein, the term "subject" denotes a mammal. Typically, a subject according to the invention refers to any subject (preferably human) afflicted with or susceptible to be afflicted with an inflammatory bowel disease. In a particular embodiment, the term "subject" refers to a subject having Card9 IBD associated SNP such as rs10781499.

The method of the invention may be performed for any type of inflammatory bowel diseases (IBD) such as Crohn's disease, ulcerative colitis and pouchitis. As used herein, the term "inflammatory bowel diseases (IBD)" has its general meaning in the art and refers to a group of inflammatory diseases of the colon and small intestine such as revised in the World Health Organisation Classification K20-K93 (ICD-10) such as Crohn disease (such as granulomatous enteritis; Crohn disease of small intestine; Crohn disease of large intestine; granulomatous and regional Colitis; Crohn disease of colon, large bowel and rectum; Crohn disease of both small and large intestine), Ulcerative colitis (such as Ulcerative (chronic) pancolitis; backwash ileitis; Ulcerative (chronic) proctitis; Ulcerative (chronic) rectosigmoiditis; Inflammatory polyps; Left sided colitis; left hemicolitis) and noninfective gastroenteritis and colitis (Gastroenteritis and colitis due to radiation; Toxic gastroenteritis and colitis; Allergic and dietetic gastroenteritis and colitis; Food hypersensitivity gastroenteritis or colitis; indeterminate colitis; specified noninfective gastroenteritis and colitis such as Collagenous colitis; Eosinophilic gastritis or gastroenteritis; Lymphocytic colitis Microscopic colitis (collagenous colitis or lymphocytic colitis); Noninfective gastroenteritis and colitis such as Diarrhoea; Enteritis; Ileitis; Jejunitis; Sigmoiditis) and postprocedural disorders of digestive system such as pouchitis.

As used herein, the term "AhR" has its general meaning in the art and refers to Aryl hydrocarbon receptor, a transcription factor which is activated by diverse compounds and regulates the expression of xenobiotic metabolism genes. Aryl hydrocarbon receptor (AhR) is a member of the family of basic helix-loop-helix transcription factors, the bHLH-PAS (basic helix-loop-helix/Per-ARNT-Sim) family (Schmidt J V, Bradfield C A. Ah receptor signaling pathways. Annu Rev Cell Dev Biol. 1996; 12:55-89; Safe S, Lee S O, Jin U H. Role of the aryl hydrocarbon receptor in carcinogenesis and potential as a drug target. Toxicol Sci. 2013 September; 135(1):1-16).

The term "AhR activity" has its general meaning in the art and refers to the biological activity associated with the activation of the AhR resulting from its signal transduction cascade, and including any of the downstream biological effects resulting from the binding of the candidate agent to AhR that may be equal or higher than the biological effect resulting from the binding of the AhR to its natural ligands.

Analyzing the AhR activation level may be assessed by any of a wide variety of well-known methods (Lehmann et al., Journal of Biological Chem., 270, 12953-12956 (1995), Kota et al., 2005, He et al., 2011 and Gao et al., 2009).

In one embodiment, the AhR activation level of the microbiota in a feces sample obtained from the subject is assessed by cell-based assays such as described in the example, He et al., 2011 and Gao et al., 2009. The AhR activation level may be assessed by luciferase activity in AhR-responsive recombinant cells such as AhR-responsive recombinant guinea pig (G16L1.1c8), rat (H4L1.1c4), mouse (H1L1.1c2) and human (HG2L6.1c3) cells. The AhR activation level may also be assessed by measuring the ability to stimulate AhR-dependent gene expression using recombinant mouse hepatoma (Hepa1c1c7) cell-based CALUX (H1L1.1c2 and H1L6.1c2) clonal cell lines that contain a stably integrated AhR-/dioxin-responsive element (DRE)-driven firefly luciferase plasmid (pGudLuc1.1 or pGudLuc6.1, respectively) and CAFLUX (H1G1.1c3) clonal cell lines (He et al., 2011). Typically, the AhR expression level is measured by performing the method described in the example.

In one embodiment, the AhR activation level of the microbiota in a feces sample obtained from the subject is assessed by measuring tryptophan metabolism. Accordingly, the AhR activation level may be assessed by measuring Tryptophan (Trp), kynurenine (Kyn) and indoles derivatives indole-3-acetic acid (IAA) concentrations (or other tryptophan metabolites), measuring Kyn/Trp, IAA/Trp and Kyn/IAA concentrations ratios.

In one embodiment, the AhR activation level is assessed using colon samples obtained from the subject by analyzing the expression of AhR target genes (such as interleukins IL-22 and IL-17), measuring IL-17$^+$ and IL-22$^+$ cells number, detecting Card9 IBD associated SNP such as rs10781499, measuring AhR and chaperone proteins heterodimerization, measuring AhR nuclear translocation, or measuring AhR binding to its dimerization partner (AhR nuclear translocator (ARNT)).

As used herein, the "reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the AhR activation levels (obtained according to the method of the invention) with a defined threshold value. In one embodiment of the present invention, the threshold value is derived from the AhR activation level (or ratio, or score) determined in a feces sample derived from one or more subjects having an inflammatory bowel disease (IBD) with abnormal microbiota exhibiting an impaired production of AhR ligands. Furthermore, retrospective measurement of the AhR activation level (or ratio, or scores) in properly banked historical subject samples may be used in establishing these threshold values.

The term "AhR agonist" has its general meaning in the art and refers to a compound that selectively activates the AhR. The term "AhR agonist" refers to natural AhR ligands and any compound that can directly or indirectly stimulate the signal transduction cascade related to the AhR. As used herein, the term "selectively activates" refers to a compound that preferentially binds to and activates AhR with a greater affinity and potency, respectively, than its interaction with the other members of bHLH-PAS transcription factors family. Compounds that prefer AhR, but that may also activate other sub-types, as partial or full agonists are contemplated. Typically, an AhR agonist is a small organic molecule or a peptide.

Tests and assays for determining whether a compound is an AhR agonist are well known by the skilled person in the art such as described in Ji et al., 2015; Furumatsu et al., 2011; WO 2013/171696; WO 2012/015914; U.S. Pat. No. 6,432,692.

In one embodiment of the invention, the agent which is an AhR agonist may be a molecule, or a mixture of agents such botanical extract, that directly interacts with the AhR protein, inducing its dissociation from the chaperone proteins resulting in its translocation into the nucleus and dimerizing with ARNT (AhR nuclear translocator), and leading to changes in target genes transcription to produce a physiological effect.

Agonists of AhR include, but are not limited to indoles derivatives, tryptophan catabolites such as tryptophan catabolites of the microbiota, kynurenine, kynurenic acid, indole-3-aldehyde (IAld), tryptamine, indole 3-acetate, 3-indoxyl sulfate, 6-formylindolo(3,2-b)carbazole (Ficz), 2,3,7, 8-tetrachlorodibenzo-p-dioxin (TCDD), tryptophan derivatives, flavonoids and biphenyls, Card9 agonists or Card9 expression activators and the mixtures thereof.

In one embodiment, the compound which is a AhR agonist may be a selective AhR modulator (SAhRM) such as diindolylmethane (DIM), methyl-substituted diindolylmethanes, dihalo- and dialkylDIM analogs, mexiletine, β-naphthoflavone (βNF) (5,6 benzoflavone (5,6 BZF) and moieties described, for example, in Safe et al., 2002; Safe et al., 2013; Furumatsu et al., 2011; and WO 2012/015914.

An AhR agonist also includes compounds described in WO 2012/015914 such as CB7950998.

An AhR agonist also includes natural extracts or fractions which are activators of the AhR pathway such as 1,4-dihydroxy-2-naphthoic acid (DHNA) and natural AhR Agonists (NAhRAs) disclosed in WO 2013/171696 and WO 2009/093207.

In one embodiment, the agent of the present invention is a bacterial probiotic exhibiting AhR activation properties.

The term "bacterial probiotic" has its general meaning in the art and refers to a useful microorganism that improves the bacterial flora in the gastrointestinal tract and can bring a beneficial action to the host, and a growth-promoting substance therefor. The term "bacterial probiotic" also refers to a bacterium forming the bacterial flora and a substance that promotes the growth of such a bacterium. The term "bacterial probiotic" also refers to a useful microorganism that can bring a beneficial action to a host and substance produced by these microorganisms (microorganism culture). A growth-promoting substance having AhR-activating potency includes a case in which the substance itself has AhR-activating potency and also a case in which the substance itself does not have AhR-activating potency but it promotes growth of a bacterium having AhR-activating potency. The term "bacterial probiotic" also refers to a dead microbial body and a microbial secretory substance. Because of a suitable enteric environment being formed and the action being independent of differences in enteric environment between individuals, the probiotic is preferably a living microbe.

The term "bacterial probiotic exhibiting AhR activation properties" has its general meaning in the art and relates to a probiotic which can activate the AhR. The term "bacterial probiotic exhibiting AhR activation properties" also relates to a probiotic capable of activating the AhR or having AhR activating potency. The term "AhR activation properties" means potency in being able to activate a signaling pathway that is initiated by AhR activation, and may involve any kind of activating mechanism. Therefore, it is not always necessary for a microbial body itself to be an AhR ligand, and for example a secretory substance produced by a microbe may have AhR-activating potency, or the AhR may be activated by a dead microbial body or homogenate thereof. Therefore, when a "microorganism" or "bacterium" is referred to or a specific microbe is referred to in the present invention, they include not only a living microbe but also a dead microbial body or homogenate thereof and a culture of said microbe or a secretory substance. However, it is preferably a microbial body itself such as a living microbe or a dead microbial body or homogenate thereof, and from the viewpoint of being capable of forming bacterial flora in the gastrointestinal tract, it is more preferably a living microbe (US 2013/0302844).

Bacterial probiotics include, but are not limited to bacterium exhibiting naturally AhR activation properties or modified bacterium exhibiting AhR activation properties such as *Allobaculum, Lactobacillus reuteri, Lactobacillus taiwanensis, Lactobacillus johnsonii, Lactobacillus animalis, Lactobacillus murinus*, the genus *Adlercreutzia*, the phylum Actinobacteria, lactic acid bacterium, *Lactobacillus bulgaricus, Streptococcus thermophilus, Bifidobacterium*, Propionic acid bacterium, *Bacteroides, Eubacterium*, anaerobic *Streptococcus, Enterococcus, Lactobacillus delbrueckii* subsp. *Bulgaricus, Escherichia coli*, other intestinal microorganisms and probiotics described for example in US 2013/0302844.

In a further aspect, the present invention provides isolated bacterial probiotics exhibiting AhR activation properties. The inventors identified and isolated bacterial probiotics exhibiting AhR activation properties by performing the method of screening of the invention and characterized said bacterial probiotics based on 16S gene sequence.

In particular, the inventors have deposited five bacterial probiotics at the Collection Nationale de Cultures de Microorganismes (CNCM, Institut Pasteur, 25 rue du Docteur Roux, 75724 Paris Cedex 15, France), in accordance with the terms of Budapest Treaty, on the 30th of September 2015. The deposited bacterial probiotics have CNCM deposit numbers CNCM I-5019 (SB6WTD3, *Lactobacillus taiwanensis*), CNCM I-5020 (SB6WTD4, *Lactobacillus murinus*), CNCM I-5021 (SB6WTD5, *Lactobacillus animalis*), CNCM I-5022 (SB6WTF6, *Lactobacillus reuteri*), and CNCM I-5023 (SB6WTG6, *Lactobacillus reuteri*).

Accordingly, the present invention also relates to a bacterial probiotic exhibiting AhR activation properties selected from the group consisting of bacterial probiotics available under CNCM deposit numbers CNCM I-5019, CNCM I-5020, CNCM I-5021, CNCM I-5022, CNCM I-5023.

In a further aspect, the present invention also relates to an oral composition comprising the bacterial probiotic of the invention.

The term "oral composition" has its general meaning in the art and refers to any composition that can be ingested orally.

Typically, the orally ingested composition of the invention is selected from the group consisting of a beverage or drink composition, a food composition, a feedstuff composition and a pharmaceutical composition.

The amount ingested per day of the probiotic, or orally ingested composition of the present invention is not particularly limited and may be appropriately adjusted according criteria such as age, symptoms, body weight, and intended application. For example, the amount ingested per day as the probiotic is typically 0.01 to $100 \times 10^{11}$ cells/body, preferably 0.1 to $10 \times 10^{11}$ cells/body, and more preferably 0.3 to $5 \times 10^{11}$ cells/body. Furthermore, for example, the amount ingested per day as the probiotic is 0.01 to $100 \times 10^{11}$ cells/60 kg body weight, preferably 0.1 to $10 \times 10^{11}$ cells/60 kg body weight, and more preferably 0.3 to $5 \times 10^{11}$ cells/60 kg body weight.

The content of the probiotic contained in the orally ingested composition of the present invention may be determined as appropriate depending on its application form. Typically, as probiotic dry microbial body it is for example 5 to 50 w/w %, preferably 1 to 75 w/w %, and more preferably 0.1 to 100 w/w % and 1 to 100 w/w %.

In a further aspect, the present invention also relates to a fecal microbiota transplant composition comprising the bacterial probiotic of the invention.

The term "fecal microbiota transplant composition" has its general meaning in the art and refers to any composition that can restore the fecal microbiota.

In a particular embodiment, the fecal microbiota transplant composition is a fresh or frozen stools of a healthy subject not afflicted with IBD.

In one embodiment, the agent of the present invention is an IL-22 agonist or IL-22 polypeptide. IL-22 agonists are well-known in the art as illustrated by WO 2011087986 and WO 2014145016. IL-22 polypeptides are well-known in the art as illustrated by WO 2014/053481 and WO 2014/145016.

The term "IL-22 agonist" has its general meaning in the art and refers to compounds such as IL-22-Fc. The term "IL-22 polypeptide" has its general meaning in the art and includes naturally occurring IL-22 and function conservative variants and modified forms thereof. The IL-22 can be from any source, but typically is a mammalian (e.g., human and non-human primate) IL-22, and more particularly a human IL-22. IL-22 consists of 179 amino acids. Dumoutier et al. reported for the first time the cloning of genes of murine and human IL-22 (Dumoutier, et al., JI, 164:1814-1819, 2000; U.S. Pat. Nos. 6,359,117 and 6,274,710).

In one embodiment, the agent of the present invention is an IL-17 antagonist. IL-17 antagonists are well-known in the art as illustrated by WO 2013/186236, WO 2014/001368, WO 2012/059598, WO 2013/158821, WO 2012/045848.

IL-17 antagonists include but are not limited to ixekizumab, secukinumab and anti-IL-17-receptor antibodies such as brodalumab (Chandrakumar and Yeung, J Cutan Med Surg. 2015 March; 19(2):109-114).

In a further aspect, when the Ahr activity of the microbiota in a feces sample obtained from the subject is lower than the predetermined reference value, the method of the invention comprises the step of administering the subject with at least one agent selected from the group consisting of AhR agonists, bacterial probiotics, IL-17 antagonists and IL-22 polypeptides in combination with anti-IBD therapy.

In a particular embodiment, the method of the invention comprises the step of administering the subject with an agent which is an AhR agonists in combination with anti-IBD therapy.

As used herein the term "anti-IBD therapy" has its general meaning in the art and relates to anti-inflammatory agents such as mesalazine (5-aminosalicylic acid (5-ASA)); anti-inflammatory steroids such as prednisone and immunosuppressive agents such as TNF inhibitors, azathioprine, methotrexate and or 6-mercaptopurine.

In a further aspect, when the AhR activity of the microbiota in a feces sample obtained from the subject is higher than the predetermined reference value, the method of the invention comprises the step of administering the subject with anti-IBD therapy.

A further aspect of the invention relates to a method for monitoring the efficacy of a treatment for an inflammatory bowel disease (IBD) in a subject in need thereof.

Methods of the invention can be applied for monitoring the treatment (e.g., drug agents) of the subject. For example, the effectiveness of an agent to affect the AhR activation level according to the invention can be monitored during treatments of subjects receiving anti-IBD therapy.

Accordingly, the present invention relates to a method for monitoring the treatment an inflammatory bowel disease (IBD) in a subject in need thereof, said method comprising the steps consisting of:
i) determining the AhR activity of the microbiota in a feces sample obtained from the subject by performing the method of the invention,
ii) administering the subject with at least one agent selected from the group consisting of AhR agonists, bacterial probiotics, IL-17 antagonists and IL-22 polypeptides,
iii) determining the AhR activity of the microbiota in a feces sample obtained from the subject,
iv) and comparing the results determined a step i) with the results determined at step iii) wherein a difference between said results is indicative of the effectiveness of the treatment.

In a further aspect, the present invention relates to a method of screening a candidate agent for use as a drug for the prevention or treatment of IBD in a subject in need thereof, wherein the method comprises the steps of:
providing an AhR, providing a cell, tissue sample or organism expressing an AhR,
providing a candidate agent such as small organic molecule, peptide, polypeptide, non-peptide compound, peptide mimetics, metabolically and/or conformationally stabilized peptide analogs, derivatives or pseudo-peptides, probiotics,
measuring the AhR activity,
and selecting positively candidate agents that induce AhR activity.

Measuring the AhR activity may be assessed by any of a wide variety of well-known methods (Lehmann et al., Journal of Biological Chem., 270, 12953-12956 (1995), Kota et al., 2005, He et al., 2011 and Gao et al., 2009).

Tests and assays for screening and determining whether a candidate agent is a AhR agonist are well known in the art (Ji et al., 2015; Furumatsu et al., 2011; Lehmann et al., 1995; Kota et al., 2005; He et al., 2011; Gao et al., 2009; WO 2013/171696; WO 2012/015914; U.S. Pat. No. 6,432,692). In vitro and in vivo assays may be used to assess the potency and selectivity of the candidate agents to induce AhR activity.

Activities of the candidate agents, their ability to bind AhR and their ability to induce similar effects to those of indole derivatives, indole-3-aldehyde (IAld), or 6-formylindolo(3,2-b)carbazole (Ficz) may be tested using isolated cells expressing AhR, AhR-responsive recombinant cells, colonic and small intestine lamina proporia cells expressing AhR, Th17/Th22 cells, γδT cells, NKp46$^+$ ILC cells, group 3 innate lymphoid cells (ILC3s) expressing the AhR, CHO cell line cloned and transfected in a stable manner by the human AhR or other tissues expressing AhR.

Activities of the candidate agents and their ability to bind to the AhR may be assessed by the determination of a Ki on the AhR cloned and transfected in a stable manner into a CHO cell line and measuring the expression of AhR target genes, measuring Trp, Kyn and indoles derivatives (IAA) concentrations, measuring Kyn/Trp, IAA/Trp and Kyn/IAA concentrations ratios, measuring IL-17$^+$ and IL-22$^+$ cells, measuring AhR and chaperone proteins heterodimerization, measuring AhR nuclear translocation, or measuring AhR binding to its dimerization partner (AhR nuclear translocator (ARNT)) in the present or absence of the candidate agent.

Cells, intestine cells and other tissues expressing another receptor than AhR may be used to assess selectivity of the candidate agents.

The agents of the invention may be used or prepared in a pharmaceutical composition.

In one embodiment, the invention relates to a pharmaceutical composition comprising the agent of the invention and a pharmaceutical acceptable carrier for use in the prevention and treatment of inflammatory bowel diseases (IBD) in a subject of need thereof.

Typically, the agent of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising agents of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active agents in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the agents of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further agent which is used in the prevention or treatment of inflammatory bowel diseases (IBD). For example, the anti-IBD therapy may include anti-inflammatory agents such as mesalazine (5-aminosalicylic acid (5-ASA)); anti-inflammatory steroids such as prednisone and immunosuppressive agents such as TNF inhibitors, azathioprine, methotrexate and or 6-mercaptopurine.

In one embodiment, said additional active agents may be contained in the same composition or administrated separately.

In another embodiment, the pharmaceutical composition of the invention relates to combined preparation for simultaneous, separate or sequential use in the prevention and treatment of inflammatory bowel disease (IBD) in a subject in need thereof.

The invention also provides kits comprising the agent of the invention. Kits containing the agent of the invention find use in therapeutic methods.

The invention will be further illustrated by the following figures and examples. However, these examples and figures should not be interpreted in any way as limiting the scope of the present invention.

FIGURES

Figure 1:
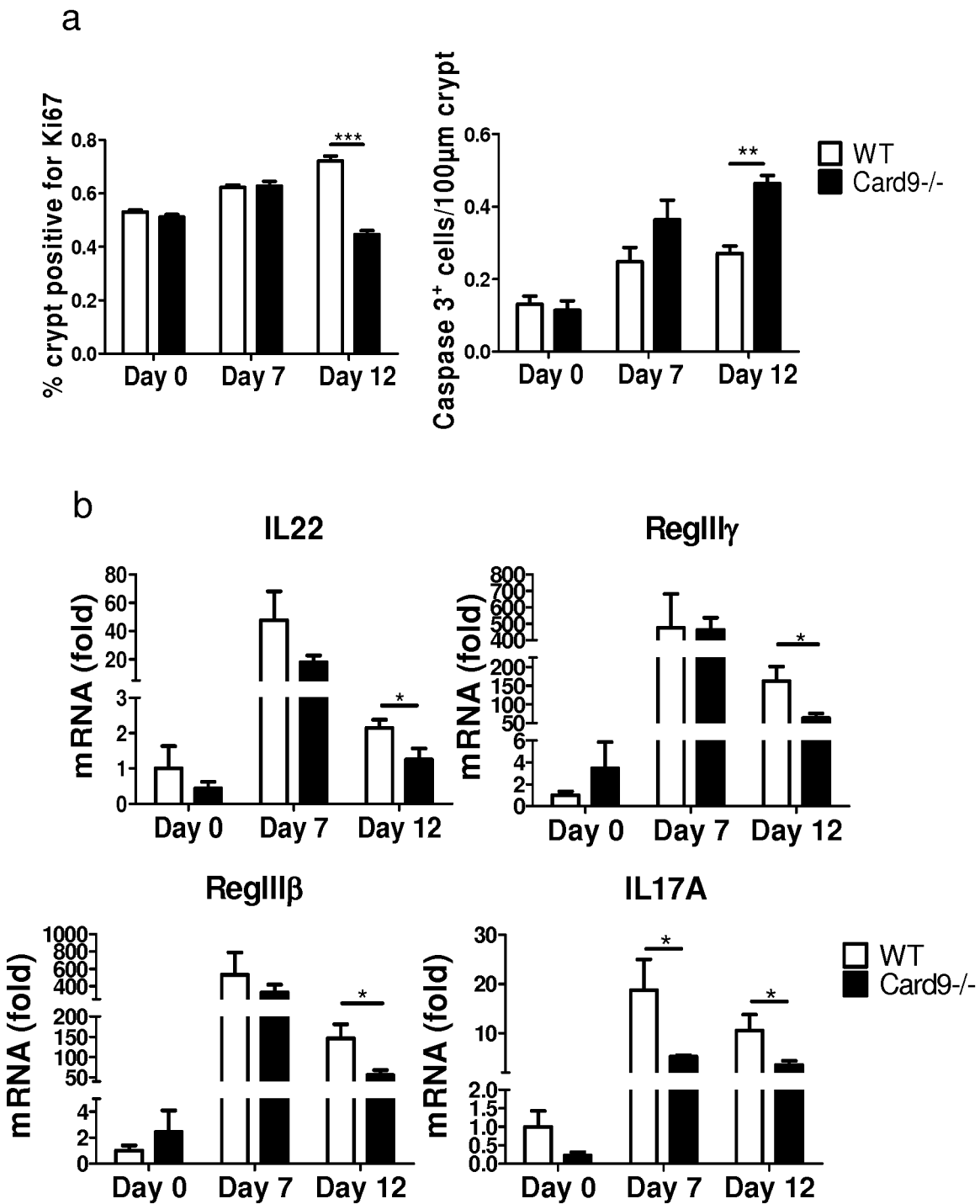

FIG. 1: Card9 is involved in recovery from colitis. a, Quantification of Ki67 and cleaved caspase 3 in the proximal colon (mean±s.e.m.). b, Il22, RegIIIγ, RegIIIβ, and Il17A transcript expression in the colon (day 0, n=3; day 7, n=5; and day 12, n=10; mean±s.e.m.). In all panels, *P<0.05, P<0.001, and *P<0.0001, two-tailed Student's t-test.

Figure 2:
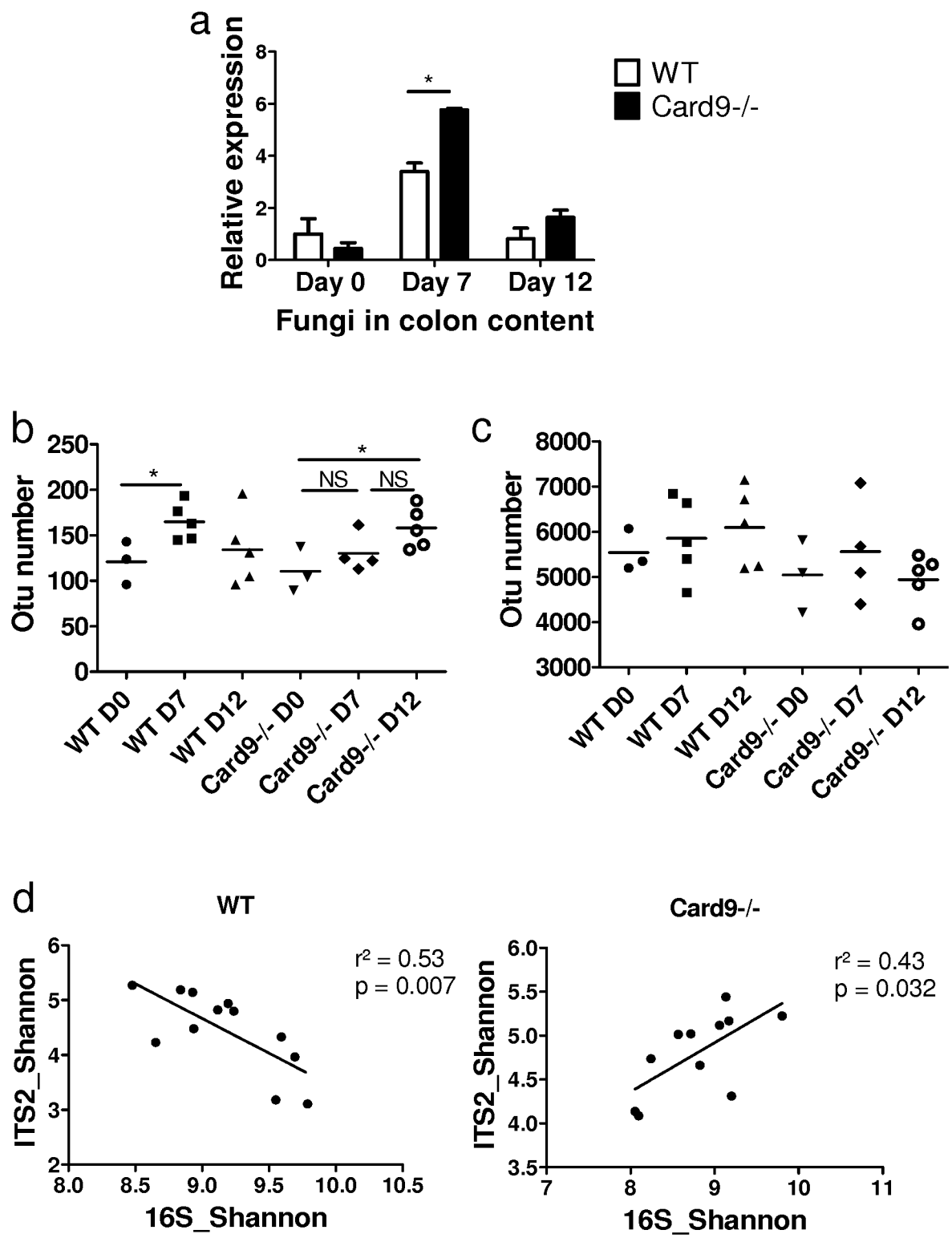

FIG. 2: Card9$^{-/-}$ mice exhibit abnormal bacterial and fungal microbiota. a, Fungal levels in the fecal microbiota were quantified using 18S qRT-PCR and normalized to the bacterial population (mean±s.e.m.). b, Fungal diversity based on the operational taxonomic unit (OTU) number in the fecal samples of WT and Card9$^{-/-}$ mice (mean±s.e.m.). c, Bacterial diversity based on the OTU number in the fecal samples (mean±s.e.m.). d, Correlation between ITS2 and 16S Shannon diversity index in the fecal samples from DSS-treated mice. In all panels, *P<0.05, two-tailed Student's t-test; numbers of mice per experiment are n=3 (day 0) and n=5 (days 7 and 12).

Figure 3:
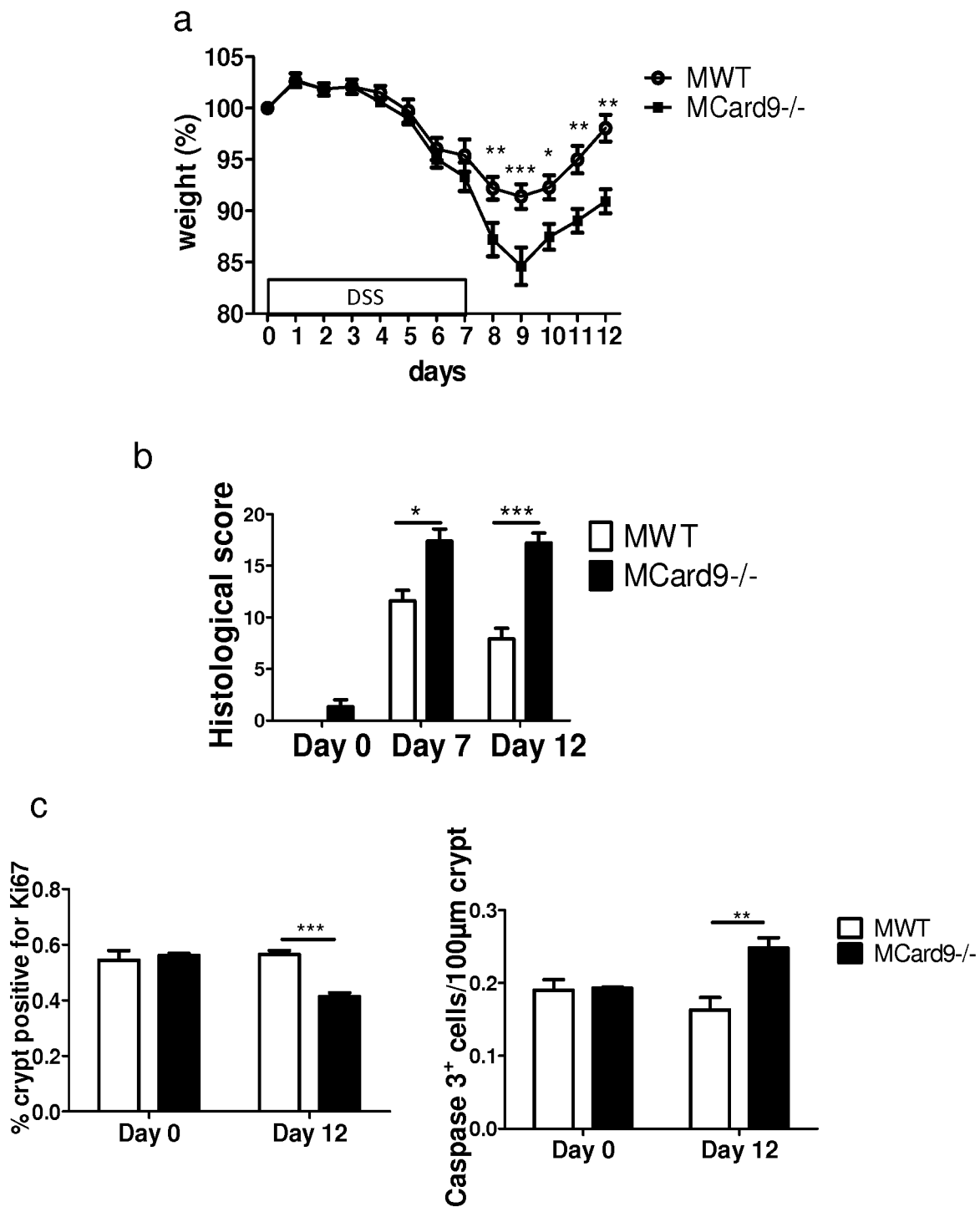

FIG. 3: The microbiota from Card9$^{-/-}$ mice exerts proinflammatory effects. a, Weight loss in the DSS-exposed germ-free WT mice colonized with the WT mouse microbiota (MWT) or the Card9$^{-/-}$ mouse microbiota (MCard9$^{-/-}$; n=23); mean±s.e.m. of four experiments. b, Hematoxylin and eosin staining of proximal colon cross-sections (scale bar, 200 μm) and mouse histological scores; mean±s.e.m. c, Quantification of Ki67 and cleaved caspase 3 in the proximal colon (mean±s.e.m.). In all panels, *P<0.05, P<0.001, and *P<0.0001, two-tailed Student's t-test. In panels b and c, the numbers of mice per experiment are n=5 (days 0 and 7) and n=10 (day 12).

FIG. 4: The IL22 pathway is impaired in germ-free WT mice colonized with gut microbiota from Card9$^{-/-}$ mice. a, Il22, RegIIIγ, RegIIIβ, and Il17A transcript expression in the colon (mean±s.e.m.). b, Cytokine secretion in MLN cells (mean±s.e.m.). c, Cytokines secreted by colon explants cultured for 24 h (mean±s.e.m.). ND, not detected. d, Quantification of IL17$^+$ and IL22$^+$ cells isolated from the colon lamina propria of MWT and MCard9$^{-/-}$ mice on day 12. Cells are gated on CD3$^+$CD4$^+$ (for Th22 and Th17), CD3$^-$CD4$^-$NKp46$^+$ (for NKp46$^+$ ILC), and CD3$^-$CD4$^+$NKp46$^-$ (for LTi) (n=5). In all panels, *P<0.05 and **P<0.001, two-tailed Student's t-test in panels b, c and d, Mann Whitney test in panel a. In panels a, b, and c, the numbers of mice per experiment are n=5 (days 0 and 7) and n=9 (day 12) for MWT and n=10 (day 12) for MCard9$^{-/-}$.

FIG. 5: The gut microbiota of Card9$^{-/-}$ mice exhibits impaired tryptophan metabolism, leading to defective AhR activation and colitis recovery. a, Tryptophan, kynurenine, and indole-3-acetic acid (IAA) concentrations in the feces of WT mice, germ-free WT mice, Ido1$^{-/-}$ mice, and germ-free WT mice colonized with either WT microbiota (MWT) or Card9$^{-/-}$ microbiota (MCard9$^{-/-}$; n=5; mean±s.e.m.). b, Quantification of AhR activation of the feces from indicated mice (mean±s.e.m; n=12 for WT, MWT, and MCard9$^{-/-}$; n=5 for all other groups). NS, no stimulated. c, Weight loss in the DSS-exposed mice. Indicated mice were treated with DMSO or 6-formylindolo(3,2-b)carbazole (Ficz); mean±s.e.m.; For statistical comparisons, †NWT DMSO vs. MCard9$^{-/-}$ DMSO; *MCard9$^{-/-}$ DMSO vs. MCard9$^{-/-}$ Ficz. d, Histological scores and colon length (mean±s.e.m.) from indicated mice. e, Il22, RegIIIγ, RegIIIβ, and Il17A transcript expression in colon (mean±s.e.m.). f, Cytokines secreted by colon explants cultured for 24 h (mean±s.e.m). In all panels, *P<0.05,  or ††P<0.001, and * or †††P<0.0001, two-tailed Student's t-test in panels c, d, e, and f, Mann Whitney test in panels a and b. In panels c, d, e, and f, the number of mice per experiments are MWT DMSO, n=11; MCard9$^{-/-}$ DMSO, n=12; MWT Ficz, n=9; MCard9$^{-/-}$ Ficz, n=6.

Figure 6:
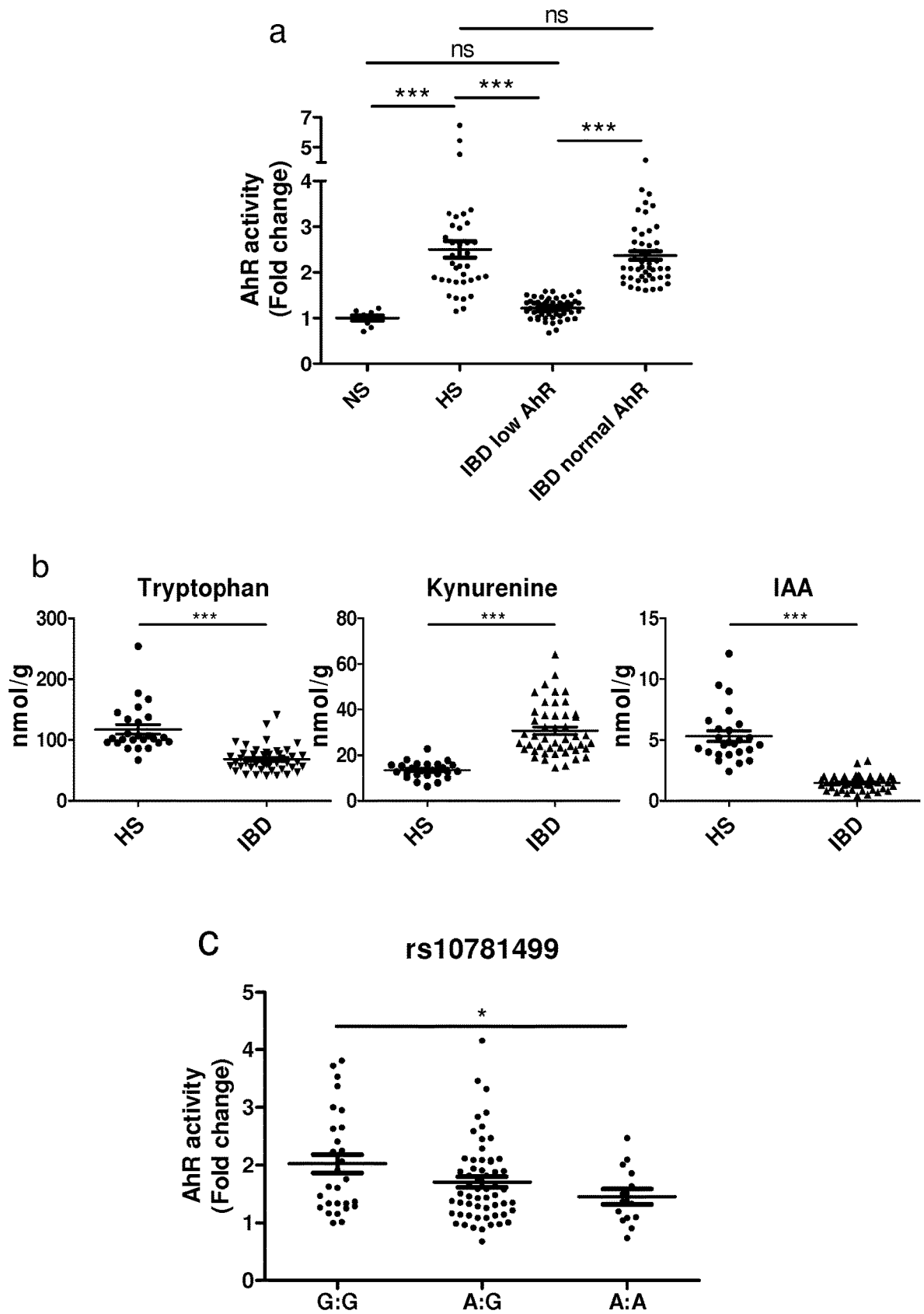

FIG. 6: The gut microbiota of IBD patients exhibits impaired tryptophan metabolism with defective AhR activation that correlates with CARD9 genotype. a, Quantification of AhR activation from the feces of healthy subjects (HS) and IBD patients in remission (mean±s.e.m.). NS, no stimulated; TCDD, 2,3,7,8-tetrachlorodibenzo-p-dioxin. b, Tryptophan, kynurenine, and indole-3-acetic acid (IAA) concentrations in the feces of HS and IBD patients in remission (mean±s.e.m). c, Quantification of AhR activation from the feces of HS and IBD patients in remission, according to SNPs rs10781499. In all panels, *P<0.05, P<0.001, and *P<0.0001, Mann Whitney test. In panels a and b, n=32 for HS and n=54 for IBD patients in remission, and for panel c, n=41 patients.

Figure 7:
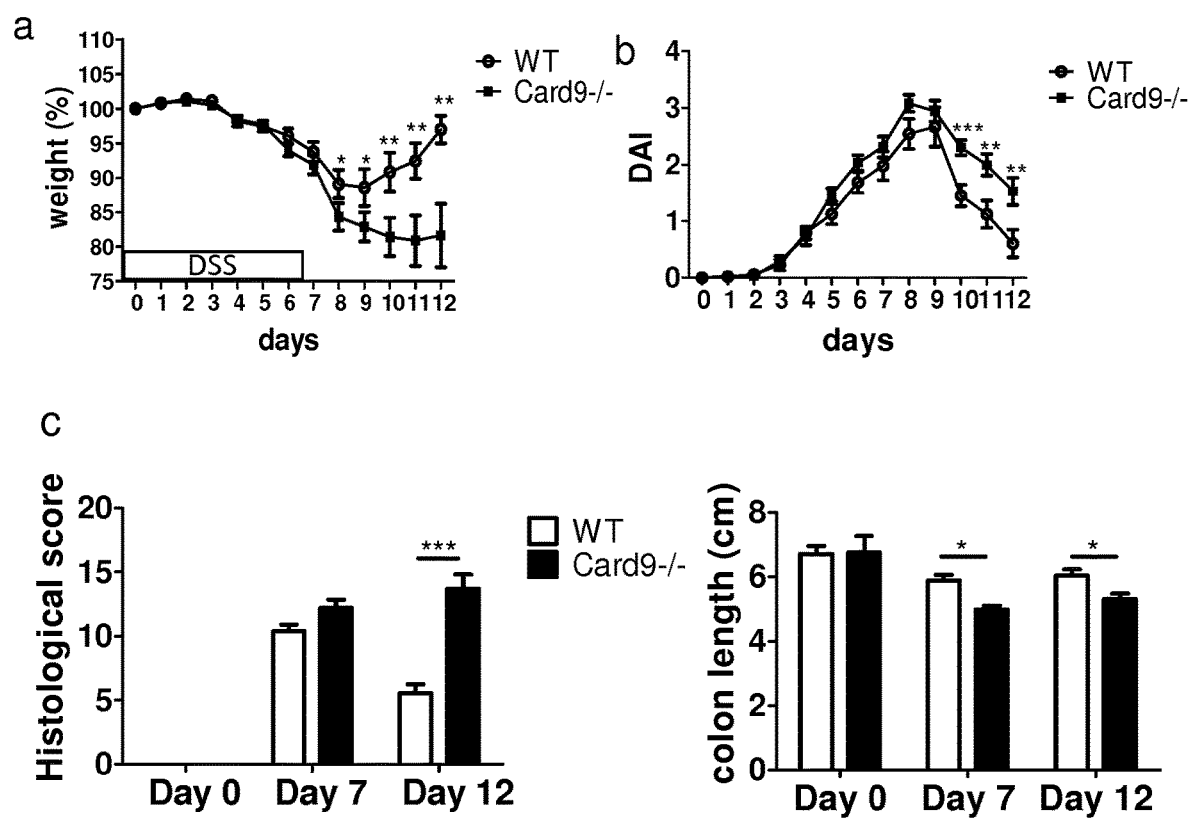

FIG. 7: Card9$^{-/-}$ mice show impaired recovery and deregulated host transcriptomic response. a, Weight loss in DSS-exposed mice (n=15); mean±s.e.m. of three experiments. b, Disease activity index (DAI) of DSS-exposed mice (n=15 mice). Mean±s.e.m. of three experiments. c, Histologic score and colon length of WT and Card9$^{-/-}$ mice before (day 0, n=3) and after (day 7, n=5; day 12, n=10) administration of DSS (means±s.e.m). In all panels, *P<0.05, P<0.001, *P<0.0001, two-tailed Student's t-test.

FIG. 8: Fungal and bacterial microbiota are altered in Card9$^{-/-}$ mice. a, 16S/ITS2 ratios of OTU number in fecal samples (means±s.e.m). In all panels *P<0.05, two-tailed Student's t-test; number of mice per experiments, day 0, n=3; day 7 and 12, n=5.

FIG. 9: Microbiota of Card9$^{-/-}$ mice induce impaired recovery and deregulated host transcriptomic response independent of fungal microbiota. a, Disease activity index (DAI) of DSS-exposed germ-free WT mice colonized with WT microbiota (MWT) or Card9$^{-/-}$ microbiota (MCard9$^{-/-}$) (n=23). Mean±s.e.m. of four experiments. b, Fungi levels in inoculums and fecal microbiota quantified by 18S qRT-PCR and normalized to the bacterial population (means±s.e.m) (n=3 for inoculums and n=15 for fecal microbiota). c, Experimental design. d, Weight loss and DAI of DSS-exposed MWT and MCard9$^{-/-}$ mice. Indicated mice were treated with an antifungal (AF) (fluconazole) (n=5). Mean±s.e.m. Statistical analysis symbols †: for MWT+AF vs MCard9-/-+AF; * for MWT vs MCard9-/-. In all panels, *or †P<0.05;  or ††P<0.001; *P<0.0001, two-tailed Student's t-test in panels a, b, and d.

Figure 10:
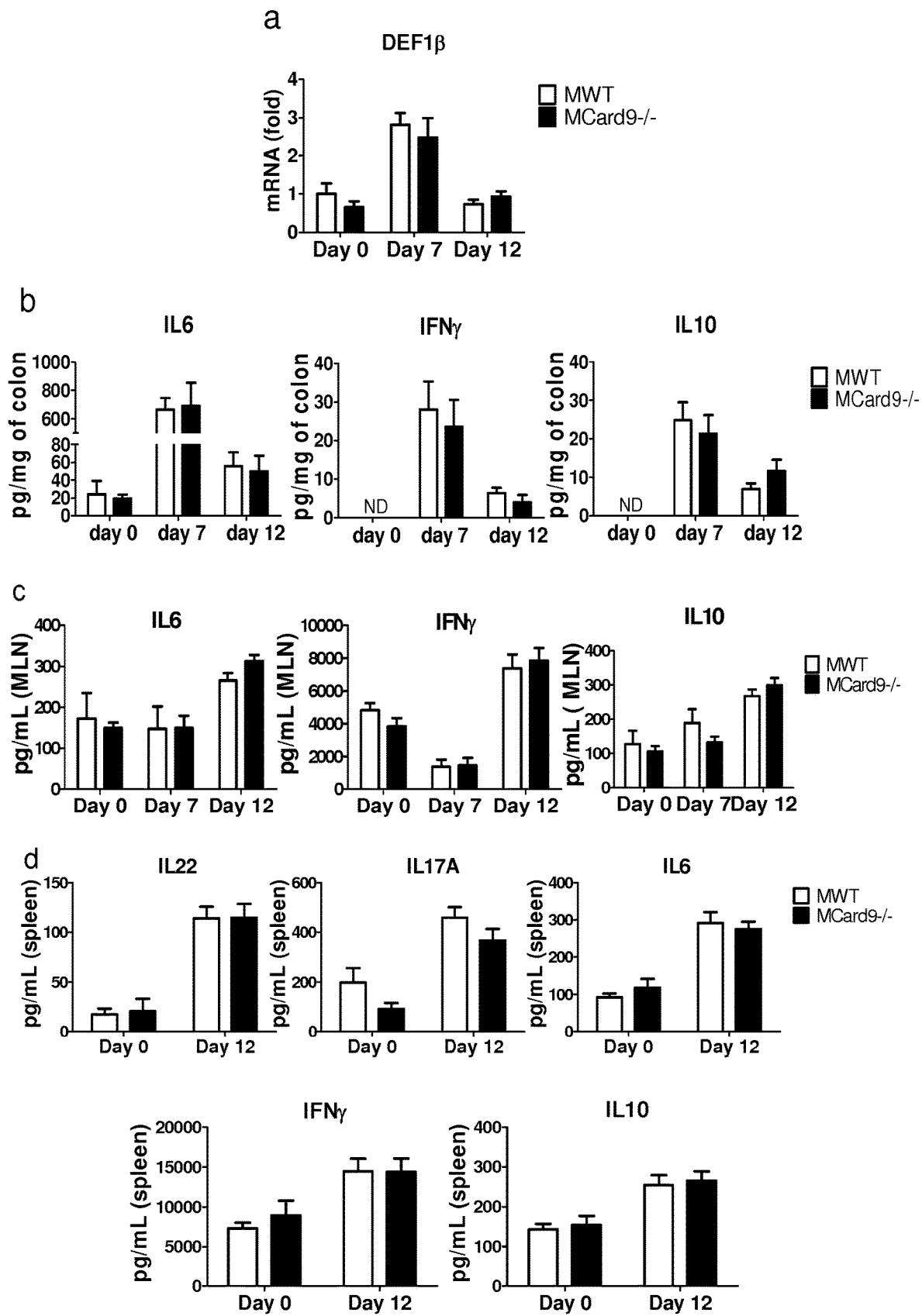

FIG. 10: Colonic Def/3l expression and cytokine production in colon, MLNs, and spleen from MWT and MCard9$^{-/-}$ mice. a, Defβ1 transcript expression in colon of germ-free WT mice colonized with WT microbiota (MWT) or Card9$^{-/-}$ microbiota (MCard9$^{-/-}$) (means±s.e.m.). b, Cytokines secreted by colon explants cultured for 24 h (means±s.e.m). ND, not detected. c, Cytokine secretion in MLN cells (means±s.e.m). d, Cytokine secretion in spleen cells (means±s.e.m). In all panels *P<0.05, Mann Whitney test in panel a, two-tailed Student's t-test in panels b, c and d. Numbers of mice per experiments in all panels: day 0 and 7, n=5; day 12, n=9 for MWT and n=10 for MCard9$^{-/-}$.

Figure 11:
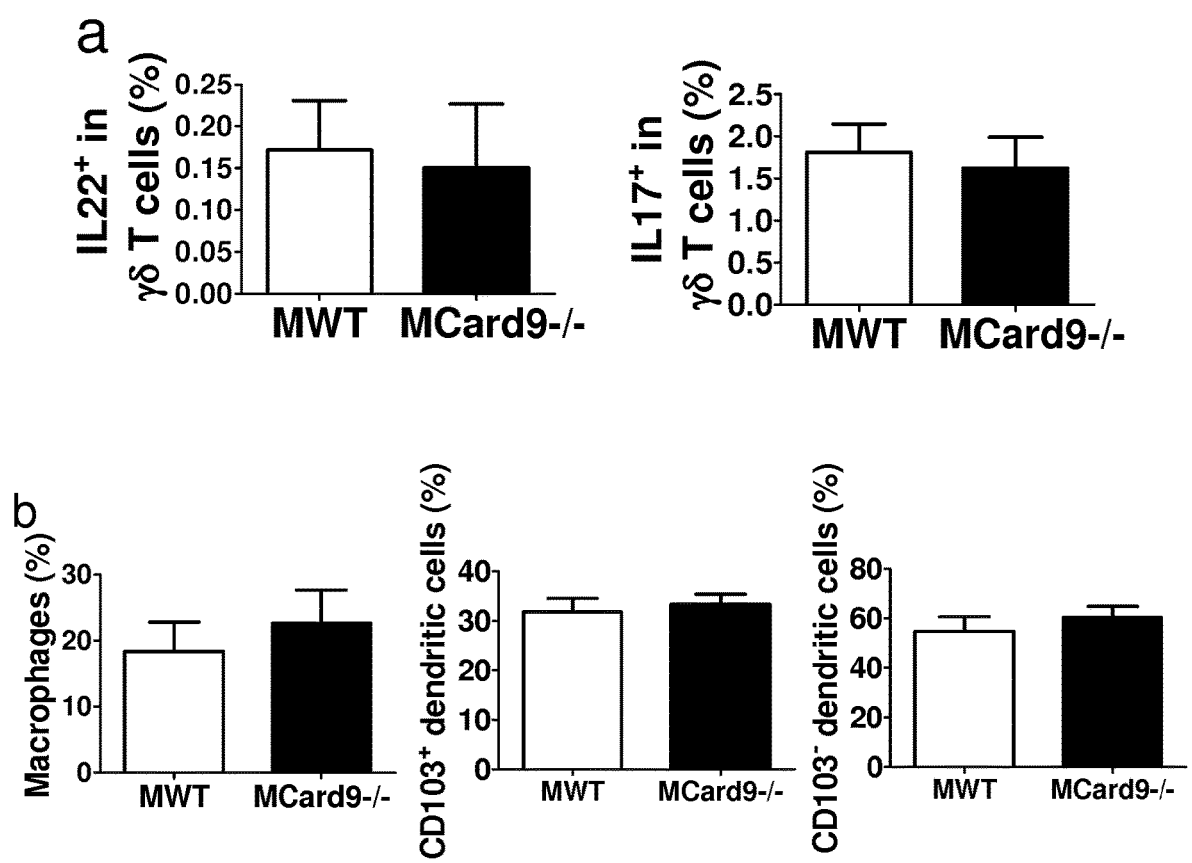

FIG. 11: Quantification of IL17$^+$ and IL22$^+$ cells and antigen-presenting cells isolated from the intestinal lamina propria. a, Representative flow cytometry quantification of IL17$^+$ and IL22$^+$ cells isolated from the small intestine lamina propria of MWT and MCard9$^{-/-}$ mice at day 12 and stimulated with PMA and ionomycin. Cells are gated on CD3$^+$CD4$^-$ TCRγδ$^+$ (for γδ T cells) (n=5). Numbers in the quadrants represent percent cells in each (means±s.e.m). b, Representative quantification of cells isolated from the colon intestine lamina propria of MWT and MCard9$^{-/-}$ mice at day 12. Cells are gated on MCHII$^+$F4/80$^+$CD103$^-$ CD11b$^+$CD11c$^-$ for macrophages and MCHII$^+$F4/80$^-$CD103$^{+/-}$CD11b$^-$CD11c$^+$ for dendritic cells (n=5). Numbers in the quadrants represent percent cells in each (means±s.e.m). In all panels *P<0.05, two-tailed Student's t-test.

FIG. 12: Card9$^{-/-}$ mice and MCard9$^{-/-}$ microbiota exhibit altered tryptophan metabolism. a, The tryptophan metabolic pathway. Host and microbiota metabolites with AhR agonistic activity are in green and red, respectively. b, Quantification of AhR activation using different concentrations of indole-3-acetic acid (IAA) (means±s.e.m) (n=3). c, Kynurenine (Kyn)/tryptophan (Trp), IAA/Trp and Kyn/IAA concentration ratios in feces of WT mice, germ-free WT mice, Ido1$^{-/-}$ mice, and germ-free WT mice colonized with WT microbiota (MWT) or Card9$^{-/-}$ microbiota (MCard9$^{-/-}$) (n=5, means±s.e.m.). d, Trp, Kyn, and IAA concentrations and Kyn/Trp, IAA/Trp and Kyn/IAA concentrations ratios in feces of WT mice, germ-free WT mice, Ido1$^{-/-}$ mice, and Card9$^{-/-}$ mice (n=5, means±s.e.m.). e, Bacteria levels quantified by 16S qRT-PCR in fecal DNA extracted from MWT and MCard9-/- mice and diluted at 1:500 (means±s.e.m) (n=15). NS, no significant. In all panels, *P<0.05; **P<0.001, Mann Whitney test in panels c and d, two-tailed Student's t-test in panel e.

FIG. 13: Card9$^{-/-}$ microbiota exhibits impaired tryptophan metabolism leading to defective AhR activation. a, Quantification of AhR activation of bacterial supernatant. Fold change compared to culture media (means±s.e.m) (n=3). b, Quantification of AhR activation using feces from indicated mice (means±s.e.m) (n=12 for WT mice, n=8 for Card9$^{-/-}$ mice, n=5 for all other groups). NS, no stimulated c, Cytokines secreted by colon explants cultured for 24 h (mean±s.e.m.) (MWT DMSO, n=11; MCard9$^{-/-}$ DMSO, n=12; MWT Ficz, n=9; MCard9$^{-/-}$ Ficz, n=6). In all panels *P<0.05, P<0.001, *P<0.0001, Mann Whitney test in panel b, two-tailed Student's t-test in panels a and c.

Figure 14:
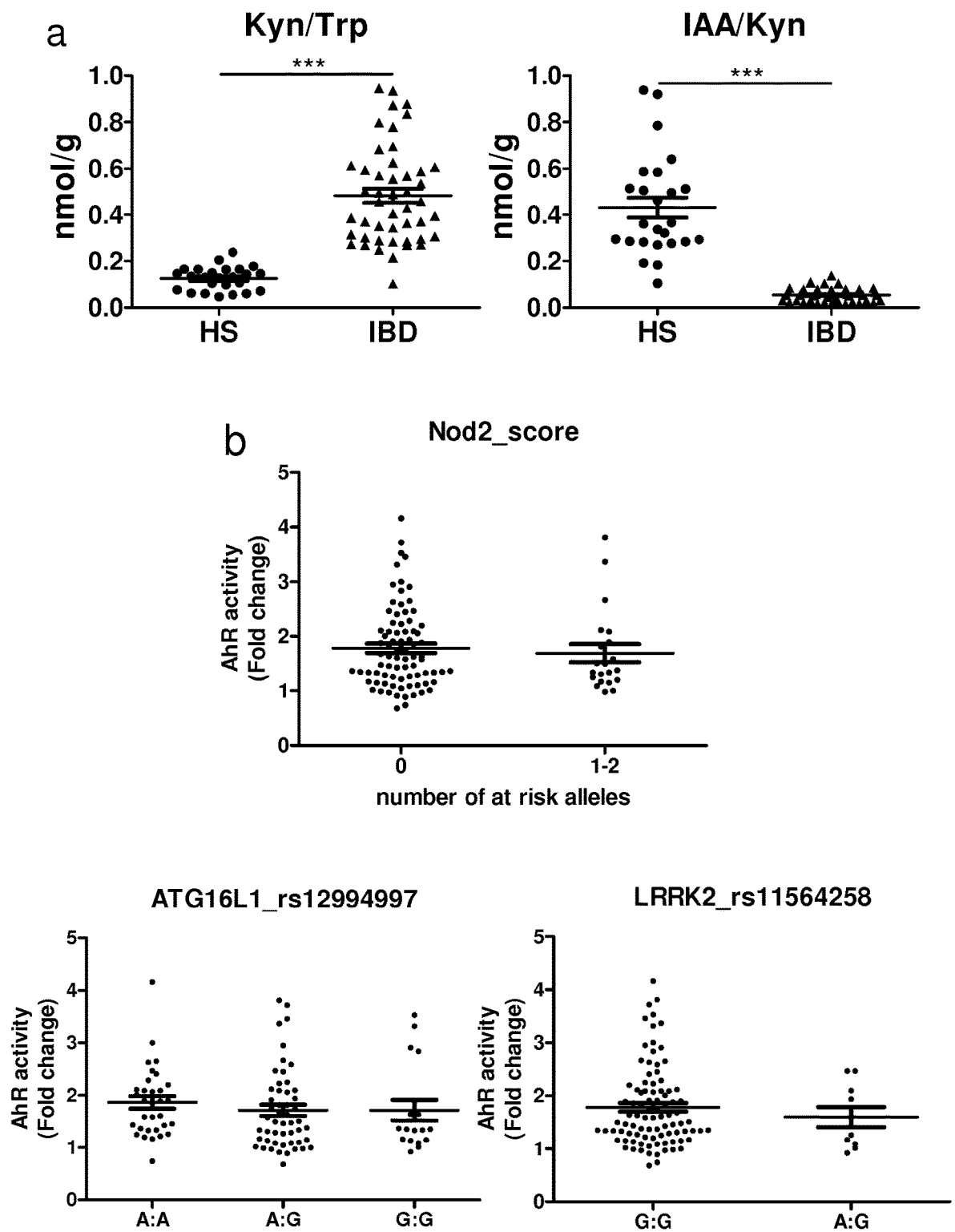

FIG. 14: Impaired tryptophan metabolism in gut microbiota of IBD patients with CARD9 SNPs. a, Kynurenine (Kyn)/tryptophan (Trp) and indole-3-acetic acid (IAA)/Kyn concentration ratios in feces of healthy subjects (HS) and IBD patients in remission. b, Quantification of AhR activation using feces from HS and IBD patients in remission by SNPs rs2066847, rs2066845, and rs2066844 (NOD2), rs12994997 (ATG16L1), and rs11564258 (LRRK2). In all panels ***P<0.0001, Mann Whitney test. In panel a, n=32 for HS and n=54 for IBD patients in remission; in panel b, n=43 patients for NOD2 and n=41 patients for ATG16L1 and LRRK2.

Figure 15:
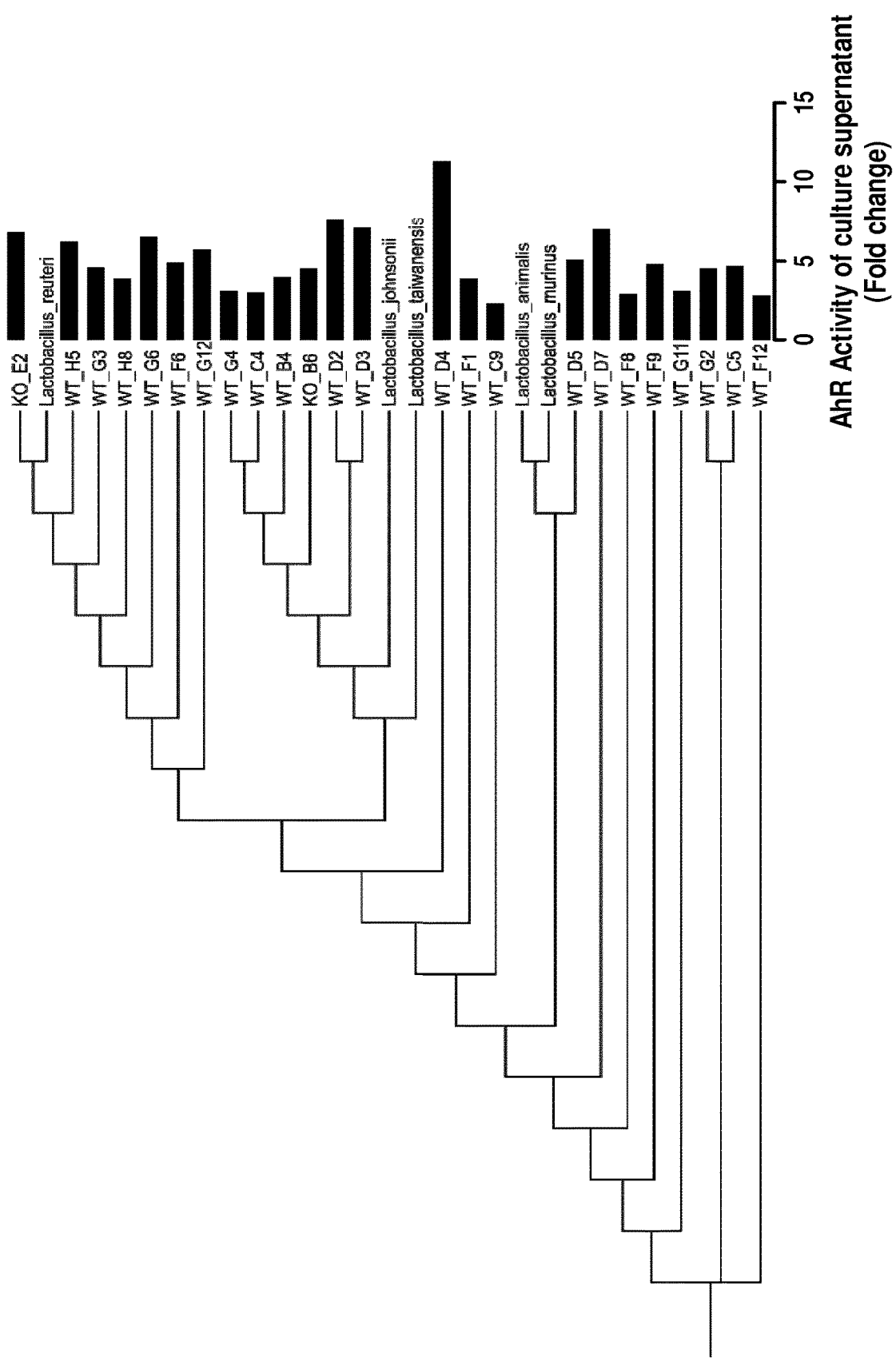

FIG. 15: Bacterial strains with the highest AhR activity were selected and identified based on 16S gene sequence. Sequences were aligned using ClustalX 2.1 and phylogenetic tree was built with FigTree v1.4.2. Sequences of *Lactobacillus reuteri, L. johnsonii, L. taiwanensin, L. animalis* and *L. murinus* were included in the alignment and tree.

FIG. 16: (A) AHR activation by culture supernatants from strains isolated from the feces of WT and Card9/mice, relative to that by culture medium (n=3 replicates for each strain). (B) AHR activation by culture supernatants from *L. murinus* CNCM I-5020, *L. reuteri* CNCM I-5022, and *L. taiwanensis* CNCM I-5019 that were isolated from feces of WT mice, relative to that by culture medium alone (n=3 replicates for each strain). Throughout, data are mean±s.e.m. *P<0.05; P<0.01; *P<0.001, by MannWhitney U-test (A) and two-tailed Student's t-test (B).

EXAMPLES

Example 1

Material & Methods
Animals

Card9-deficient mice (Card9$^{-/-}$) on the C57BL/6J background were provided by Ramnik Xavier (Boston, Mass., USA) and have been described previously[36]. After rederivation in Charles River Laboratories, the animals were housed under specific pathogen-free conditions at the Saint-Antoine Research Center. Heterozygous mice (Card9$^{+/-}$) were used as breeders. At weaning, the mice were separated according to genotype. Germ-free C57BL/6J mice were bred in germ-free isolators at the CDTA (Transgenese et Archivage Animaux Modeles, CNRS, UPS44, Orléans, France). Conventional mice were fed a standard chow diet (R03, SAFE, Augy, France), and germ-free mice were fed a diet without yeast (R04, SAFE, Augy, France). Ido1$^{-/-}$ mice were provided by Soraya Taleb (Inserm Unit 970, Paris, France). Animal experiments were performed according to the institutional guidelines approved by the local ethics committee of the French authorities.

Gut Microbiota Transfer

Fresh stool samples from WT or Card9$^{-/-}$ mice were immediately transferred to an anaerobic chamber, in which the stool samples were suspended and diluted 1:100 in LYHBHI medium (BD Difco, Le Pont De Claix, France) supplemented with cellobiose (1 mg/ml; Sigma-Aldrich, St. Louis, Mo., USA), maltose (1 mg/ml; Sigma-Aldrich), and cysteine (0.5 mg/ml; Sigma-Aldrich). Four- to five-week-old WT germ-free mice were randomly assigned to two groups and inoculated via oral gavage with 400 µl of fecal suspension from the conventional wild-type (MWT) or Card9$^{-/-}$ (MCard9$^{-/-}$) mice and maintained in separated isolators. One aliquot of each fecal suspension was stored at −80° C. All experiments in MWT and MCard9$^{-/-}$ mice were performed three weeks after inoculation.

Induction of DSS Colitis, Ficz Injection, and Antifungal Treatment

To induce colitis, the mice were administered drinking water supplemented with 2% (w/v) dextran sulfate sodium (DSS; MP Biomedicals, LLC, Aurora, Ohio, USA) for 7 days, and then allowed to recover by drinking unsupplemented water for the next 5 days (FIG. 7 a). 6-formylindolo[3,2-b]carbazole (Ficz) was obtained from Enzo Life Sciences (Lausen, Switzerland) resuspended in dimethyl sulfoxide (DMSO; Sigma-Aldrich) and was administered intraperitoneally 1 day after DSS administration (1 μg/mouse). Controls consisted of mice injected with DMSO vehicle alone. For the antifungal treatment, mice were fed 0.5 mg/ml fluconazole in the drinking water (Sigma-Aldrich) 1 week before DSS administration and every day thereafter, as previously described[18]. Body weight, gross blood, and stool consistency were analyzed daily. The severity of colitis was assessed using the disease activity index (DAI) as previously described (6).

Quantification of Cytokines

MLNs and spleens were sieved through a 70-μm cell strainer (BD, Le Pont De Claix, France) in complete RPMI 1640 medium (10% heat-inactivated fetal calf serum, 2 mM L-glutamine, 50 IU/ml penicillin, and 50 μg/ml streptomycin; Sigma-Aldrich), and $1 \times 10^6$ cells per well were cultured (37° C., 10% $CO_2$) for 48 h with stimulation by phorbol 12-myristate 13-acetate (PMA, 50 ng/ml; Sigma-Aldrich) and ionomycin (1 μM; Sigma-Aldrich). The culture supernatant was frozen at −80° C. until processing. To measure the cytokine levels in the colonic explants, tissues from the medium colon were isolated and rinsed in phosphate buffered saline (PBS; Gibco, Paisley, United Kingdom). The colonic explants were cultured (37° C., 10% $CO_2$) overnight in 24-well tissue culture plates (Costar, Corning, Amsterdam, The Netherlands) in 1 ml of complete RPMI 1640 medium. The culture supernatants were collected and stored at −80° C. until processing. ELISAs were performed on the supernatants to quantify mouse cytokines according to the manufacturer's instructions: IL10, IL17A, and IFNγ (Mabtech, Nacka Strand, Sweden); IL22 (eBioscience, San Diego, Calif., USA); and IL6 (R&D Systems, Minneapolis, Minn., USA). For the colonic explants, cytokine concentrations were normalized according to the dry weight of each colonic explant.

Lamina Propria Isolation and Flow Cytometry

Colonic and small intestine lamina propria cells were isolated as previously described[6]. The cells were stimulated and stained as previously described[6]. The following antibodies were used for surface staining: CD3 (145-2C11, eBioscience, San Diego, Calif., USA); CD4 (L3T4, BD, Le Pont De Claix, France); CD1 1b (M1/70, eBioscience); CD11c (N418, eBioscience); F4/80 (BM8, eBioscience); CD103 (M290, BD, Le Pont De Claix, France); MHCII (M5/114.15.2, BD, Le Pont De Claix, France); TCRγδ (eBioGL3, eBioscience); and NKp46 (29A1.4, eBioscience). Intracellular cytokine staining was performed using IL17A (TC11-18H10, BD, Le Pont De Claix, France) and IL22 (IL22JOP, eBioscience) antibodies. The cells were analyzed using a Gallios flow cytometer (Beckman Coulter, Brea, Calif., USA). Leukocytes were gated using FSC and SSC, and within the leukocytes gates, the innate immune cells were identified as macrophages ($MCHII^+F4/80^+CD103^-CD11b^+CD11c^-$) or dendritic cells ($MCHII^+F4/80^-CD103^{+/-}CD11b^-CD11c^+$). For the lymphoid compartment, the leukocytes were gated using FCS and SSC. Within the lymphocyte gate, the populations were identified as Th17 cells ($CD3^+CD4IL17^+$), Th22 cells ($CD3^+CD4IL22^+$), $NKp46^+$ ILC (including ILC3 and NK cells; $CD3^-CD4^-NKp46^+$), LTi cells ($CD3^-CD4^+NKp46^-$), or γδ T cells ($CD3^+CD4^-TCRγδ^+$).

Histology

Colon samples for histological studies were maintained at 4° C. in 4% paraformaldehyde and then embedded in paraffin. Four-micrometer sections were stained with hematoxylin and eosin (H&E) and then examined blindly using a BX43 Olympus microscope to determine the histological score according to previously described methods (6). The samples were also processed using a Starr Trek kit (Biocare Medical, Concord, Calif., USA) or a Novolink Polymer Detection System (Leica Biosystems, Heidelberg, Germany) to stain two mouse cell markers via immunohistochemistry, according to the manufacturer's instructions: mouse monoclonal anti-Ki67 antibody (Leica Biosystems) for cell proliferation and rabbit polyclonal anti-caspase-3 (cleaved-Asp175) antibody (Abcam, Cambridge, United Kingdom) for apoptosis. The number of cleaved caspase-3-positive cells in 100 μm of analyzed colon was counted. Ki67 was quantified as a percentage of the total height of each crypt. For each sample, 10 areas or crypts were analyzed.

Gene Expression Analysis Using Quantitative Reverse-Transcription PCR (qRT-PCR)

Total RNA was isolated from colon samples using an RNeasy Mini Kit (Qiagen, Hilden, Germany), according to the manufacturer's instructions. Quantitative RT-PCR was performed using SuperScript II Reverse Transcriptase (Life Technologies, Saint Aubin, France) and then a Takyon SYBR Green PCR kit (Eurogentec, Liege, Belgium) in a StepOnePlus apparatus (Applied Biosystems, Foster City, Calif., USA) with specific mouse oligonucleotides. We used the $2^{-\Delta\Delta Ct}$ quantification method with mouse Gapdh as an endogenous control and the WT or MWT group as a calibrator.

Fecal DNA Extraction and Fungal Quantification Via qPCR

Fecal DNA was extracted from the weighted stool samples as previously described (37). For the bead beating step, we used 0.1-mm diameter silica beads with 0.6-mm diameter beads to optimize fungal DNA extraction. DNA was then subjected to quantitative PCR using a Takyon SYBR Green PCR kit (Eurogentec, Liege, Belgium) for all fungal quantification or using TaqMan Gene Expression Assays (Life Technologies, Saint Aubin, France) for all bacterial quantification. The probes and primers for the bacterial 16S rRNA genes and primers for the fungal 18S rDNA genes described previously were used (18, 37). The threshold cycle for each sample was determined for each gene normalized to the $C_T$ value of the all-bacteria 16S ribosomal RNA gene. Data were calculated using the $2^{-\Delta\Delta Ct}$ method.

16S rRNA Gene Sequencing

DNA was isolated from the feces of mice before and after DSS treatment using the protocol described above. Microbial diversity was determined for each sample by targeting a portion of the ribosomal genes. A 16S rRNA gene fragment comprising V3 and V4 hypervariable regions was amplified using an optimized and standardized 16S-amplicon-library preparation protocol (Metabiote, GenoScreen, Lille, France). Briefly, 16S rRNA gene PCR was performed using 5 ng of genomic DNA according to the manufacturer's protocol (Metabiote) using 192 bar-coded primers (Metabiote MiSeq Primers, GenoScreen, Lille, France) at final concentrations of 0.2 μM and an annealing temperature of 50° C. for 30 cycles. The PCR products were purified using an Agencourt AMPure XP-PCR Purification system (Beckman Coulter, Brea, Calif., USA), quantified according to the manufacturer's protocol, and multiplexed at equal concentrations. Sequencing was performed using a 300-bp paired-end sequencing protocol on an Illumina MiSeq platform (Illumina, San Diego, Calif., USA) at GenoScreen, Lille, France. Raw paired-end reads were subjected to the following process: (1) quality filtering using the PRINSEQ-lite PERL script (38) by truncating the bases from the 3' end that did not exhibit a quality <30 based on the Phred algorithm; (2) paired-end read assembly using FLASH (39) (fast length adjustment of short reads to improve genome assemblies) with a minimum overlap of 30 bases and a 97% overlap identity; and (3) searching and removing both forward and reverse primer sequences using CutAdapt, with no mismatches allowed in the primers sequences. Assembled sequences for which perfect forward and reverse primers were not found were eliminated.

16S rRNA Gene Sequence Analysis

The sequences were demultiplexed, quality filtered using the Quantitative Insights Into Microbial Ecology (QIIME, version 1.8.0) software package(40), and the forward and reverse Illumina reads were joined using the fastq-join method (http://code.google.com/p/ea-utils). The sequences were assigned to OTUs using the UCLUST algorithm (41) with a 97% threshold of pairwise identity and classified taxonomically using the Greengenes reference database (42). Rarefaction was performed (39,048-84,722 sequences per sample) and used to compare the abundances of OTUs across samples.

ITS2 rRNA Gene Sequencing

DNA was isolated from feces of mice before and after DSS treatment using the protocol described above. Microbial diversity was determined for each sample by 454 pyrosequencing of the ribosomal genes. An ITS2 rRNA gene fragment of approximately 350 bases was amplified using the primers ITS2 and the optimized and standardized ITS2-amplicon-library preparation protocol (Metabiote, Geno-Screen, Lille, France). Briefly, for each sample, diluted genomic DNA was used for a 25-µl PCR conducted under the following conditions: 94° C. for 2 min; 35 cycles of 15 sec at 94° C., 52° C. for 30 sec and 72° C. for 45 sec; followed by 7 min at 72° C. The PCR products were purified using AmpureXP beads (Beckman Coulter, Brea, Calif., USA) and quantified using a PicoGreen staining kit (Molecular Probes, Paris, France). A second PCR of 9 cycles was then conducted under similar PCR conditions with the purified PCR products and 10-bp multiplex identifiers (SIM Identifiers) added to the primers at the 5' position to specifically identify each sample and avoid PCR biases. Finally, the PCR products were purified and quantified as described above. Sequencing was then performed using a Gs-FLX Titanium Sequencing Systems (Roche Life Science, Mannheim, Germany).

ITS2 Sequence Analysis

The sequences were demultiplexed, and quality was filtered using the Quantitative Insights Into Microbial Ecology (QIIME, version 1.8.0) software package (40). The sequences were trimmed for barcodes and PCR primers and were binned for a minimal sequence length of 150 bp, a minimal base quality threshold of 25, and a maximum homopolymers length of 7. The sequences were then assigned to OTUs using the UCLUST algorithm (41) with a 97% threshold of pairwise identity and classified taxonomically using the UNITE ITS database (alpha version 12_11) (43). Rarefaction was performed (2,696-9,757 sequences per sample) and used to compare the abundances of OTUs across samples. For both 16S and ITS2, principal component analyses (PCA) based on genus composition were performed using the R package ade4 (44) and used to assess the variations among experimental groups. The number of observed species and the Shannon diversity index were calculated using rarefied data (depth=2,675 sequences/sample for ITS2 and depth=39,931 sequences/sample for 16S) and used to characterize species diversity in a community. The sequencing data were deposited in the European Nucleotide Archive under accession number PRJEB9079.

Gene Expression by Microarray Analyses

Total RNA was isolated using the protocol described above. RNA integrity was verified using a Bioanalyser 2100 with RNA 6000 Nano chips (Agilent Technologies, Palo Alto, Calif., USA). Transcriptional profiling was performed on mouse colon samples using the SurePrint G3 Mouse GE 8×60K Microarray kit (Design ID: 028005, Agilent Technologies). Cyanine-3 (Cy3)-labeled cRNAs were prepared with 100 ng of total RNA using a One-Color Low Input Quick Amp Labeling kit (Agilent Technologies) and following the recommended protocol. The specific activities and cRNA yields were determined using a NanoDrop ND-1000 (Thermo Fisher Scientific, Waltham, Mass., USA). For each sample, 600 ng of Cy3-labeled cRNA (specific activity >11.0 pmol Cy3/µg of cRNA) were fragmented at 60° C. for 30 min and hybridized to the microarrays for 17 h at 65° C. in a rotating hybridization oven (Agilent Technologies). After hybridization, the microarrays were washed and then immediately dried. After washing, the slides were scanned using a G2565CA Scanner System (Agilent Technologies) at a resolution of 3 µm and a dynamic range of 20 bits. The resulting TIFF images were analyzed using the Feature Extraction Software v10.7.3.1 (Agilent Technologies) according to the GE1_107_Sep09 protocol. The microarray data were submitted to GEO under accession number GSE67577.

Microarray Analysis

Agilent Feature Extraction software was used to convert scanned signals into tab-delimited text that could be analyzed using third-party software. The R package agilp was used to pre-process the raw data. Box plots and PCAs were used to obtain a general overview of the data in terms of the within-array distributions of signals and between-sample variability. Agilent Feature Extraction software computed a P value for each probe in each array to test whether the scanned signals were significantly higher than the background signal. The null hypothesis was "the measured signal is equal to background signal". Detected probes were considered if the P value was lower than 0.05. The probes must have been present in at least 60% of samples per group and under at least one condition to be considered for analysis. To compare data from multiple arrays, the data were normalized to minimize the effect of non-biological differences. Quantile normalization (45) is a method that can quickly normalize within a set of samples without using a reference base. After normalization, spike-in, positive and negative control probes were removed from the normalized data. For the differential expression analysis, we used the limma eBayes test (46), which finds a compromise between the variance estimate for the gene under consideration and the average variance of all of the genes. The Benjamini-Hochberg correction method was used to control the false discovery rate (FDR). All significant gene lists were annotated for enriched biological functions and pathways using Ingenuity® Pathway Analysis (IPA). Significant canonical pathways had p-values below 0.05. We used Venn diagrams to globally visualize the overlap between all of the significant genes in the WT and $Card9^{-/-}$ comparisons. Thus, IPA was performed to test for the biological pathways enrichment of Venn's elements.

Luciferase Assay

The H1L1.1c2 cell line containing a stably integrated DRE-driven firefly luciferase reporter plasmid pGudLuc1.1 was provided by Michael S. Denison (University of California, Davis, Calif., USA) and has been described previously (47, 48). The cells were seeded in 96-well plates at $7.5 \times 10^4$ cells/well in 100 µl of complete DMEM medium (10% heat-inactivated fetal calf serum, 50 IU/ml penicillin, and 50 µg/ml streptomycin; Sigma-Aldrich) and cultured (37° C., 10% $CO_2$) for 24 h prior to treatment. Fresh stools from healthy and IBD patients in remission and from WT, Card9$^{-/-}$, MWT, MCard9$^{-/-}$, Ido1$^{-/-}$ and germ-free mice were collected, weighed and stored at –80° C. until processing. The stools were suspended, diluted to 100 mg/ml in PBS, centrifuged (5000 g, 15 min, 4° C.) and filtered (0.2 µm; VWR, Fontenay-sous-Bois, France). Lactobacillus and Bifidobacterium spp. were grown in MRS medium (BD Difco, Le Pont De Claix, France) supplemented with 10% cysteine (Sigma-Aldrich) at 37° C. under respectively aerobic and anaerobic conditions. Allobaculum stercoricanis (DSMZ 13633) was cultivated under the recommended culture condition listed in the DSMZ. Cultured supernatants of these bacteria were stored at –80° C. until processing. To assess agonistic activity, the cells were treated with stool suspensions diluted at 1:10 in complete DMEM medium with 0.1% DMSO or with cultured supernatants diluted at 2, 10 and 20% in complete DMEM medium. Controls consisted of cells treated with DMEM medium with 0.1% DMSO or bacteria culture media as the negative control or 10 nM of 2,3,7,8-tetrachlorodibenzo-p-dioxin (TCDD; Sigma Aldrich) diluted in DMEM medium with 0.1% DMSO as the positive control. After 24 h of incubation, wells were washed with 100 µl of PBS, and 50 µl of Promega lysis buffer was added to each well. The plates were shaken for 30 min to lyse the cells. After adding 100 µl of Promega-stabilized luciferase reagent, the luciferase activity was measured using a luminometer. The results were normalized based on the negative luciferase activity of the control.

HPLC-HRMS Analysis

Frozen-thawed stools from healthy and IBD patients in remission or from WT, Card9$^{-/-}$, MWT, MCard9$^{-/-}$, Ida1$^{-/-}$, and germ-free mice were extracted as previously described (49). L-tryptophan (L-Trp) and L-kynurenine (L-Kyn) were measured via HPLC using a coulometric electrode array (ESA Coultronics, ESA Laboratories, Chelsford, Mass., USA) (50). Quantifications were performed by referencing calibration curves obtained with internal standards. Other compounds (tryptamine and IAA) were quantified via LC-MS using a Waters ACQUITY ultra performance liquid chromatography (UPLC) system equipped with a binary solvent delivery manager and a sample manager (Waters Corporation, Milford, Mass., USA), coupled to a tandem quadrupole-time-of-flight (Q-TOF) mass spectrometer equipped with an electrospray interface (Waters Corporation). Compounds were identified by comparing with the accurate mass and the Rt of reference standards in our in-house library, and the accurate masses of the compounds were obtained from web-based resources, such as the Human Metabolome Database (http://www.hmdb.ca) and METLIN (http://metlin.scripps.edu).

Study of IBD Patients

All patients were recruited in the Gastroenterology Department of the Saint Antoine Hospital (Paris, France) and provided informed consent, and approval was obtained from the local ethics committee (Comite de Protection des Personnes Ile-de-France IV, Suivitheque study). Among 52 IBD patients included, 41 were genotyped for the rs10781499 and rs11145835 SNPs using Fluidigm, and among the 112 patients with IBD included, 101 were genotyped for the rs10781499, rs2066844, rs2066845, rs2066847, rs12994997, and rs11564258 SNPs using Fluidigm (UMR CNRS 8199, Lille, France).

NanoString

NanoString was performed and analyzed according to manufacturer recommendations.

Statistical Analyses

GraphPad Prism version 6.0 (San Diego, Calif., USA) was used for all analyses and preparation of graphs. For all data displayed in graphs, the results are expressed as the mean±s.e.m., and statistical analyses were performed using a 2-tailed Student's t-test for unpaired data or using the nonparametric MannWhitney test. Differences corresponding to P<0.05 were considered significant.

Results

Response of Card9$^{-/-}$ Mice to Induced Colitis

Card9$^{-/-}$ mice show impaired recovery after dextran sulfate sodium (DSS)-induced colitis, with delayed weight gain, greater histopathology alterations, and shortened colons compared with WT C57BL/6 mice (FIG. 7 a, b, c), due to an inappropriate immune response to colitis (6). Confirming impaired intestinal healing, these mice have a significant defect in epithelial cell proliferation and a high level of apoptosis, as shown by decreased staining for Ki67 and increased staining for cleaved caspase 3, respectively (FIG. 1a). To examine the mechanisms responsible for this defect in Card9$^{-/-}$ mice, we compared the colon transcriptomes of WT and Card9$^{-/-}$ mice before and during DSS-induced colitis. The mouse transcriptomes clustered according to genotype, displaying distinct patterns in WT and Card9$^{-/-}$ mice. The number of upregulated genes on day 7 was markedly higher in Card9$^{-/-}$ mice than in WT mice. Pathway analyses of the induced transcripts showed dominance of immune-related pathways, corresponding to a stronger signal in Card9$^{-/-}$ mice. Interestingly, the NOD-like receptor signaling pathway, in which CARD9 is involved, was an exception, exhibiting weaker activation in Card9$^{-/-}$ mice than in WT mice. During the recovery period on day 12, the pathways involved in cell proliferation and replication were significantly activated in WT mice compared with Card9$^{-/-}$ mice, confirming the healing defect in Card9$^{-/-}$ mice. Among the most induced and differentially expressed genes between Card9$^{-/-}$ and WT mice on day 7 and 12 were regenerating islet-derivative protein 3γ and β (RegIIIγ, RegIIIβ) and Il1β. The expression of antimicrobial proteins, such as the C-type lectins RegIIIγ and RegIIIβ, by intestinal epithelial cells is induced by IL22 (12, 13). Moreover, IL17A plays a protective role in concert with IL22 (14, 15). Using real-time qPCR, we showed decreased colonic expression of Il22, RegIIIγ, RegIIIβ, and Il17A on day 12 in Card9$^{-/-}$ mice (FIG. 1b). These results highlight the role of CARD9 and its effector IL22 in the appropriate immune response to and recovery from DSS-induced colitis. The major role played by IL22 and its target genes RegIIIγ and RegIIIβ in the response to bacterial and fungal infections (4, 6, 16, 17) raises the question of the specific role of the microbiota in Card9$^{-/-}$ hypersusceptibility to induced colitis.

Abnormal Gut Microbiota in Card9$^{-/-}$ Mice

The deregulation of IL22, RegIIIγ, and RegIIIβ expression after induction of colitis by DSS in Card9$^{-/-}$ mice led us to hypothesize that Card9$^{-/-}$ mice may have an altered gastrointestinal microbiota. We therefore explored the microbiota composition at the fungal and bacterial level at baseline and during colitis. In both Card9$^{-/-}$ and WT mice, the fungal load in the colon reached a peak at day 7, but this level was higher in Card9$^{-/-}$ mice (FIG. 2a). Very little is known regarding the diversity of the fungi that populate the murine gut and how fungi contribute to colitis in mice (18, 19). We therefore further analyzed the fungal fecal microbiota via high-throughput ITS2 sequencing. Principal component analysis (PCA) based on genus composition revealed major differences between WT and Card9$^{-/-}$ mice at day 0 and 7. Remarkably, the fungal composition in Card9$^{-/-}$ mice showed large changes across days 0, 7, and 12, whereas it evolved only slightly in WT mice, showing more robust resilience. Diversity as assessed by operational taxonomic unit (OTU) count confirmed this difference, corresponding to a higher resilience of the fungal microbiota from WT mice than Card9$^{-/-}$ mice (FIG. 2b). The fungi microbiota of WT and Card9$^{-/-}$ mice was dominated by Ascomycota, Basidiomycota and Zygomycota phyla. Using the LEfSe pipeline (20), we observed several differences in the basal fecal fungal microbiota composition, including decreased levels of Agaricomycetes (class), *Microdochium* (genus), and *Monographella nivalis*, and increased levels of Ascomycota (phylum), Microbotryomycetes (class), Hypocreales (order), and *Sporobolymyces* (genus) in Card9$^{-/-}$ mice compared to WT mice. In line with the PCA results, the fungal microbiota composition was more altered at day 7 and 12 in Card9$^{-/-}$ than in WT mice. In parallel, we explored the fecal bacterial microbiota composition via 16S sequencing. Although less marked than in the fungal microbiota, PCA revealed that the basal bacterial microbiota was different in WT and Card9$^{-/-}$ mice. Moreover, the shift in bacterial microbiota composition during colitis followed a similar pattern in WT and Card9$^{-/-}$ mice but with decreased stability in Card9$^{-/-}$ mice (FIG. 3). No significant difference was observed regarding biodiversity (FIG. 2c). The LEfSe analysis revealed significant differences at baseline, including decreases in Coriobacteriaceae (family), *Adlercreutzia* (genus), Actinobacteria (Phylum) and *Lactobacillus reuteri* in the Card9$^{-/-}$ mouse microbiota. In WT mice, we observed a negative correlation between bacterial and fungal biodiversity (FIG. 2d), suggesting an inter-kingdom relationship and possibly competition. Interestingly, a positive correlation was observed in Card9$^{-/-}$ mice, suggesting abnormal interactions within the gut ecosystem between bacteria and fungi with possible consequences on gut homeostasis (FIG. 2d and FIG. 8a). Overall, these data demonstrate that CARD9 plays a role in shaping both bacterial and fungal gut microbiota and that it is required to control fungal microbiota expansion during colitis. The magnitude of the dysbiosis in Card9$^{-/-}$ mice led us to question its role in the colitis susceptibility phenotype in these mice.

The Card9$^{-/-}$ Microbiota has Pro-Inflammatory Effects

Figure 4D:
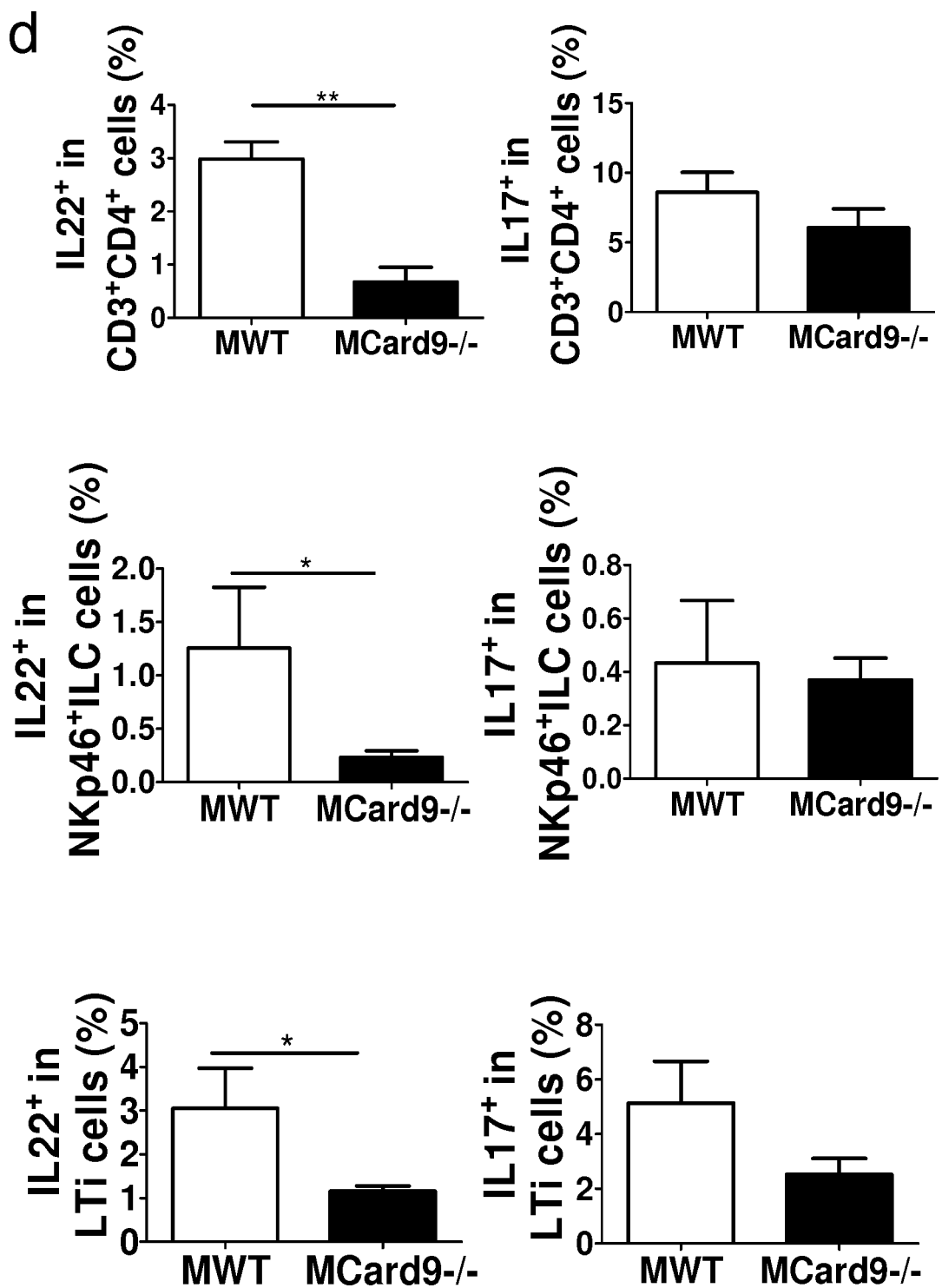

Following our hypothesis that the gut microbiota may play a role in the increased susceptibility of Card9$^{-/-}$ mice to DSS-induced colitis, we sought to isolate the effect of the gut microbiota. To test this hypothesis, we colonized WT germ-free (GF) mice with the microbiota of WT (MWT) (WT→GF) or of Card9$^{-/-}$ (MCard9$^{-/-}$) mice (Card9$^{-/-}$→GF) and exposed these mice to DSS. The microbiota transfer was sufficient to recapitulate the phenotype observed in Card9$^{-/-}$ mice, as evidenced by an increased susceptibility to colitis, impaired recovery with decreased epithelial cell proliferation, and increased apoptosis (FIG. 3a, b, c, FIG. 9a). However, the fungal portion of the microbiota was not involved in this effect, as fungal level was similar in MWT and MCard9$^{-/-}$ and antifungal treatment did not modify the phenotype (FIG. 9b, c, d). To decipher the mechanisms leading to the defective recovery from DSS-induced injury in MCard9$^{-/-}$ mice, we assessed the colonic expression levels of 179 inflammation-associated genes using NanoString technology. Il22 was one of the most highly downregulated genes in MCard9$^{-/-}$ mice compared with MWT mice, in addition to the chemokines Cxcl1 and Cxcl5 and the transcription factor Fos, which are all known IL22 target genes in epithelial cells (21-23). Il22 has been implicated in intestinal homeostasis (11) and mediates pivotal innate antimicrobial resistance in mice (10, 14). Furthermore, similar to Card9$^{-/-}$ and MCard9$^{-/-}$ mice, 1/22$^{-/-}$ mice are more susceptible to DSS-induced colitis and exhibit impaired healing during recovery (24). Therefore, we postulated that a deficient IL22 response may underlie the defective recovery of MCard9$^{-/-}$ during DSS-induced epithelial injury. One of the mechanisms by which IL22 enhances the mucosal barrier is through the induction of RegIIIβ and RegIIIγ[12,13]. Similar to and often in synergy with IL22, IL17A plays a protective role during infection with certain pathogens, including bacteria and fungi[14,15]. Therefore, we assessed the expression of these genes using real-time qPCR. In agreement with the NanoString results, Il22 expression was significantly decreased in MCard9$^{-/-}$ mice on days 0 and 12 (FIG. 4a). In line with these data, the expression levels of RegIIIγ and RegIIIβ were significantly lower in MCard9$^{-/-}$ mice than in MWT mice at day 0 and 7 (FIG. 4a). In contrast, no differences were observed in the expression levels of Il17A (FIG. 4a) and β-defensin 1 (DEFβ1), which is a target of IL17A (15) (FIG. 10a). We next confirmed the IL22 defect in MCard9$^{-/-}$ mice at the protein level, in both colon and mesenteric lymph nodes (MLNs) at baseline, day 7 and 12 (FIG. 4b, c). No significant differences were observed in the MLNs and the colon for IL17A, IL6, IFNgamma, and IL10 (FIG. 4b, c, FIG. 10b, c), suggesting that the IL22 axis is specifically impaired in MCard9$^{-/-}$ mice. No differences were observed when splenocytes were analyzed, suggesting a gut-limited defect in MCard9$^{-/-}$ mice (FIG. 10d). Several sources of IL22 have been identified in the gut, including innate lymphoid cells (ILC), natural killer (NK) cells, T helper 17 and 22 (Th17 and Th22) cells, γδ T cells, and lymphoid tissue inducer cells (LTi) (12, 25). Therefore, we isolated lymphoid cells from the gut intraepithelial compartment and the lamina propria to determine the type of cells involved in the reduction of IL22 production in MCard9$^{-/-}$ mice. The number of Th22, NKp46$^+$ ILC, and LTi cells producing IL22 was significantly decreased in the colon lamina propria of MCard9$^{-/-}$ mice compared with the MWT mice on day 12 (FIG. 4d). In contrast, IL17 production by these cells was not altered, and no difference was observed in IL22 and IL17 production by the γδ T cells (FIG. 4d, FIG. 11a). Intestinal dendritic cells and macrophages, which are involved in the stimulation of IL22-producing cells via IL23 production (12), were also explored, but no significant differences were observed between MCard9$^{-/-}$ and MWT mice (FIG. 11b). These data indicate that the microbiota of Card9$^{-/-}$ mice is defective in inducing IL22 production by T cells and ILCs in the colon, leading to impaired recovery from DSS-induced colitis.

Impaired Tryptophan Metabolism in MCard9$^{-/-}$ Mice

Our results suggest that the gut microbiota of Card9$^{-/-}$ mice contributes to susceptibility to DSS-induced colitis by altering IL22 signaling. One mechanism that could link these findings is the modulation of AhR activation by the microbiota within the gastrointestinal tract. In the gastrointestinal tract, tryptophan can be metabolized either by the gut bacteria into indole derivatives, such as indole-3-acetic-acid (IAA), or by host cells into kynurenine (Kyn) via indoleamine 2,3-dioxygenase 1 (Ido1; FIG. 12a) (10, 26, 27). Indole derivatives are AhR ligands (FIG. 7b) known to promote local IL22 production (28) by Th17/Th22 cells, γδ T cells, and NKp46$^+$ ILCs. Therefore, by examining the levels of AhR ligands in colon lumen of germ-free, Ido1$^{-/-}$, Card9$^{-/-}$, MCard9$^{-/-}$, WT, and MWT mice, we were able to analyze the tryptophan metabolism of the host and gut bacteria. As expected, Ido1$^{-/-}$ mice had an impaired production of Kyn with normal IAA levels, whereas germ-free mice had an impaired production of IAA (FIG. 5a, FIG. 12c, d). Kyn levels were also low in the germ-free mice, likely because of the underdevelopment of the gut immune system (FIG. 5a, FIG. 12c, d). Most notably, the levels of IAA in MCard9$^{-/-}$ and Card9$^{-/-}$ mice were drastically decreased, whereas the abundance of the microbiota was not modified (FIG. 5a, FIG. 12c, d, e) indicating that the change in the microbiota in Card9$^{-/-}$ mice was responsible for the low level of IAA. In line with these data, cultured supernatants of Lactobacillus reuteri and Allobaculum, two bacteria lacking in the Card9$^{-/-}$ mouse microbiota (FIG. 2c), strongly activate AhR (FIG. 13a). These results suggest that impaired tryptophan metabolism by the Card9$^{-/-}$ microbiota could be associated with or even responsible for the increased susceptibility of Card9$^{-/-}$ mice to induced colitis, a new concept in the IBD field.

To confirm the importance of tryptophan metabolism by the microbiota in our study, we used an AhR reporter system to show that feces from Card9$^{-/-}$ and MCard9$^{-/-}$ mice were defective in their ability to activate AhR, similar to germ-free mice (FIG. 5b, FIG. 13b). To assess in vivo the importance of this finding, we administered 6-formylindolo [3,2-b]carbazole (Ficz), an AhR agonist, to DSS-exposed mice. Ficz-treated MCard9$^{-/-}$ mice exhibited a weaker colitis severity (body weight loss, histology score, and colon shortening) than their non-treated counterparts during recovery, reaching the level of MWT mice (FIG. 5c, d). Accordingly, defects in Il22, RegIIIγ, and RegIIIβ colonic expression in MCard9$^{-/-}$ mice was rescued by Ficz administration (FIG. 5e). This effect was also observed at the protein level for IL22 (FIG. 5f). Il17 expression and production was not altered by Ficz treatment (FIG. 5 e, f). No significant differences between the Ficz-treated and non-treated MCard9$^{-/-}$ mice were observed in the colon for IL6, IL10 and IFNgamma (FIG. 13c). These results show that the gut microbiota of Card9$^{-/-}$ mice contributes to their susceptibility to colitis by altering the IL22 signaling pathway via impaired tryptophan metabolism, leading to defective AhR activation. Moreover, this defect can be effectively countered by an AhR agonist, representing a new potential therapeutic approach.

The inventors also demonstrated that the microbiota of Il22−/− mice is altered, and its transfer increases susceptibility of WT mice to colitis. Therefore, we postulated that a deficient IL-22 response may also be involved in the decreased production of AHR ligands by the microbiota. Indeed, microbiota from Il22−/− mice had impaired AHR activity and decreased levels of IAA. Moreover, administration of exogenous IL-22 was sufficient to normalize AHR ligand production and colitis susceptibility in Card9−/− mice. These results show that the gut microbiota of Card9−/− mice contributes to the susceptibility of the mice to colitis by altering the IL-22 signaling pathway via impaired tryptophan metabolism, leading to defective AHR activation. In addition, IL-22 is required for the production of AHR ligands by the microbiota. An AHR agonist can effectively counter these defects.

AhR Activation in IBD Patient Stool Samples

Thus far, we have established a role for CARD9 in recovery from colitis in mice through the control of the adequate production of AhR ligands by the microbiota, which leads to intestinal IL22 production. Next, we explored whether these findings were relevant to human IBD patients. We analyzed fecal samples from IBD patients and healthy subjects (HS) for their ability to activate AhR. The fecal samples from the HS induced significantly greater activation of AhR than those from the IBD patients (FIG. 6a). This finding was associated with decreased levels of tryptophan, increased levels of Kyn and decreased levels of IAA in the fecal samples of IBD patients compared with those of HS (FIG. 6b, FIG. 14a). Therefore, the activated immune cells in the gut of IBD patients may use tryptophan to produce Kyn via IDO, whereas the metabolism of tryptophan by the gut microbiota is impaired, leading to defective AhR activation. We next searched for a connection between CARD9 and the ability of the microbiota to produce AhR in humans. We genotyped 41 IBD patients for the CARD9 IBD-associated SNP (rs10781499) (29) and for a polymorphism in small nuclear RNA-activating complex polypeptide 4 (SNAPC4; rs11145835) associated with ankylosing spondylitis (30). The second SNP is located in a gene adjacent to CARD9, which is associated with decreased expression of CARD9 (30). For both SNPs, the risk allele was associated with reduced AhR activation by fecal microbiota metabolites (FIG. 6c). Moreover, the number of risk alleles correlated with the level of AhR activation. No correlation was observed among other major IBD SNPs, including NOD2, ATG16L1, and LRRK2 (FIG. 14b). These results should be confirmed in an independent cohort but suggest a connection between IBD, CARD9, and the ability of the microbiota to produce AhR agonists in humans.

The inventors identified and isolated bacterial probiotics exhibiting AhR activation properties by performing the method of screening of the invention and characterized said bacterial probiotics based on 16S gene sequence (FIG. 15) (51).

The inventors have deposited five of the characterized bacterial probiotics at the Collection at the Collection Nationale de Cultures de Microorganismes (CNCM, Institut Pasteur, 25 rue du Docteur Roux, 75724 Paris Cedex 15, France), in accordance with the terms of Budapest Treaty, on the 30th of September 2015. The deposited bacterial probiotics of Lactobacillus strains have CNCM deposit numbers CNCM I-5019 (SB6WTD3, Lactobacillus taiwanensis), CNCM I-5020 (SB6WTD4, Lactobacillus murinus), CNCM I-5021 (SB6WTD5, Lactobacillus animalis), CNCM I-5022 (SB6WTF6, Lactobacillus reuteri), and CNCM I-5023 (SB6WTG6, Lactobacillus reuteri) and are characterized based on 16S gene sequences described below.

```
>SEQ ID NO: 1 for CNCM I-5019 (SB6WTD3, Lactobacillus taiwanensis) R_premix
GACGGCTGACTCCTATAAAGGTTATCCCACCGGCTTTGGGTGTTACAGACTCTCATGGTGTGACGGGC

GGTGTGTACAAGGCCCGGGAACGTATTCACCGCGGCGTGCTGATCCGCGATTACTAGCGATTCCAGCT

TCGTGTAGGCGAGTTGCAGCCTACAGTCCGAACTGAGAACGGCTTTAAGAGATCCGCTTGCCTTCGCA

GGTTCGCTTCTCGTTGTACCGTCCATTGTAGCACGTGTGTAGCCCAGGTCATAAGGGGCATGATGACT

TGACGTCATCCCCACCTTCCTCCGGTTTGTCACCGGCAGTCTCATTAGAGTGCCCAACTTAATGATGG
```

-continued

CAACTAATGACAAGGGTTGCGCTCGTTGCGGGACTTAACCCAACATCTCACGACACGAGCTGACGACA

GCCATGCACCACCTGTCTCAGCGTCCCCGAAGGGAACACCTAATCTCTTAGGTTTGCACTGGATGTCA

AGACCTGGTAAGGTTCTTCGCGTTGCTTCGAATTAAACCACATGCTCCACCGCTTGTGCGGGCCCCCG

TCAATTCCTTTGAGTTTCAACCTTGCGGTCGTACTCCCCAGGCGGAGTGCTTAATGCGTTAGCTGCAG

CACTGAGAGGCGGAAACCTCCCAACACTTAGCACTCATCGTTTACGGCATGGACTACCAGGGTATCTA

ATCCTGTTCGCTACCCATGCTTTCGAGCCTCAGCGTCAGTTGCAGACCAGAGAGCCGCCTTCGCCACT

GGTGTTCTTCCATATATCTACGCATTCCACCGCTACACATGGAGTTCCACTCTCCTCTTCTGCACTCA

AGTTCAACAGTTTCTGATGCAATTCTCCGGTTGAGCCGAAGGCTTTCACATCAGACTTATTGAACCGC

CTGCACTCGCTTTACGCCCAATAAATCCGGACAACGCTTGCCA

>SEQ ID NO: 2 for CNCM I-5019 (SB6WTD3, *Lactobacillus taiwanensis*) F_premix
TACTGCAGTCGAGCGAGCTTGCCTAGATGATTTTAGTGCTTGCACTAAATGAAACTAGATACAAGCGA

GCGGCGGACGGGTGAGTAACACGTGGGTAACCTGCCCAAGAGACTGGGATAACACCTGGAAACAGATG

CTAATACCGGATAACAACACTAGACGCATGTCTAGAGTTTAAAAGATGGTTCTGCTATCACTCTTGGA

TGGACCTGCGGTGCATTAGCTAGTTGGTAAGGTAACGGCTTACCAAGGCAATGATGCATAGCCGAGTT

GAGAGACTGATCGGCCACATTGGGACTGAGACACGGCCCAAACTCATACGGGAGGCAGCAGTAGGGAA

TCTTCCACAATGGACGCAAGTCTGATGGAGCAACGCCGCGTGAGTGAAGAAGGGTTTCGGCTCGTAAA

GCTCTGTTGGTAGTGAAGAAAGATAGAGGTAGTAACTGGCCTTTATTTGACGGTAATTACCTAGAAAG

TCACGGCTAACTACGTGCCAGCAGCCGCGGTAATACGTAGGTGGCAAGCGTTGTCCGGATTTATTGGG

CGTAAAGCGAGTGCAGGCGGTTCAATAAGTCTGATGTGAAAGCCTTCGGCTCAACCGGAGAATTGCAT

CAGAAACTGTTGAACTTGAGTGCAGAAGAGGAGAGTGGAACTCCATGTGTAGCGGTGGAATGCGTAGA

TATATGGAAGAACACCAGTGGCGAAGGCGGCTCTCTGGTCTGCAACTGACGCTGAGGCTCGAAAGCAT

GGGTAGCGAACAGGATTAGATACCCTGGTAGTCCATGCCGTAAACGATGAGTGCTAAGTGTTGGGAGG

TTTCCGCCTCTCAGTGCTGCAGCTAACGCATTAAG

>SEQ ID NO: 3 for CNCM I-5020 (SB6WTD4, *Lactobacillus murinus*) R_premix
GCTCCAAAGGTTACCCCACCGGCTTTGGGTGTTACAAACTCTCATGGTGTGACGGGCGGTGTGTACAA

GGCCCGGGAACGTATTCACCGCGGCATGCTGATCCGCGATTACTAGCGATTCCGACTTCATGTAGGCG

AGTTGCAGCCTACAATCCGAACTGAGAACGGCTTTAAGAGATTTGCTAAACCTCGCGGTCTTGCGACT

CGTTGTACCGTCCATTGTAGCACGTGTGTAGCCCAGATCATAAGGGGCATGATGATTTGACGTCATCC

CCACCTTCCTCCGGTTTGTCACCGGCAGTCTTGCTAGAGTGCCCAACTTAATGCTGGCAACTAACAAT

AAGGGTTGCGCTCGTTGCGGGACTTAACCCAACATCTCACGACACGAGCTGACGACAACCATGCACCA

CCTGTCATTTTGTCCCCGAAGGGAAAGTCCTATCTCTAGGATTGTCAAAAGATGTCAAGACCTGGTAA

GGTTCTTCGCGTTGCTTCGAATTAAACCACATGCTCCACCGCTTGTGCGGGCCCCCGTCAATTCCTTT

GAGTTTCAACCTTGCGGTCGTACTCCCCAGGCGGAATGCTTATTGCGTTAGCTGCAGCACTGAAGGGC

GGAAACCCTCCAACACTTAGCATTCATCGTTTACGGCGTGGACTACCAGGGTATCTAATCCTGTTTGC

TACCCACGCTTTCGAACCTCAGCGTCAGTTACAGACCAGAGAGCCGCTTTCGCCACTGGTGTTCTTCC

ATATATCTACGCATTTCACCGCTACACATGGAGTTCCACTCTCCTCTTCTGCACTCAAGTCTCCCAGT

TTCCAATGCACTACTCCGGTTAAGCCGAAGGCTTTCACATCAGACTTAAAAGACCGCCTGCGTTCCCT

TTACGCCCAATAAATCCGGATAACGCTTGCCACCTACGTATTACCGCGGCTGCTGGCACGTAG

>SEQ ID NO: 4 for CNCM I-5020 (SB6WTD4, *Lactobacillus murinus*) F_premix
CGAACGAAACTTCTTTATCACCGAGTGCTTGCACTCACCGATAAAGAGTTGAGTGGCGAACGGGTGAG

TAACACGTGGGCAACCTGCCCAAAAGAGGGGGATAACACTTGGAAACAGGTGCTAATACCGCATAACC

ATAGTTACCGCATGGTAACTATGTAAAAGGTGGCTATGCTACCGCTTTTGGATGGGCCCGCGGCGCAT

-continued

TAGCTAGTTGGTGGGGTAAAGGCTTACCAAGGCAATGATGCGTAGCCGAACTGAGAGGTTGATCGGCC

ACATTGGGACTGAGACACGGCCCAAACTCCTACGGGAGGCAGCAGTAGGGAATCTTCCACAATGGGCG

AAAGCCTGATGGAGCAACGCCGCGTGGGTGAAGAAGGTCTTCGGATCGTAAAACCCTGTTGTTAGAGA

AGAAAGTGCGTGAGAGTAACTTTTC

>SEQ ID NO: 5 for CNCM I-5021 (SB6WTD5, *Lactobacillus animalis*) R_premix1
TGGTCGAAAGGTTACCCCACCGGCTTTGGGTGTTACAAACTCTCATGGTGTGACGGGCGGTGTGTACA

AGGCCCGGGAACGTATTCACCGCGGCATGCTGATCCGCGATTACTAGCGATTCCGACTTCATGTAGGC

GAGTTGCAGCCTACAATCCGAACTGAGAACGGCTTTAAGAGATTTGCTAAACCTCGCGGTCTTGCGAC

TCGTTGTACCGTCCATTGTAGCACGTGTGTAGCCCAGATCATAAGGGGCATGATGATTTGACGTCATC

CCCACCTTCCTCCGGTTTGTCACCGGCAGTCTTGCTAGAGTGCCCAACTTAATGCTGGCAACTAACAA

TAAGGGTTGCGCTCGTTGCGGGACTTAACCCAACATCTCACGACACGAGCTGACGACAACCATGCACC

ACCTGTCATTTTGTCCCCGAAGGGAAAGTCCTATCTCTAGGATTGTCAAAAGATGTCAAGACCTGGTA

AGGTTCTTCGCGTTGCTTCGAATTAAACCACATGCTCCACCGCTTGTGCGGGCCCCCGTCAATTCCTT

TGAGTTTCAACCTTGCGGTCGTACTCCCCAGGCGGAATGCTTATTGCGTTAGCTGCAGCACTGAAGGA

CGGAAACCCTCCAACACTTAGCATTCATCGTTTACGGCGTGGACTACCAGGGTATCTAATCCTGTTTG

CTACCCACGCTTTCGAACCTCAGCGTCAGTTACAGACCAGAGAGCCGCTTTCGCCACTGGTGTTCTTC

CATATATCTACGCATTTCACCGCTACACATGGAGTTCCACTCTCCTCTTCTGCACTCAAGTCTCCCAG

TTTCCAATGCACTACTCCGGTTAAGCCG

>SEQ ID NO: 6 for CNCM I-5021 (SB6WTD5, *Lactobacillus animalis*) R_premix2
GCGAGTTGCAGCCTACAATCCGAACTGAGAACGGCTTTAAGAGATTTGCTAAACCTCGCGGTCTTGCG

ACTCGTTGTACCGTCCATTGTAGCACGTGTGTAGCCCAGATCATAAGGGGCATGATGATTTGACGTCA

TCCCCACCTTCCTCCGGTTTGTCACCGGCAGTCTTGCTAGAGTGCCCAACTTAATGCTGGCAACTAAC

AATAAGGGTTGCGCTCGTTGCGGGACTTAACCCAACATCTCACGACACGAGCTGACGACAACCATGCA

CCACCTGTCATTTTGTCCCCGAAGGGAAAGTCCTATCTCTAGGATTGTCAAAAGATGTCAAGACCTGG

TAAGGTTCTTCGCGTTGCTTCGAATTAAACCACATGCTCCACCGCTTGTGCGGGCCCCCGTCAATTCC

TTTGAGTTTCAACCTTGCGGTCGTACTCCCCAGGCGGAATGCTTATTGCGTTAGCTGCAGCACTGAAG

GCGGAAACCCTCCAACACTTAGCATTCATCGTTTACGGCGTGGACTACCAGGGTATCTAATCCTGTT

TGCTACCCACGCTTTCGAACCTCAGCGTCAGTTACAGACCAGAGAGCCGCTTTCGCCACTGGTGTTCT

TCCATATATCTACGCATTTCACCGCTACACATGGAGTTCCACTCTCCTCTTCTGCACTCAAGTCTCCC

AGTTTCCAATGCACTACTCCGGTT

>SEQ ID NO: 7 for CNCM I-5021 (SB6WTD5, *Lactobacillus animalis*) F_premix1
AACTCATACGGGAGGCAGCAGTAGGGAATCTTCCACAATGGGCGAAAGCCTGATGGAGCAACGCCGCG

TGGGTGAAGAAGGTCTTCGGATCGTAAAACCCTGTTGTTAGAGAAGAAAGTGCGTGAGAGTAACTGTT

CACGTTTCGACGGTATCTAACCAGAAAGCCACGGCTAACTACGTGCCAGCAGCCGCGGTAATACGTAG

GTGGCAAGCGTTATCCGGATTTATTGGGCGTAAAGGGAACGCAGGCGGTCTTTTAAGTCTGATGTGAA

AGCCTTCGGCTTAACCGGAGTAGTGCATTGGAAACTGGGAGACTTGAGTGCAGAAGAGGAGAGTGGAA

CTCCATGTGTAGCGGTGAAATGCGT

>SEQ ID NO: 8 for CNCM I-5021 (SB6WTD5, *Lactobacillus animalis*) F_premix2
AATACTGCAGTCGAACGAAACTTCTTTATCACCGAGTGCTTGCACTCACCGATAAAGAGTTGAGTGGC

GAACGGGTGAGTAACACGTGGGCAACCTGCCCAAAAGAGGGGGATAACACTTGGAAACAGGTGCTAAT

ACCGCATAACCATAGTTACCGCATGGTAACATATGTAAAAGGTGGCTATGCTACCGCTTTGGATGGGC

CCGCGGCGCATTAGCTAGTTGGTGGGGTAAAGGCTTACCAAGGCAATGATGCGTAGCCGAACTGAGAG

-continued

GTTGATCGGCCACATTGGGACTGAGACACGGCCCAA

>SEQ ID NO: 9 for CNCM I-5022 (SB6WTF6, Lactobacillus reuteri) R_premix
CACGCCGACTTTGGGCGTTACAAACTCCCATGGTGTGACGGGCGGTGTGTACAAGGCCCGGGAACGTA

TTCACCGCGGCATGCTGATCCGCGATTACTAGCGATTCCGACTTCGTGTAGGCGAGTTGCAGCCTACA

GTCCGAACTGAGAACGGCTTTAAGAGATTAGCTTGCTCTCGCGAGTTTGCAACTCGTTGTACCGTCCA

TTGTAGCACGTGTGTAGCCCAGGTCATAAGGGGCATGATGATCTGACGTCGTCCCCACCTTCCTCCGG

TTTGTCACCGGCAGTCTCACTAGAGTGCCCAACTCAATGCTGGCAACTAGTAACAAGGGTTGCGCTCG

TTGCGGGACTTAACCCAACATCTCACGACACGAGCTGACGACGACCATGCACCACCTGTCATTGCGTC

CCCGAAGGGAACGCCTTATCTCTAAGGTTAGCGCAAGATGTCAAGACCTGGTAAGGTTCTTCGCGTAG

CTTCGAATTAAACCACATGCTCCACCGCTTGTGCGGGCCCCCGTCAATTCCTTTGAGTTTCAACCTTG

CGGTCGTACTCCCCAGGCGGAGTGCTTAATGCGTTAGCTCCGGCACTGAAGGGCGGAAACCCTCCAAC

ACCTAGCACTCATCGTTTACGGCATGGACTACCAGGGTATCTAATCCTGTTCGCTACCCATGCTTTCG

AGCCTCAGCGTCAGTTGCAGACCAGACAGCCGCCTTCGCCACTGGTGTTCTTCCATATATCTACGCAT

TCCACCGCTACACATGGAGTTCCACTGTCCTCTTCTGCACTCAAGTCGCCCGGTTTCCGATGCACTTC

TTCGGTTAAGCCGAAGGCTTTCAC

>SEQ ID NO: 10 for CNCM I-5022 (SB6WTF6, Lactobacillus reuteri) F_premix1
CCTACGGGAGGCAGCAGTAGGGAATCTTCCACAATGGGCGCAAGCCTGATGGAGCAACACCGCGTGAG

TGAAGAAGGGTTTCGGCTCGTAAAGCTCTGTTGTTGGAGAAGAACGTGCGTGAGAGTAACTGTTCATG

CAGTGACGGTATCCAACCAGAAAGTCACGGCTAACTACGTGCCAGCAGCCGCGGTAATACGTAGGTGG

CAAGCGTTATCCGGATTTATTGGGCGTAAAGCGAGCGCAGGCGGTTGCTTAGGTCTGATGTGAAAGCC

TTCGGCTTAACCGAAGAAGTGCATCGGAAACCGGGCGACTTGAGTGCAGAAGAGGACAGTGGAACTCC

ATGTGTAGCGTGGAA

>SEQ ID NO: 11 for CNCM I-5022 (SB6WTF6, Lactobacillus reuteri) F_premix2
ATGGATCACCAGTGAGTGGCGGACGGGTGAGTAACACGTAGGTAACCTGCCCCGGAGCGGGGGATAAC

ATTTGGAAACAGATGCTAATACCGCATAACAACAAAAGCCGCATGGCTTTTATTTGAAAGATGGCTTT

GGCTATCACTCTGGGATGGACCTGCGGTGCATTAGCTAGTTGGTAAGGTAACGGCTTACCAAGGCGAT

GATGCATAGCCGAGTTGAGAGACTGATCGGCCACAATGGAACTGAGACACGGTCCATACTCATACGG

>SEQ ID NO: 12 for CNCM I-5023 (SB6WTG6, Lactobacillus reuteri) R_premix
AACGCCGACTTTGGGCGTTACAAACTCCCATGGTGTGACGGGCGGTGTGTACAAGGCCCGGGAACGTA

TTCACCGCGGCATGCTGATCCGCGATTACTAGCGATTCCGACTTCGTGTAGGCGAGTTGCAGCCTACA

GTCCGAACTGAGAACGGCTTTAAGAGATTAGCTTGCTCTCGCGAGTTTGCAACTCGTTGTACCGTCCA

TTGTAGCACGTGTGTAGCCCAGGTCATAAGGGGCATGATGATCTGACGTCGTCCCCACCTTCCTCCGG

TTTGTCACCGGCAGTCTCACTAGAGTGCCCAACTCAATGCTGGCAACTAGTAACAAGGGTTGCGCTCG

TTGCGGGACTTAACCCAACATCTCACGACACGAGCTGACGACGACCATGCACCACCTGTCATTGCGTC

CCCGAAGGGAACGCCTTATCTCTAAGGTTAGCGCAAGATGTCAAGACCTGGTAAGGTTCTTCGCGTAG

CTTCGAATTAAACCACATGCTCCACCGCTTGTGCGGGCCCCCGTCAATTCCTTTGAGTTTCAACCTTG

CGGTCGTACTCCCCAGGCGGAGTGCTTAATGCGTTAGCTCCGGCACTGAAGGGCGGAAACCCTCCAAC

ACCTAGCACTCATCGTTTACGGCATGGACTACCAGGGTATCTAATCCTGTTCGCTACCCATGCTTTCG

AGCCTCAGCGTCAGTTGCAGACCAGACAGCCGCCTTCGCCACTGGTGTTCTTCCATATATCTACGCAT

TCCACCGCTACACATGGAGTTCCACTGTCCTCTTCTGCACTCAAGTCGCCCGGTTTCCGATGCACTTC

TTCGGTTAAGCCGAAGGCTTTCACATCAGACCTAAGCAACCGCCTGCGCTCG

-continued

>SEQ ID NO: 13 for CNCM I-5023 (SB6WTG6, Lactobacillus reuteri) F_premix
AAGCCACATGGCTTTTATTTGAAAGATGGCTTTGGCTATCACTCTGGGATGGACCTGCGGTGCATTAG

CTAGTTGGTAAGGTAACGGCTTACCAAGGCGATGATGCATAGCCGAGTTGAGAGACTGATCGGCCACA

ATGGAACTGAGACACGGTCCATACTCCTACGGGAGGCAGCAGTAGGGAATCTTCCACAATGGGCGCAA

GCCTGATGGAGCAACACCGCGTGAGTGAAGAAGGGTTTCGGCTCGTAAAGCTCTGTTGTTGGAGAAGA

ACGTGCGTGAGAGTAACTGTTCATGCAGTGACGGTATCCAACCAGAAAGTCACGGCTAACTACGTGCC

AGCAGCCGCGGTAATACGTAGGTGGCAAGCGTTATCCGGATTTATTGGGCGTAAAGCGAGCGCAGGCG

GTTGCTTAGGTCTGATGTGAAAGCCTTCGGCTTAACCGAAGAAGTGCATCGGAAACCGGGCGACTTGA

GTGCAGAAGAGGACAGTGGAACTCCATGTGTAGCGGTGGAATGCGTAGATATATGGAAGAACACCAGT

GGCGAAGGCGGCTGTCTGGTCTGCAACTGACGCTGAGGCTCGAAAGCATGGGTAGCGAACAGGATTAG

ATACCCTGGTAGTCCATGCCGTAAACGATGAGTGCTAGGTGTTGGAGGGTTTCCGCCCTTCAGTGCCG

GAGCTAACGCATTAAGCACTCC

Accession Codes

European Nucleotide Archive: the sequencing data are deposited under accession number PRJEB9079 (Sequence Read Archive (SRA) accession number: ERP010137; ENA-SUBMISSION: ERA429301). Gene Expression Omnibus: the microarray data are available under accession number GSE67577 (51).

Discussion

The gut microbiota is a key player in mammalian physiology, and its composition is influenced by genetics, environment, and diet (1-3). Any change in these factors can predispose the host to metabolic or inflammatory disorders, including obesity, irritable bowel syndrome, and IBD (1-3). However, the mechanisms by which the microbiota influences the host remain unknown. It is also unclear whether dysbiosis is a cause or a consequence of these diseases. Our results showed that Card9 deletion has a dramatic effect on the gut microbiota and that transfer of microbiota from $Card9^{-/-}$ mice into WT germ-free recipient mice is sufficient to recapitulate the defective IL22 activation and the increased sensitivity to colitis observed in $Card9^{-/-}$ mice. These alterations were due to an impaired ability of the microbiota of $Card9^{-/-}$ mice to catabolize tryptophan into AhR ligands.

Metabolomics studies have revealed large effects of the gut microbiota on host metabolism (31). Indole derivatives, which are tryptophan catabolites of the microbiota, were recently identified as activators of AhR, consequently regulating local IL22 production by Th17/Th22, γδ T cells, and NKp46+ ILCs (10, 11, 28). Any modification in AhR ligand production impacts IL22 levels, and therefore acts on the fragile equilibrium between microbiota and host cells (10, 32, 33). In accordance with this model, the $Card9^{-/-}$ mouse microbiota exhibits decreased levels of bacteria that have tryptophan-catabolizing functions, such as *Lactobacillus reuteri*, the genera *Adlercreutzia* and *Allobaculum* (see https://img.jgi.doe.gov/cgi-bin/imgm_hmp/main.cgi), and the phylum Actinobacteria[10,34]. Thus, our results provide evidence that defects in innate immunity genes such as CARD9 can shape an altered microbiota, which can then modify the host immune response, in this case via the AhR pathway. Additionally, IDO1, which is expressed by a variety of host immune and non-immune cells, also catalyzes tryptophan into kynurenine, which is recognized as a suppressor of inflammation, inducing immune tolerance (35). Thus, tryptophan catabolism through IDO and the gut microbiota has a central role in the regulation of intestinal immune cell homeostasis. Moreover, our results are relevant to humans, as impaired microbiota production of AhR ligands is observed in IBD patients and correlates with CARD9 genotype. Consequently, the tryptophan catabolites of gut microbiota could be used as biomarkers for dysbiosis and could be targeted for the development of new therapeutic drugs for IBD. For instance, indole derivatives or probiotics that produce them[10] could be used as a supportive therapy during intestinal dysbiosis. Our findings support a more general concept that, due to the tight relationship between host factors and the gut microbiota, their respective roles in IBD pathogenesis cannot be completely distinguished. Thus, dysbiosis should not be considered a cause or a consequence of IBD, but both simultaneously. We hypothesize that the altered immune response in $Card9^{-/-}$ mice has a primary effect on the microbiota. In turn, the modified microbiota alters tryptophan catabolite production, affecting the immune response of the host and amplifying dysbiosis in a vicious circle that leads to the loss of intestinal homeostasis.

Example 2

Induction of DSS Colitis and Treatments.

To induce colitis, mice were administered drinking water supplemented with 2% (wt./vol.) dextran sulfate sodium (DSS; MP Biomedicals, LLC, Aurora, Ohio, USA) for 7 days and were then allowed to recover by drinking unsupplemented water for the next 5 days. The 6-formylindolo(3,2-b)carbazole (Ficz; Enzo Life Sciences, Lausen, Switzerland) and the AHR antagonist CH223191 (AHR; Sigma-Aldrich) were resuspended in dimethyl sulfoxide (DMSO; Sigma-Aldrich) and administered intraperitoneally. Ficz was injected 1 day after DSS administration (1 µg/mouse). For the AHR treatment, WT→GF and Card9-/- →GF mice (4- to 5-week-old females) were treated (100 µg/mouse) three times per week until euthanization. Controls consisted of mice injected with DMSO vehicle alone for the Ficz and AHR treatment groups. Three bacteria with strong AHR activity and that were isolated in feces of WT mice were identified by sequencing the 16S rDNA gene as previously described (52). The resulting sequences were aligned, inspected by eye, and compared with the online tool BLAST. Strains were identified based on the highest hit scores. These strains were deposited in the Collection Nationale de Cultures de Microorganismes (CNCM) of the Institut Pasteur and named *L. murinus* CNCM I-5020, *L. reuteri* CNCM I-5022, and *L. taiwanensis* CNCM I-5019. Bacterial suspensions containing these three strains (109 colony-forming units (c.f.u.) of each strain in 500 µl of PBS) were administered three times per week for a period of 3 weeks to WT→GF and Card9−/−→GF mice (4- to 5-week-old females) by intragastric gavage. Oral gavage with PBS was performed in control mice. For the antifungal treatment, mice were fed 0.5 mg/ml fluconazole in drinking water (Sigma-Aldrich) 1 week before DSS administration and every day thereafter, as previously described (18) (FIG. 9c). For the IL-22 treatment, WT and Card9−/− mice were injected intraperitoneally three times per week with mouse IL-22-Fc (50 µg/mouse) (Genentech, South San Francisco, Calif., USA) (WT IL-22 and Card9−/−IL-22) or an equivalent amount of isotype control (IgG2a) (Genentech) (WT isotype and Card9−/− isotype) for a period of 3 weeks. 3 d after the last injections, colitis was induced by DSS treatment. In all treatments, body weight, blood in stool, and stool consistency were analyzed daily. The severity of colitis was assessed using the disease activity index (DAI) as previously described (6).

Inoculation with Lactobacilli that Metabolize Tryptophan and Produce AHR Ligands Reduces Colitis in an AHR-Dependent Manner The inventors demonstrated that supplementation of Card9$^{-/-}$→GF mice with three *Lactobacillus* strains*L. murinus* CNCM I-5020, *L. reuteri* CNCM I-5022, and *L. taiwanensis* CNCM I-5019, isolated from WT mice for their ability to activate AHR (FIGS. 16 A and B), rescued susceptibility of Card9$^{-/-}$→GF mice to colitis, IL-22 expression, and AHR ligand production (data not shown). These effects were mediated by AHR, as they were abrogated in the presence of an AHR antagonist (data not shown) (Lamas et al., 2016).

REFERENCES

Throughout this application, various references describe the state of the art to which this invention pertains. The disclosures of these references are hereby incorporated by reference into the present disclosure.

1. Silva, M. J. et al. The Multifaceted Role of Commensal Microbiota in Homeostasis and Gastrointestinal Diseases. J Immunol Res 2015, 321241 (2015).
2. Molodecky, N. A. et al. Increasing incidence and prevalence of the inflammatory bowel diseases with time, based on systematic review. Gastroenterology 142, 46-54.e42; quiz e30 (2012).
3. Ananthakrishnan, A. N. Epidemiology and risk factors for IBD. Nat Rev Gastroenterol Hepatol (2015). doi:10.1038/nrgastro.2015.34
4. Lanternier, F. et al. Inherited CARD9 deficiency in otherwise healthy children and adults with *Candida* species-induced meningoencephalitis, colitis, or both. J. Allergy Clin. Immunol. (2015). doi:10.1016/j.jaci.2014.12.1930
5. Jachiet, M. et al. Posaconazole Treatment of Extensive Skin and Nail Dermatophytosis Due to Autosomal Recessive Deficiency of CARD9. JAMA Dermatol 151, 192-4 (2015).
6. Sokol, H. et al. Card9 mediates intestinal epithelial cell restitution, T-helper 17 responses, and control of bacterial infection in mice. Gastroenterology 145, 591-601.e3 (2013).
7. Darfeuille-Michaud, A. et al. High prevalence of adherent-invasive *Escherichia coli* associated with ileal mucosa in Crohn's disease. Gastroenterology 127, 412-21 (2004).
8. Sokol, H. et al. *Faecalibacterium prausnitzii* is an anti-inflammatory commensal bacterium identified by gut microbiota analysis of Crohn disease patients. Proc. Natl. Acad. Sci. U.S.A. 105, 16731-6 (2008).
9. Atarashi, K. et al. Treg induction by a rationally selected mixture of Clostridia strains from the human microbiota. Nature 500, 232-6 (2013).
10. Zelante, T. et al. Tryptophan catabolites from microbiota engage aryl hydrocarbon receptor and balance mucosal reactivity via interleukin-22. Immunity 39, 372-85 (2013).
11. Rutz, S., Eidenschenk, C. & Ouyang, W. IL-22, not simply a Th17 cytokine. Immunol. Rev. 252, 116-32 (2013).
12. Sonnenberg, G. F., Fouser, L. A. & Artis, D. Border patrol: regulation of immunity, inflammation and tissue homeostasis at barrier surfaces by IL-22. Nat. Immunol. 12, 383-90 (2011).
13. Stelter, C. et al. *Salmonella*-induced mucosal lectin RegIIIβ kills competing gut microbiota. PLoS ONE 6, e20749 (2011).
14. De Luca, A. et al. IL-22 defines a novel immune pathway of antifungal resistance. Mucosal Immunol 3, 361-73 (2010).
15. Ishigame, H. et al. Differential roles of interleukin-17A and -17F in host defense against mucoepithelial bacterial infection and allergic responses. Immunity 30, 108-19 (2009).
16. Hsu, Y.-M. S. M. et al. The adaptor protein CARD9 is required for innate immune responses to intracellular pathogens. Nat. Immunol. 8, 198-205 (2007).
17. Wu, W., Hsu, Y.-M. S. M., Bi, L., Songyang, Z. & Lin, X. CARD9 facilitates microbe-elicited production of reactive oxygen species by regulating the LyGDI-Rac 1 complex. Nat. Immunol. 10, 1208-14 (2009).
18. Iliev, I. et al. Interactions between commensal fungi and the C-type lectin receptor Dectin-1 influence colitis. Science (New York, N.Y.) 336, 1314-7 (2012).
19. Richard, M. L., Lamas, B., Liguori, G., Hoffmann, T. W. & Sokol, H. Gut fungal microbiota: the Yin and Yang of inflammatory bowel disease. Inflamm. Bowel Dis. 21, 656-65 (2015).
20. Segata, N. et al. Metagenomic biomarker discovery and explanation. Genome Biol. 12, R60 (2011).
21. Kim, K. et al. Interleukin-22 promotes epithelial cell transformation and breast tumorigenesis via MAP3K8 activation. Carcinogenesis 35, 1352-61 (2014).
22. Andoh, A. et al. Interleukin-22, a member of the IL-10 subfamily, induces inflammatory responses in colonic subepithelial myofibroblasts. Gastroenterology 129, 969-84 (2005).
23. Sabat, R., Ouyang, W. & Wolk, K. Therapeutic opportunities of the IL-22-IL-22R1 system. Nat Rev Drug Discov 13, 21-38 (2014).
24. Pickert, G. et al. STAT3 links IL-22 signaling in intestinal epithelial cells to mucosal wound healing. J. Exp. Med. 206, 1465-72 (2009).
25. Spits, H. et al. Innate lymphoid cells—a proposal for uniform nomenclature. Nat. Rev. Immunol. 13, 145-9 (2013).
26. Chung, K.-T. & Gadupudi, G. S. Possible roles of excess tryptophan metabolites in cancer. Environ. Mol. Mutagen. 52, 81-104 (2011).

27. Jin, U.-H. H. et al. Microbiome-derived tryptophan metabolites and their aryl hydrocarbon receptor-dependent agonist and antagonist activities. Mol. Pharmacol. 85, 777-88 (2014).
28. Lee, J. S. et al. AHR drives the development of gut ILC22 cells and postnatal lymphoid tissues via pathways dependent on and independent of Notch. Nat. Immunol. 13, 144-51 (2012).
29. Jostins, L. et al. Host-microbe interactions have shaped the genetic architecture of inflammatory bowel disease. Nature 491, 119-24 (2012).
30. Ma, X. et al. Evidence for genetic association of CARD9 and SNAPC4 with ankylosing spondylitis in a Chinese Han population. J. Rheumatol. 41, 318-24 (2014).
31. Wikoff, W. R. et al. Metabolomics analysis reveals large effects of gut microflora on mammalian blood metabolites. Proc. Natl. Acad. Sci. U.S.A. 106, 3698-703 (2009).
32. Zenewicz, L. et al. IL-22 deficiency alters colonic microbiota to be transmissible and colitogenic. Journal of immunology (Baltimore, Md.: 1950) 190, 5306-12 (2013).
33. Behnsen, J. et al. The cytokine IL-22 promotes pathogen colonization by suppressing related commensal bacteria. Immunity 40, 262-73 (2014).
34. Lin, L. & Xu, X. Indole-3-acetic acid production by endophytic *Streptomyces* sp. En-1 isolated from medicinal plants. Curr. Microbiol. 67, 209-17 (2013).
35. Munn, D. H. & Mellor, A. L. Indoleamine 2,3 dioxygenase and metabolic control of immune responses. Trends Immunol. 34, 137-43 (2013).
36. Hara, H. et al. The adaptor protein CARD9 is essential for the activation of myeloid cells through ITAM-associated and Toll-like receptors. Nat. Immunol. 8, 619-29 (2007).
37. Tomas, J. et al. Primocolonization is associated with colonic epithelial maturation during conventionalization. FASEB J. 27, 645-55 (2013).
38. Schmieder, R. & Edwards, R. Quality control and preprocessing of metagenomic datasets. Bioinformatics 27, 863-4 (2011).
39. Maga, T. & Salzberg, S. L. FLASH: fast length adjustment of short reads to improve genome assemblies. Bioinformatics 27, 2957-63 (2011).
40. Caporaso, J. G. et al. QIIME allows analysis of high-throughput community sequencing data. Nat. Methods 7, 335-6 (2010).
41. Edgar, R. C. Search and clustering orders of magnitude faster than BLAST. Bioinformatics 26, 2460-1 (2010).
42. McDonald, D. et al. An improved Greengenes taxonomy with explicit ranks for ecological and evolutionary analyses of bacteria and archaea. ISME J 6, 610-8 (2012).
43. KOljalg, U. et al. Towards a unified paradigm for sequence-based identification of fungi. Mol. Ecol. 22, 5271-7 (2013).
44. Thioulouse, J., Chessel, D., Dolédec, S. & Olivier, J. ADE-4: a multivariate analysis and graphical display software. Statistics and Computing 7, 75-83 (1997).
45. Bolstad, B. M., Irizarry, R. A., Astrand, M. & Speed, T. P. A comparison of normalization methods for high density oligonucleotide array data based on variance and bias. Bioinformatics 19, 185-93 (2003).
46. Smyth, G. K. Linear models and empirical bayes methods for assessing differential expression in microarray experiments. Stat Appl Genet Mol Biol 3, Article3 (2004).
47. Zhao, B. et al. Common commercial and consumer products contain activators of the aryl hydrocarbon (dioxin) receptor. PLoS ONE 8, e56860 (2013).
48. He, G., Zhao, B. & Denison, M. S. Identification of benzothiazole derivatives and polycyclic aromatic hydrocarbons as aryl hydrocarbon receptor agonists present in tire extracts. Environ. Toxicol. Chem. 30, 1915-25 (2011).
49. Gao, X. et al. Metabolite analysis of human fecal water by gas chromatography/mass spectrometry with ethyl chloroformate derivatization. Anal. Biochem. 393, 163-75 (2009).
50. Maneglier, B. et al. Simultaneous measurement of kynurenine and tryptophan in human plasma and supernatants of cultured human cells by HPLC with coulometric detection. Clin. Chem. 50, 2166-8 (2004).
51. Lamas, B et al. CARD9 impacts colitis by altering gut microbiota metabolism of tryptophan into aryl hydrocarbon receptor ligands. Nat Med. 22(6), 598-605 (2016).
52. Suau, A. et al. Direct analysis of genes encoding 16S rRNA from complex communities reveals many novel molecular species within the human gut. Appl. Environ. Microbiol. 65, 4799-4807 (1999).

The invention claimed is:

1. A method of preventing or treating an inflammatory bowel disease (IBD) in a subject in need thereof comprising the steps of: i) determining the Ahr activity of the microbiota in a feces sample obtained from the subject; ii) comparing Ahr activity, determined at step i) with a predetermined reference value; and iii) administering the subject with at least one agent selected from the group consisting of AhR agonists, bacterial probiotics with AhR agonist activity, and an IL-22 agonist when Ahr activity determined at step i) is lower than the predetermined reference value.

2. The method of claim 1, wherein said AhR agonist is selected from the group consisting of indoles derivatives, tryptophan catabolites of the microbiota, kynurenine, kynurenic acid, indole-3-aldehyde (IAld), tryptamine, indole 3-acetate, 3-indoxyl sulfate, 6-formylindolo(3,2-b) carbazole (Ficz), 2,3,7,8-tetrachlorodibenzo-p-dioxin (TCDD), tryptophan derivatives, flavonoids, biphenyls, Card9 agonists, Card9 expression activators, AhR modulator (SAhRM), diindolylmethane (DIM), methyl-substituted diindolylmethanes, dihalo- and dialkylDIM analogs, mexiletine, β-naphthoflavone (βNF) (5,6 benzoflavone (5,6 BZF), 1,4-dihydroxy-2-naphthoic acid (DHNA) and natural AhR Agonists (NAhRAs).

3. The method of claim 1, wherein said bacterial probiotic is selected from the group consisting of bacterial probiotics deposited under CNCM deposit numbers CNCM I-5019, CNCM I-5020, CNCM I-5021, CNCM I-5022 and CNCM I-5023.

4. The method of claim 3, wherein said bacterial probiotic has been deposited as CNCM I-5023.

5. The method of claim 3, wherein said bacterial probiotic has been deposited as CNCM I-5022.

6. The method of claim 1, wherein said bacterial probiotic is *Lactobacillus reuteri*.

7. The method of claim 1, wherein said at least one agent is an AhR agonist.

8. The method of claim 1, wherein the bacterial probiotic is an *Allobaculum, Lactobacillus reuteri, Lactobacillus taiwanensis, Lactobacillus johnsonii, Lactobacillus animalis, Lactobacillus murinus*, the genus *Adlercreutzia*, the phylum Actinobacteria, lactic acid bacterium, *Lactobacillus bulgaricus, Streptococcus thermophilus, Bifidobacterium*, Propionic acid bacterium, *Bacteroides, Eubacterium*, anaerobic *Streptococcus, Enterococcus, Lactobacillus delbrueckii* subsp. *bulgaricus* or *Escherichia coli*.

9. The method of claim 1, wherein said at least one agent is a bacterial probiotic with AhR agonist activity.

10. The method of claim 1, wherein said at least one agent is an IL-22 agonist.

* * * * *

UNITED STATES PATENT AND TRADEMARK OFFICE
CERTIFICATE OF CORRECTION

| | |
|---|---|
| PATENT NO. | : 10,736,927 B2 |
| APPLICATION NO. | : 15/753475 |
| DATED | : August 11, 2020 |
| INVENTOR(S) | : Harry Sokol et al. |

Page 1 of 1

It is certified that error appears in the above-identified patent and that said Letters Patent is hereby corrected as shown below:

On the Title Page

Item (71), "INSTITUT NATIONAL DE LA RECHERCHE AGRONOMIQUE (IRNA)" should read --INSTITUT NATIONAL DE RECHERCHE POUR L'AGRICULTURE, L'ALIMENTATION ET L'ENVIRONNEMENT--.

In the Specification

<u>Column 12,</u>
Line 10, "†NWT" should read --†MWT--.

<u>Column 13,</u>
Line 1, "Def/31" should read --*Defβ1*--.
Line 3, "Deffil" should read --*Defβ1*--.

<u>Column 14,</u>
Line 19, "MannWhitney" should read --Mann–Whitney--.

<u>Column 19,</u>
Line 36, "Idal$^{-/-}$," should read --Idol$^{-/-}$,--.

Signed and Sealed this
Second Day of February, 2021

Drew Hirshfeld
*Performing the Functions and Duties of the
Under Secretary of Commerce for Intellectual Property and
Director of the United States Patent and Trademark Office*